US011244452B2

(12) United States Patent
Castro-Gonzalez et al.

(10) Patent No.: US 11,244,452 B2
(45) Date of Patent: Feb. 8, 2022

(54) SYSTEMS, DEVICES AND METHODS FOR NON-INVASIVE HEMATOLOGICAL MEASUREMENTS

(71) Applicants: Massachusetts Institute of Technology, Cambridge, MA (US); Universidad Politecnica De Madrid, Madrid (ES)

(72) Inventors: Carlos Castro-Gonzalez, Cambridge, MA (US); Ian Butterworth, Cambridge, MA (US); Aurelien Bourquard, Cambridge, MA (US); Alvaro Sanchez-Ferro, Madrid (ES); Jason Tucker-Schwartz, Melrose, MA (US); Alberto Pablo-Trinidad, Madrid (ES); Maria J. Ledesma-Carbayo, Madrid (ES); Tom Vettenburg, Dundee (GB)

(73) Assignee: Massachusetts Institute of Technology, Cambridge, MA (US)

( * ) Notice: Subject to any disclaimer, the term of this patent is extended or adjusted under 35 U.S.C. 154(b) by 621 days.

(21) Appl. No.: 16/162,006

(22) Filed: Oct. 16, 2018

(65) Prior Publication Data

US 2019/0139221 A1 May 9, 2019

Related U.S. Application Data

(60) Provisional application No. 62/572,738, filed on Oct. 16, 2017.

(51) Int. Cl.
*G06K 9/00* (2006.01)
*G06T 7/00* (2017.01)
(Continued)

(52) U.S. Cl.
CPC .......... *G06T 7/0014* (2013.01); *A61B 5/0261* (2013.01); *A61B 5/1455* (2013.01);
(Continued)

(58) Field of Classification Search
CPC . G06T 2207/10101; G06T 2207/30101; G06T 2207/10048; G06T 2207/30104;
(Continued)

(56) References Cited

U.S. PATENT DOCUMENTS

| 534,211 A | 2/1895 | English |
| 2,588,528 A | 3/1952 | Howser |

(Continued)

FOREIGN PATENT DOCUMENTS

| CN | 1108082 A | 9/1995 |
| CN | 1342054 A | 3/2002 |

(Continued)

OTHER PUBLICATIONS

Allen et al., "Computer based system for acquisition and analysis of nailfold capillary images," Medical Image Understanding & Analysis, (2003): 1-4.

(Continued)

*Primary Examiner* — Shervin K Nakhjavan
(74) *Attorney, Agent, or Firm* — Smith Baluch LLP

(57) ABSTRACT

A system for non-invasive hematological measurements includes a platform to receive a body portion of a user and an imaging device to acquire a set of images of a capillary bed in the body portion. For each image, a controller detects one or more capillaries in the body portion of the finger to identify a first set of capillaries by estimating one or more attributes of each capillary (e.g., structural attributes, flow attributes, imaging attributes, or combinations thereof), wherein at least one attribute of each capillary meets a predetermined criterion. The controller also identifies a (Continued)

second set of capillaries from the first set of capillaries such that each capillary of the second set of capillaries is visible in a predetermined number of images of the set of images.

31 Claims, 69 Drawing Sheets
(57 of 69 Drawing Sheet(s) Filed in Color)

(51) Int. Cl.
| | |
|---|---|
| *A61B 5/026* | (2006.01) |
| *A61B 5/00* | (2006.01) |
| *A61B 5/145* | (2006.01) |
| *A61B 5/1455* | (2006.01) |
| *G06K 9/66* | (2006.01) |

(52) U.S. Cl.
CPC .......... *A61B 5/14546* (2013.01); *A61B 5/489* (2013.01); *A61B 5/6826* (2013.01); *A61B 5/7203* (2013.01); *A61B 5/7267* (2013.01); *G06K 9/00885* (2013.01); *G06K 9/66* (2013.01); *A61B 2576/02* (2013.01); *G06K 2009/00932* (2013.01); *G06K 2009/00939* (2013.01); *G06T 2207/10016* (2013.01); *G06T 2207/10152* (2013.01); *G06T 2207/20081* (2013.01); *G06T 2207/20084* (2013.01); *G06T 2207/30101* (2013.01); *Y02A 90/10* (2018.01)

(58) Field of Classification Search
CPC ............. G06T 2207/30201; G06T 7/11; A61B 1/0009; A61B 3/1241; A61B 2576/02; A61B 1/05; A61B 5/0077; A61B 5/6826; A61B 1/0684; A61B 2562/164; A61B 5/0022; A61B 5/0059; A61B 5/0205; A61B 5/489; A61B 5/742; A61B 1/0005; A61B 5/004; A61B 5/0066; A61B 5/1128; A61B 5/1172; A61B 10/00; A61B 18/14; A61B 18/203; A61B 5/0013; A61B 5/0064; A61B 5/02241; A61B 5/02438; A61B 5/1114; A61B 5/7271; A61B 6/463; A61B 6/5217; A61B 6/541; A61B 8/4488; A61B 8/5223; G01N 15/1475; G01N 2015/0073; G01N 2015/0084; G06K 2009/00939; G06K 2209/05; G06K 9/00885; G06K 2009/00932; G06K 9/00013; G06K 9/0004; G06K 9/2054; G06K 9/46; G06K 9/6257
See application file for complete search history.

(56) References Cited

U.S. PATENT DOCUMENTS

| | | | |
|---|---|---|---|
| 4,998,533 | A | 3/1991 | Winkelman |
| 5,068,536 | A | 11/1991 | Rosenthal |
| 5,077,476 | A | 12/1991 | Rosenthal |
| 5,086,229 | A | 2/1992 | Rosenthal et al. |
| 5,204,532 | A | 4/1993 | Rosenthal |
| 5,218,207 | A | 6/1993 | Rosenthal |
| 5,237,178 | A | 8/1993 | Rosenthal et al. |
| 5,362,966 | A | 11/1994 | Rosenthal et al. |
| 5,365,066 | A | 11/1994 | Krueger, Jr. et al. |
| 5,436,455 | A | 7/1995 | Rosenthal et al. |
| 5,452,717 | A | 9/1995 | Branigan et al. |
| 5,582,705 | A | 12/1996 | Yeung et al. |
| 5,596,987 | A | 1/1997 | Chance |
| 5,598,842 | A | 2/1997 | Ishihara et al. |
| 5,676,143 | A | 10/1997 | Simonsen et al. |
| 5,782,757 | A | 7/1998 | Diab et al. |
| 5,855,212 | A | 1/1999 | Walker |
| 5,926,261 | A | 7/1999 | Hoshino |
| 5,934,278 | A * | 8/1999 | Ishihara ............... A61B 5/1455 600/476 |
| 5,983,120 | A | 11/1999 | Groner et al. |
| 6,041,247 | A | 3/2000 | Weckstrom et al. |
| 6,213,952 | B1 | 4/2001 | Finarov et al. |
| 6,246,786 | B1 | 6/2001 | Nishikiori et al. |
| 6,358,208 | B1 | 3/2002 | Lang et al. |
| 6,424,851 | B1 | 7/2002 | Berman et al. |
| 6,687,521 | B2 | 2/2004 | Sato et al. |
| 8,858,429 | B2 * | 10/2014 | Mizuyoshi ............. A61B 1/063 600/180 |
| 9,984,277 | B2 | 5/2018 | Castro-Gonzalez et al. |
| 2001/0002431 | A1 | 5/2001 | Gurley |
| 2005/0209514 | A1 | 9/2005 | Oshima et al. |
| 2005/0268369 | A1 | 12/2005 | Santiago |
| 2006/0060770 | A1 | 3/2006 | Page et al. |
| 2006/0161063 | A1 | 7/2006 | Shau |
| 2007/0092115 | A1 | 4/2007 | Usher et al. |
| 2007/0116345 | A1 | 5/2007 | Peterson et al. |
| 2007/0161877 | A1 | 7/2007 | Arai et al. |
| 2007/0260129 | A1 | 11/2007 | Chin |
| 2008/0079723 | A1 | 4/2008 | Hanson et al. |
| 2009/0005693 | A1 | 1/2009 | Brauner et al. |
| 2009/0018417 | A1 | 1/2009 | Wang |
| 2009/0093970 | A1 | 4/2009 | Lewy et al. |
| 2010/0104169 | A1 | 4/2010 | Yamada |
| 2010/0254582 | A1 | 10/2010 | Liu et al. |
| 2010/0292629 | A1 | 11/2010 | Dacey, Jr. et al. |
| 2010/0324407 | A1 * | 12/2010 | Pichon ............. A61B 17/12022 600/407 |
| 2011/0134426 | A1 | 6/2011 | Kaduchak et al. |
| 2011/0275908 | A1 | 11/2011 | Baumann |
| 2012/0269420 | A1 | 10/2012 | Najarian et al. |
| 2013/0011055 | A1 | 1/2013 | You et al. |
| 2013/0216119 | A1 * | 8/2013 | Baumgart .............. A61B 6/504 382/134 |
| 2013/0235949 | A1 | 9/2013 | Jeckeln |
| 2014/0038206 | A1 | 2/2014 | Holmes et al. |
| 2014/0085482 | A1 | 3/2014 | Teich et al. |
| 2014/0092377 | A1 | 4/2014 | Liu et al. |
| 2014/0160481 | A1 | 6/2014 | Ahner et al. |
| 2014/0232869 | A1 | 8/2014 | May et al. |
| 2014/0240667 | A1 | 8/2014 | Uji et al. |
| 2014/0249784 | A1 | 9/2014 | Sankaran et al. |
| 2014/0273076 | A1 | 9/2014 | Adams et al. |
| 2015/0169641 | A1 | 6/2015 | Alldrin et al. |
| 2016/0148038 | A1 * | 5/2016 | Castro-Gonzalez ........................ A61B 5/6826 382/134 |
| 2017/0367459 | A1 | 12/2017 | Yamasaki |
| 2018/0012359 | A1 * | 1/2018 | Prentasic ............. G06N 3/0454 |
| 2018/0098683 | A1 * | 4/2018 | Kikuchi ................ A61B 5/7289 |
| 2018/0211380 | A1 * | 7/2018 | Tandon ................ G06K 9/6271 |
| 2019/0139221 | A1 | 5/2019 | Castro-Gonzalez et al. |
| 2021/0022665 | A1 | 1/2021 | Butterworth |

FOREIGN PATENT DOCUMENTS

| | | |
|---|---|---|
| CN | 1399131 A | 2/2003 |
| EP | 0641542 A2 | 3/1995 |
| KR | 20130028484 A | 3/2013 |
| KR | 101273692 B1 | 6/2013 |
| WO | 0027276 A1 | 5/2000 |
| WO | 0122741 A2 | 3/2001 |
| WO | 2017127732 A1 | 7/2017 |

OTHER PUBLICATIONS

Anderson et al., "Computerized nailfold video capillaroscopy—a new tool for assessment of raynaud's phenomenon," J. Rheumatology 32.5 (2005): 841-848.
Brown et al., "Rigidity of Circulating Lymphocytes is Primarily Conferred by Vimentin Intermediate Filaments", The Journal of Immunology, 166.11 (2001): 6640-6646.
Delgado-Gonzalo et al., "Spline-based framework for interactive segmentation in biomedical imaging," IRBM 34.3 (2013): 235-243.

(56) References Cited

OTHER PUBLICATIONS

Eden et al., "An automated method for analysis of flow characteristics of circulating particles from in vivo video microscopy," IEEE Transactions on Medical Imaging 24.8 (2005): 1011-1024.
Etehad Tavakol, Mahnaz, et al. "Nailfold capillaroscopy in rheumatic diseases: which parameters should be evaluated?." BioMed research international 2015 (2015).
Golan et al., "Noninvasive imaging of flowing blood cells using label-free spectrally encoded flow cytometry," Biomed Opt Express 3.6 (2012): 1455-1464.
Hofstee et al., "A multicentre study on the reliability of qualitative and quantitative nail-fold videocapillaroscopy assessment," Rheumatology (2011): ker403.
Hollis et al., "Comparison of venous and capillary differential leukocyte counts using a standard hematology analyzer and a novel microfluidic impedance cytometer," PloS One 7.9 (2012): e43702.
Huang et al., "'A SR-based radon transform to extract weak lines from noise images," in Proceedings Int Conf on Image Processing, Barcelona, Spain 1 (2003): 849-852.
International Search Report and Written Opinion issued for PCT/US15/62487, dated Feb. 5, 2016.
Kaur et al., "Nailfold Capillaryscopy Techniques—A Review," IRACST—IJCSITS 2.2 (2012): 326-331.
MacLennan et al., "Finger-prick blood samples can be used interchangeably with venous samples for CD4 cell counting indicating their potential for use in CD4 rapid tests," AIDS 21.12 (2007): 1643-1645.
Mugii, et a., "Reduced red blood cell velocity in nail-fold capillaries as a sensitive and specific indicator of microcirculation injury in systemic sclerosis," Rheumatology 48.6 (2009): 696-703.
Rao et al., "Evaluation of a new point of care automated complete blood count (CBC) analyzer in various clinical settings," Clinica Chimica Acta 389.1-2 (2008): 120-125.
Riva et al., "Blue field entoptic phenomenon and blood velocity in the retinal capillaries," JOSA 70.10 (1980): 1234-1238.
Russcher et al., "Evaluation of the HemoCue WBC DIFF system for point-of-care counting of total and differential white cells in pediatric samples," Ned Tijdschr Klin Chem Labgeneesk 38.3 (2013): 140-141.
Uji et al., "The source of moving particles in parafoveal capillaries detected by adaptive optics scanning laser ophthalmoscopy," Investigative Ophthalmology & Visual Science 53.1 (2012): 171-178.
Winkelman et al., "Noninvasive Blood Cell Measurements by Imaging of the Microcirculation," Am J Clin Pathol 113 (2000): 479-483.
Yap et al., "Mechanical deformation of neutrophils into narrow channels induces pseudopod projection and changes in biomechanical properties", Journal of Applied Physiology 98.5 (2005): 1930-1939.
Bezemer et al., "Validation of near-infrared laser speckle imaging for assessing microvascular (re) perfusion." Microvascular research 79.2 (2010): 139-143.
Cheng et al., "Non-invasive assessment of microvascular and endothelial function " JoVE (Journal of Visualized Experiments) 71 (2013): e50008. 8 pages.
Dobbe et al., "Measurement of functional microcirculatory geometry and velocity distributions using automated image analysis." Medical & biological engineering & computing 46.7 (2008): 659-670.
Extended European Search Report in European Patent Application No. 18867626.6 dated May 19, 2021, 8 pages.
Mengko et al., "Morphological characterization of nailfold capillaries" 2016 International Seminar on Intelligent Technology and Its Applications (ISITIA). IEEE, 2016. 6 pages.
Bourquard, Aurélien, et al. "Analysis of white blood cell dynamics in nailfold capillaries." 2015 37th Annual International Conference of the IEEE Engineering in Medicine and Biology Society (EMBC). IEEE, 2015, 11 pages.
CS&E PCT Collaborative Search and Examination Pilot Upload Peer Contribution mailed Mar. 7, 2019, 58 pages.
Deneux et al., "A processing work-flow for measuring erythrocytes velocity in extended vascular networks from wide field high-resolution optical imaging data." Neuroimage 59.3 (2012): 2569-2588.
Doshi et al., "Computer-Aided Analysis of Nailfold Capillaroscopy Images." Handbook of Research on Trends in the Diagnosis and Treatment of Chronic Conditions. IGI Global, 2016. 146-158.
Drew, Patrick J., et al. "Rapid determination of particle velocity from space-time images using the Radon transform." Journal of computational neuroscience 29.1-2 (2010): 5-11.
Extended European Search Report in European Patent Application No. 15862463.5 dated Sep. 11, 2018, 7 pages.
International Search Report and Written Opinion in International Patent Application No. PCT/US18/56100 dated Mar. 7, 2019, 16 pages.
Kim et al., "An original approach for quantification of blood vessels on the whole tumour section." Analytical cellular pathology 25.2 (2003): 63-75.
Moeini, Mohammad, et al. "Effects of anesthesia on the cerebral capillary blood flow in young and old mice." Multiphoton Microscopy in the Biomedical Sciences XV. vol. 9329. International Society for Optics and Photonics, 2015, 7 pages.
Sainthillier et al.,"Skin capillary network recognition and analysis by means of neural algorithms." Skin Research and Technology 11.1 (2005): 9-16.
Wu, Chih-Chieh, et al. "Accuracy evaluation of RBC velocity measurement in nail-fold capillaries." Microvascular research 81.3 (2011): 252-260.
Bourquard et al., "Non-invasive detection of severe neutropenia in chemotherapy patients by optical imaging of nailfold microcirculation." Scientific reports 8.1 (2018): 1-12.
Grassi et al., "Capillaroscopy: questions and answers." Clinical rheumatology 26.12 (2007): 2009. 8 pages.
Hofstee et al., "A multicentre study on the reliability of qualitative and quantitative nail-fold videocapillaroscopy assessment." Rheumatology 51.4 (2012): 749-755.
Hou et al., "A computerized system of nail-fold capillaroscopy for dry eye disease diagnosis." Multidimensional Systems and Signal Processing 23.4 (2012): 515-524.
International Search Report and Written Opinion in International Patent Application No. PCT/US2020/034483 dated Aug. 4, 2020, 11 pages.
Lefford et al., "Nailfold capillary microscopy in connective tissue disease: a quantitative morphological analysis." Annals of the rheumatic diseases 45.9 (1986): 741-749.
McKay et al., "Imaging human blood cells in vivo with oblique back-illumination capillaroscopy." Biomedical Optics Express 11.5 (2020): 2373-2382.
McKay et al., "Visualization of blood cell contrast in nailfold capillaries with high-speed reverse lens mobile phone microscopy." Biomedical Optics Express 11.4 (2020): 2268-2276.
Mercer et al., "Quantitative nailfold video capillaroscopy in patients with idiopathic inflammatory myopathy." Rheumatology 49.9 (2010): 1699-1705.
Murray et al., "The influence of measurement location on reliability of quantitative nailfold videocapillaroscopy in patients with SSc." Rheumatology 51.7 (2012): 1323-1330.
Nagy et al., "Nailfold digital capillaroscopy in 447 patients with connective tissue disease and Raynaud's disease." Journal of the European Academy of Dermatology and Venereology 18.1 (2004): 62-68.
Pablo-Trinidad et al., "Automated detection of neutropenia using noninvasive video microscopy of superficial capillaries." American journal of hematology 94.8 (2019): E219. 4 pages.
Pennarola et al.,"Nailfold capillroscopic monitoring as preventive medicine in subjects exposed to ionising radiation." 11th International Congress of the international Radiation Protection Association. 2004. 6 pages.
Reif et al., "Label-free imaging of blood vessel morphology with capillary resolution using optical microangiography." Quantitative imaging in medicine and surgery 2.3 (2012): 207. 6 pages.

(56) References Cited

OTHER PUBLICATIONS

Shore, "Capillaroscopy and the measurement of capillary pressure." British journal of clinical pharmacology 50.6 (2000): 501-513.

* cited by examiner

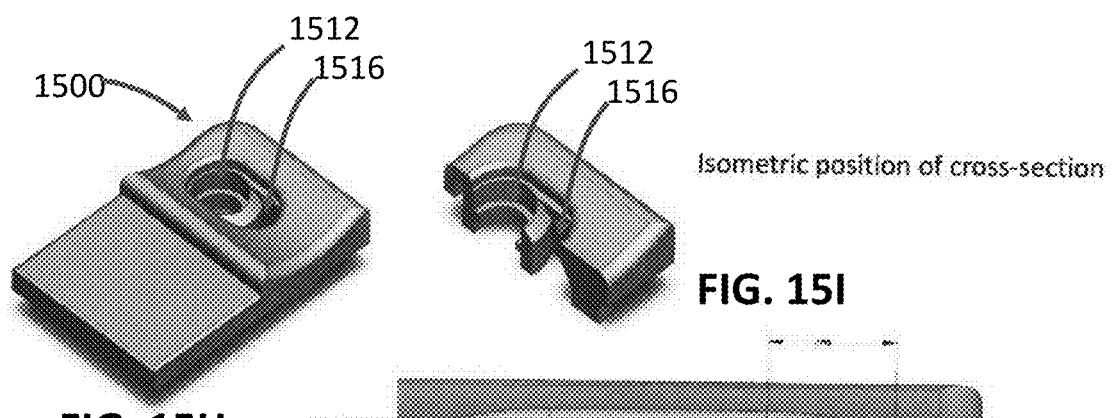
FIG. 15H
FIG. 15I
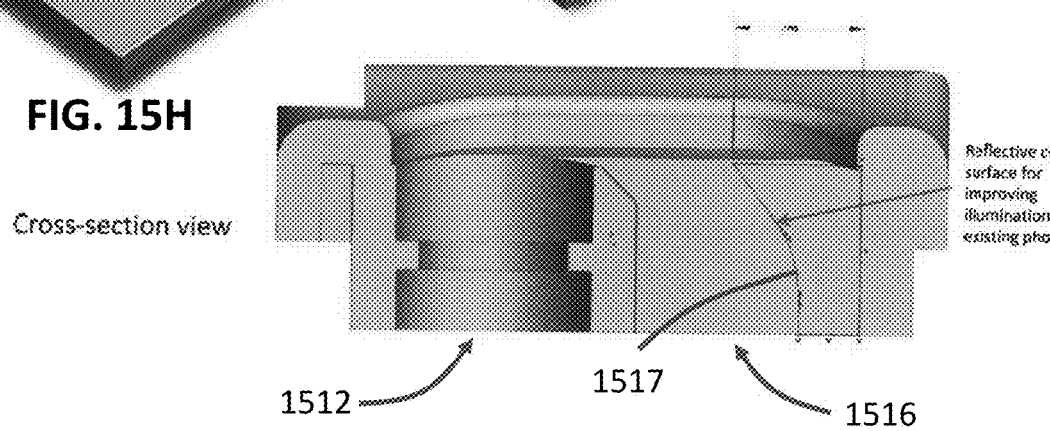
FIG. 15J

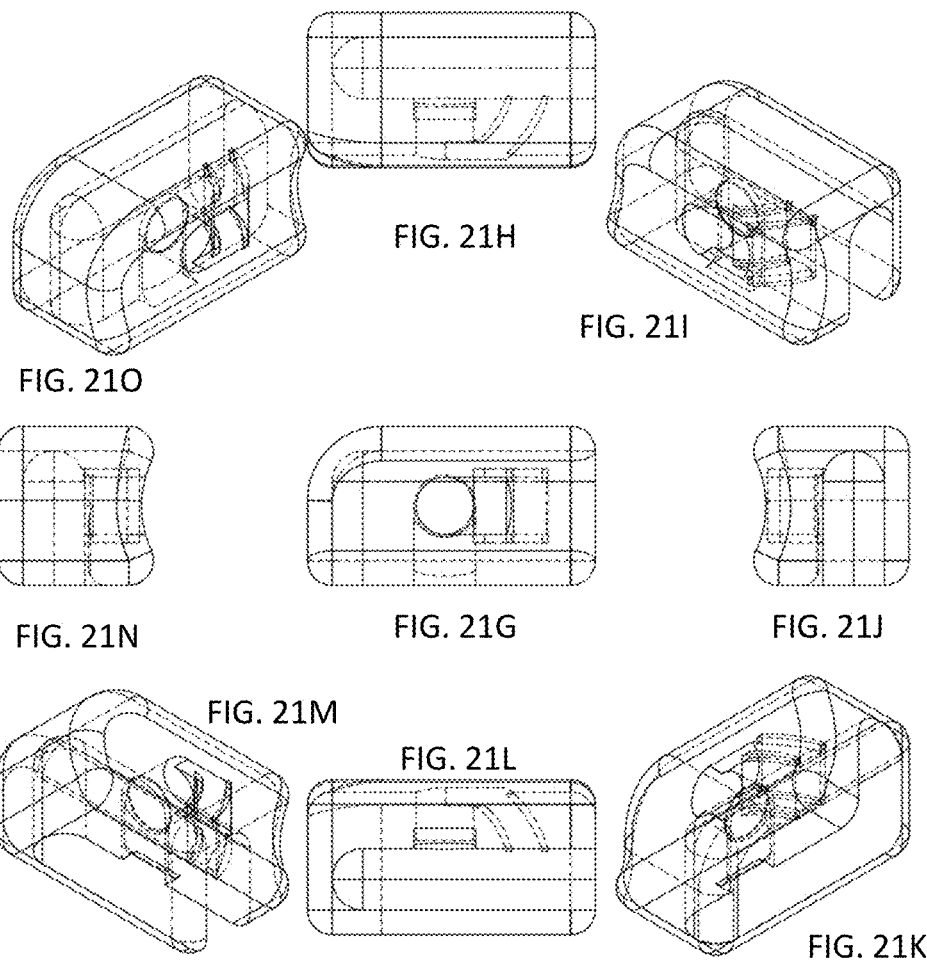

Raw Capillary Video frame $f_0+k$    frame $f_0+2k$    frame $f_0+3k$    frame $f_0+4k$

Preprocessed Capillary Video

Time Signal at Individual Pixel Locations

Averaged Time Signal

3000

Acquiring a set of images of at least a nailfold portion of a finger of a user
3100

Detecting, in each image of the set of images, one or more capillaries in the nailfold portion of the finger to identify a first set of capillaries across the set of images, the detecting including estimating one or more attributes of each capillary of the first set of capillaries, the one or more attributes including one or more structural attributes, one or more imaging attributes, or combinations thereof, such that a first attribute of the one or more attributes of each capillary of the first set of capillaries meets a predetermined criterion for the first attribute
3200

Identifying a second set of capillaries from the first set of capillaries such that each capillary of the second set of capillaries is visible in a predetermined number of images of the set of images
3300

FIG. 30

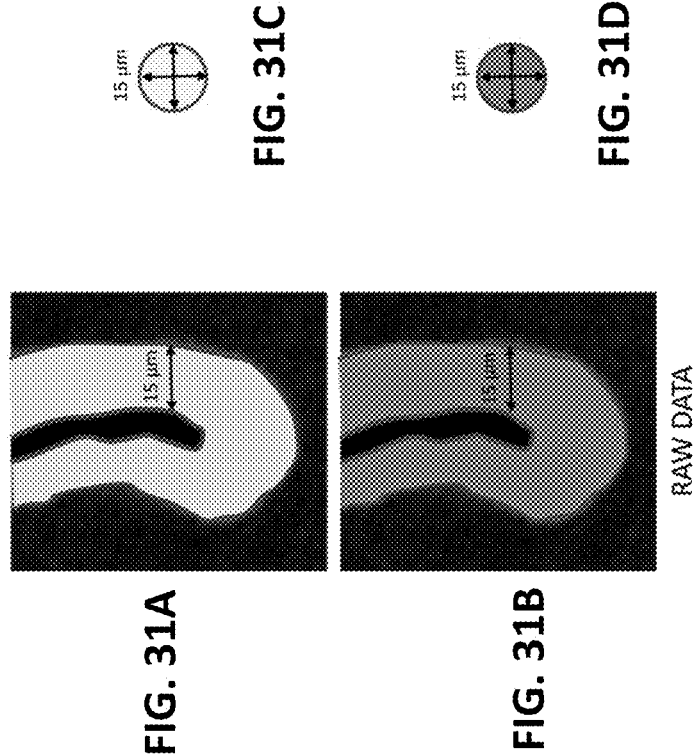

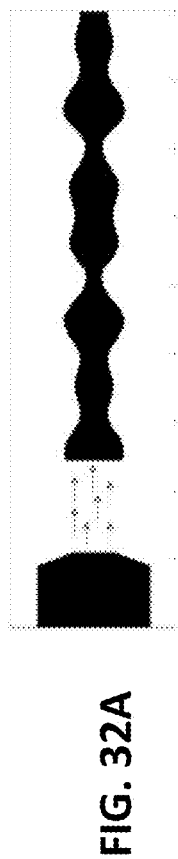
FIG. 32A
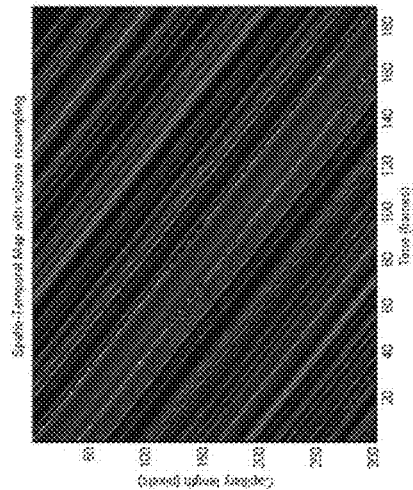
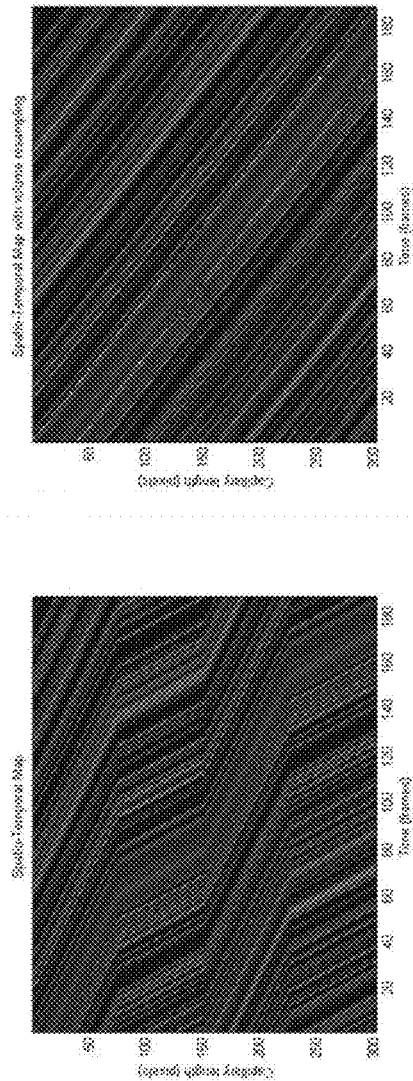
FIG. 32B Spatio-Temporal Map without volume resampling
FIG. 32C Spatio-Temporal Map with volume resampling

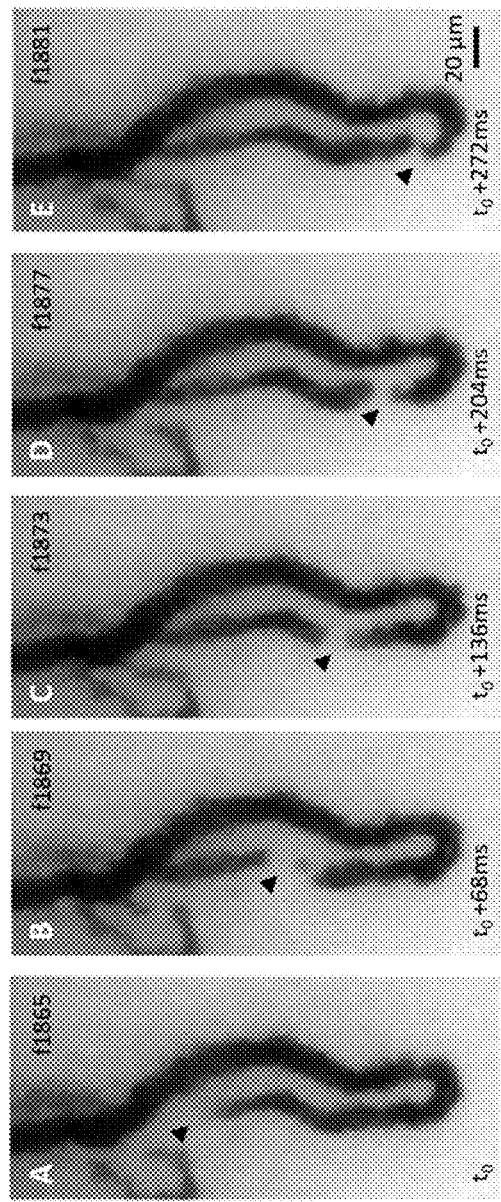

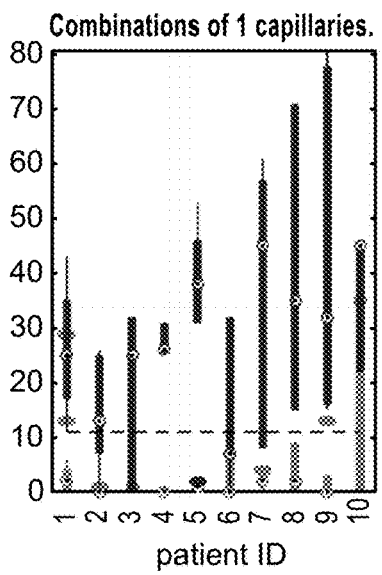
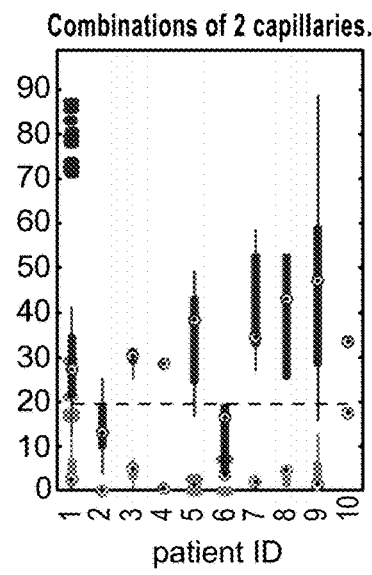
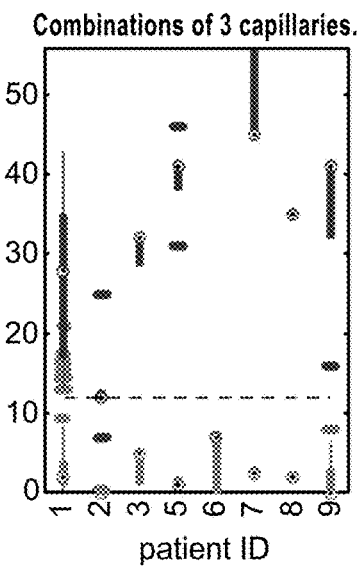
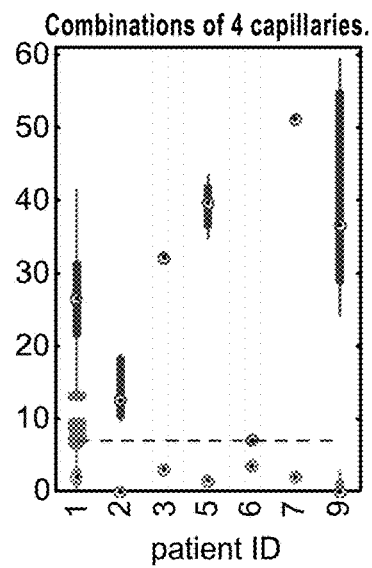
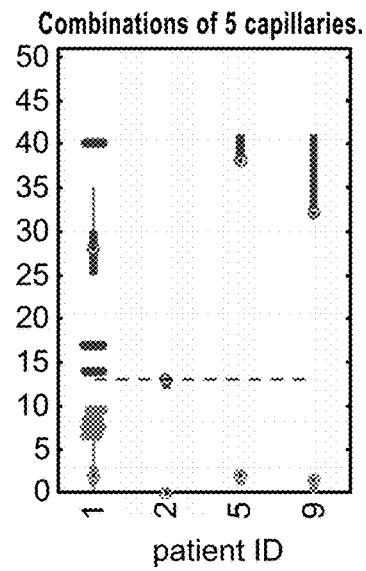
FIG. 44A

SYSTEMS, DEVICES AND METHODS FOR NON-INVASIVE HEMATOLOGICAL MEASUREMENTS

CROSS-REFERENCE TO RELATED APPLICATIONS

This application claims priority to U.S. Provisional Application No. 62/572,738 filed Oct. 16, 2017, titled "DEVICE AND METHODS FOR NON-INVASIVE HEMATOLOGICAL MEASUREMENTS", the entire disclosure of which is hereby incorporated by reference.

STATEMENT OF SUPPORT

This invention was made with government support under Grant No. U54EB015403 awarded by the National Institutes of Health. The Government has certain rights in the invention.

TECHNICAL FIELD

The present disclosure relates generally to systems, apparatus, and methods for analyzing blood cell dynamics and cell population dynamics. More specifically, the present disclosure relates to systems, apparatus, and methods for extracting white blood cell information from non-invasive, in vivo, and/or time-lapse images.

BACKGROUND

White blood cells (WBCs, also referred to as leukocytes or leucocytes) are cells of the immune system that are involved in protecting the body against both infectious disease and foreign invaders. WBCs can exist not only in the blood, but also in the lymphatic system and tissues. Some conditions can trigger a response in the immune system and cause an increase in the number of WBCs (also referred to as WBC count). Other conditions can affect the production of WBCs by the bone marrow or the survival of existing WBCs in the circulation system. Either way, these conditions can cause a change (either an increase or a decrease) of the number of circulating WBCs. Therefore, WBC counts can be a relevant physiological parameter for the diagnosis, monitoring, and treatment of various conditions including, but not limited to, bacterial and viral infections (e.g., pneumonia or meningitis), bone marrow functionality associated with chemotherapy toxicity, and hematologic proliferative processes such as leukemia.

In current clinical practice, most of the tests to derive WBC count are performed with large-scale equipment in central clinical laboratories. Generally, these ex vivo tests are still invasive because blood samples (usually a full vial of blood is needed for each test) are collected from a patient. These blood samples are then transported, queued, and analyzed in laboratory tests, thereby may taking several days to receive any results. This procedure can be burdensome for patients who need regular WBC counts or for patients with emergent conditions as well as their care takers. In addition, due to the ex vivo nature of conventional blood tests, there can be a certain bias of some parameters owing to the inherent differences between the measurements and the true physiological properties.

SUMMARY

A system includes a platform to receive a body portion of a user during use, and an imaging device coupled to the platform and to acquire a set of images of at least a capillary bed of the body portion. The system also includes a controller communicably coupled to the imaging device and to detect, in each image of the set of images, one or more capillaries in the body portion to identify a first set of capillaries across the set of images. The detecting including estimating one or more attributes of each capillary of the first set of capillaries, the one or more attributes including one or more structural attributes, one or more flow attributes, one or more imaging attributes, or combinations thereof. A first attribute of the one or more attributes of each capillary of the first set of capillaries meets a predetermined criterion for the first attribute. The controller also identifies a second set of capillaries from the first set of capillaries such that each capillary of the second set of capillaries is visible in a predetermined number of images of the set of images.

A method including acquiring a set of images of at least a capillary bed of a body portion of a user, and detecting, in each image of the set of images, one or more capillaries in the body portion to identify a first set of capillaries across the set of images. The detecting includes estimating one or more attributes of each capillary of the first set of capillaries, the one or more attributes including one or more structural attributes, one or more flow attributes, one or more imaging attributes, or combinations thereof. A first attribute of the one or more attributes of each capillary of the first set of capillaries meets a predetermined criterion for the first attribute. The method also includes identifying a second set of capillaries from the first set of capillaries such that each capillary of the second set of capillaries is visible in a predetermined number of images of the set of images.

A device including a controller to receive a set of images of a capillary bed of a body portion of a user, and to detect, in each image of the set of images, one or more capillaries in the body portion of the finger to identify a first set of capillaries across the set of images. The detecting includes estimating one or more attributes of each capillary of the first set of capillaries, the one or more attributes including one or more structural attributes, one or more flow attributes, one or more imaging attributes, or combinations thereof. A first attribute of the one or more attributes of each capillary of the first set of capillaries meets a predetermined criterion for the first attribute. The controller also identifies a second set of capillaries from the first set of capillaries such that each capillary of the second set of capillaries is visible in a predetermined number of images of the set of images. The controller also detects, for the set of images and in the second set of capillaries, a set of cellular events, each cellular event of the set of cellular events associated with passage of a white blood cell in a capillary of the second set of capillaries. The controller also estimates an event count for the second set of capillaries based on the set of cellular events.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 4A is a plot of a cubic spline interpolation of x-coordinates. FIG. 4B is a plot of a cubic spline interpolation of y-coordinates.

FIG. 6A shows an example spatiotemporal profile g" of capillary 500 from FIG. 5. FIG. 6B illustrates spatiotemporal trajectories corresponding to WBC events by dashed lines spanning the 2D intensity plot.

FIG. 8A shows the Radon transform g of the map in FIG. 7, according to some embodiments. FIG. 8B shows the spatiotemporal profile in the Radon domain with identified peaks highlighted in circles.

FIG. 9A shows experimental results of WBC events occurring inside capillary 500. FIG. 9B shows experimental results of WBC events occurring inside capillary 510 shown in FIG. 5.

FIG. 11A is a side view of the system, and FIG. 11B is a top view of the system, according to some embodiments. FIG. 11C is a system for analyzing blood cell dynamics, according to other embodiments.

FIG. 12A is a side view of the system. FIG. 12B is a top view of the system.

FIG. 14A shows a finger holder coupled to an imager. FIG. 14B shows an imager and a finger holder de-coupled. FIG. 14C shows a finger holder when a finger is placed in the finger hole. FIG. 14D shows a system including a finger holder, an imager, and a computer that is connected to the imager.

FIGS. 15A-15J are views of an adapter for capturing images of a nailfold with a smartphone camera for blood cell dynamics analysis in accordance with some embodiments. FIG. 15A is a perspective view of the adapter. FIG. 15B is another perspective view of the adapter to illustrate the structure of a window section. FIG. 15C is a top view of the adapter. FIG. 15D is a side view of the adapter. FIG. 15E is another side view of the adapter. FIG. 15F is a back view of the adapter. FIG. 15G is a front view (the side receiving the finger) of the adapter. FIG. 15H is a perspective view of the adapter illustrating an illumination channel.

FIG. 15I is a perspective cross-sectional view of part of the adapter to illustrate a window and an illumination channel. FIG. 15J is a cross-sectional view of the adapter to illustrate a structure of an illumination channel.

FIG. 17A shows a smartphone with an adapter attached to the smartphone so as to allow image taking of a nailfold according to some embodiments. FIG. 17B shows the smartphone and the adapter when a finger is placed in front of the adapter for imaging.

FIGS. 21A-21F and 21G-21O are images and wireframes, respectively, of a smartphone adapter for capturing images of a nailfold with a smartphone camera for capillaroscopy and hematology analysis in accordance with some embodiments. FIG. 21A is a first view of an adapter for capturing images of a nailfold with a smartphone camera. FIG. 21B is another view of the adapter attached to a smartphone. FIG. 21C is yet another view of the adapter to a smartphone. FIG. 21D is yet another view of the adapter to a smartphone. FIG. 21E is yet another view of the adapter to a smartphone. FIG. 21F is yet another view of the adapter, shown here unattached. FIG. 21G is a wireframe view of the adapter. FIG. 21H is another wireframe view of the adapter. FIG. 21I is yet another wireframe view of the adapter. FIG. 21J is another wireframe view of the adapter. FIG. 21K is another wireframe view of the adapter. FIG. 21L is another wireframe view of the adapter. FIG. 21M is another wireframe view of the adapter. FIG. 21N is another wireframe view of the adapter. FIG. 21O is another wireframe view of the adapter.

In FIG. 22A, shows index matched fluid disposed on the surface of a nail fold of a user. FIG. 22B is a view of the smartphone positioned over the finger. FIG. 22C is another view of the smartphone positioned over the finger. FIG. 22D is yet another view of the smartphone positioned over the finger.

FIG. 24A illustrates capillary tracking criteria, with the black bars=capillary segments used to compute the cell count/Leuko index. The id is selected if the amounts of appearances is more than confidence value $\mathbb{C}$=600, (green cases) or discarded if there is more than 3 capillaries selected (red cases). In cases with less than 3 capillaries, the value of $\mathbb{C}$=1. FIG. 24B illustrates capillary tracking criteria, with the capillary segments used to compute the leuko index shown in green and red otherwise.

FIG. 26A illustrates an example of a real averaged time signal produced from one of the analysed capillary videos, shown for its 20 first seconds (Frames 1-1200; see left), with positive-valued peaks associated with the detected events, with a two-second zoom around a single event (Frames 650-769; see right). The zoomed time signal around this example event displays a brightness peak, and also a slight 'dip' of some duration subsequently. FIG. 26B illustrates the expected profile of the averaged time signal around the passage of a single event, this event being associated with the passage of a white blood cell in the capillary (see right). In accordance with the zoomed example of (a), an intensity "dip" is supposed to always occur right after the intensity-peak maximum, due to higher accumulation of red blood cells upstream the white blood cell. FIG. 26C illustrates the expected profile of the averaged time signal around the passage of a plasma gap in the capillary (see right); no dip is supposed to occur in this case as there is no white blood cell and thus no accumulation of red blood cells upstream.

FIG. 27A illustrates an example of event detected on a capillary video by one of the human raters (top row) vs. the neural network (bottom raw) with event marks in blue and white, respectively. FIG. 27B illustrates how true positives (TP), false positives (FP), and false negatives (FN) were evaluated for event detection with respect to a reference. On the right, average F1 score obtained for the 3 raters (red) and for the algorithm (blue) across the 26 capillary videos analyzed, displaying a comparable performance of the neural network according to that metric (F1 isocurves shown in black dashed lines). The expected behavior of the neural network if tuning the event-detection threshold is shown in red dashed line.

FIG. 28A illustrates an initial capillary video with selected frames showing a plasma gap flowing through the capillary, with the direction of flow emphasized by the arrow. FIG. 28B illustrates a pre-processed video with the event appearing as the salient feature in an otherwise dark background. The reference pixel Pref is shown in red, and additional pixels P1 and P2 belonging to the capillary are shown in blue. FIG. 28C illustrates a brightness time signal at the reference-pixel location, at P1, and at P2, revealing the effect of the event (green highlight) on the measured brightness as peaks. FIG. 28D illustrates a final time signal obtained as the average between time signals at individual pixel locations, following their alignment with the reference time signal of Pref; the threshold level used for counting is shown as a vertical blue line.

FIG. 29A illustrates a box plot showing the classification of raw videos associated with baseline states, or ANC>500 (blue) vs. raw videos associated with severe-neutropenic states (ANC<500). FIG. 29B illustrates a ROC curve associated with the classification (AUC=0.96).

FIG. 30 is a flowchart of a method for non-invasive hematological measurements, according to some embodiments.

FIGS. 31A-31F illustrate a method of estimating blood volume based on analysis of pixel-intensity values. FIG. 31A shows an image of a capillary section. FIG. 31B shows another image of the capillary sections, where the pixel value is FIG. 31A is greater than the pixel value in FIG. 31B (i.e. FIG. 31A is brighter). FIG. 31C is a reconstructed capillary cross section of the capillary section in FIG. 31A. FIG. 31D is a reconstructed capillary cross section of the capillary section in FIG. 31B. FIG. 31E shows a reconstructed capillary cross section of the capillary section in FIG. 31A, using the method based on pixel intensity analysis. FIG. 31F shows a reconstructed capillary cross section of the capillary section in FIG. 31B, using the method based on pixel intensity analysis.

FIGS. 32A-32C illustrate a method of volume resampling of a capillary profile. FIG. 32A is a representation of a capillary having a constant blood flow speed but varying diameters along the capillary length. FIG. 32B illustrates a spatio-temporal map representing the gray-scale values (color map from blue—dark— to red—bright—) along the linear capillary length (y-axis) across time (x-axis). FIG. 32C illustrates a spatio-temporal map acquired using volume resampling and the map is shown with the capillary length coordinates (y-axis) as a function of the cumulative capillary volume at each cross-section in FIG. 32A.

FIG. 34A shows the distribution of the time of arrival (TOA) between gaps in a sample with 5,500 WBC/μL. FIG. 34B shows the distribution of TOA between gaps in a sample with 100 WBC WBC/μL.

FIG. 35A illustrates a rendered 3D model of the apparatus employed to record microscopy videos of the microcirculation in nailfold capillaries of patients. FIG. 35B illustrates that patients place their ring finger in a 3D-printed holder. FIG. 35C shows that the finger is placed in such a way that illumination and imaging is directed at the nailfold area.

FIG. 37A shows an image taken with baseline neutrophil concentration (i.e., greater than 1,500/µL). FIG. 37B shows an image taken with when the patient had severe neutropenia (neutrophils concentration less than 500/µL).

FIGS. 38A-38E illustrate an example of optical gap flowing in a capillary. FIG. 38A illustrates the optical gap in a first location in a capillary. FIG. 38B illustrates the optical gap in another location in the capillary. FIG. 38C illustrates the optical gap in yet another location in the capillary. FIG. 38D illustrates the optical gap in yet another location in the capillary. FIG. 38E illustrates the optical gap in yet another location in the capillary.

FIG. 39A shows a capillary-video frame (indexed at top right) with cross-shaped event marks from rater 1 (blue), 2 (green) and 3 (yellow). FIG. 39B shows another capillary-video frame. FIG. 39C shows yet another capillary-video frame. FIG. 39D shows aggregated positions of all event marks from all three raters. FIG. 39E shows an ST map displaying the recorded brightness levels along the segmented capillary length (vertical axis) as a function of time (horizontal axis) for a 1.7-second interval around the event of interest.

FIGS. 44A and 44B show discrimination between baseline and severe neutropenia using capillary aggregates. FIG. 44A shows the number of event counts resulting from integrating N=1, 2, 3, 4, 5 capillaries per patient. FIG. 44B shows the ROC curves for classification of baseline vs. severe neutropenia based on integrating N=1, 2, 3, 4, 5 capillaries per patient.

FIG. 45A shows capillary from a patient. FIG. 45B shows the same capillary with supervised segmentation (red). The scale bar is 20 µm. FIG. 45C shows the separations between arterial limb (green), venous limb (blue), and loop (red) of the capillary can be defined on a case-to-case basis for visualization.

FIG. 48A shows a ST map for a baseline patient. FIG. 48B shows a ST map for a patient with severe neutropenia.

FIG. 61A illustrates classification area-under-the-curve (AUC) as a function of video segment duration[s], with video segment(s) beginning at the very start of the full video. The classification performance is seen to remain optimal and equal to the one based on full 1-min videos for durations of at least 29 seconds, i.e., approximately half the original 1-minute duration. FIG. 61B illustrates classification AUC when using different 29-second video segments when varying the starting time of each video segment in the full 1-minute video; the near-constancy of the resulting AUC values demonstrates the stability of the classification results.

DETAILED DESCRIPTION

Following below are more detailed descriptions of various concepts related to, and implementations of, systems, devices and methods for non-invasive hematological measurements. It should be appreciated that various concepts introduced above and discussed in greater detail below may be implemented in numerous ways. Examples of specific implementations and applications are provided primarily for illustrative purposes to enable those skilled in the art to practice the implementations and alternatives apparent to those skilled in the art.

The figures and example implementations described below are not meant to limit the scope of the present implementations to a single embodiment. Other implementations are possible by way of interchange of some or all of the described or illustrated elements. Moreover, where certain elements of the disclosed example implementations may be partially or fully implemented using known components, in some instances only those portions of such known components that are necessary for an understanding of the present implementations are described, and detailed descriptions of other portions of such known components are omitted so as not to obscure the present implementations.

In view of the challenges with conventional blood tests as discussed above, the Inventors have recognized and appreciated various advantages of non-invasive and in vivo techniques to derive WBC counts. These non-invasive and in vivo techniques allow more frequent monitoring, fewer visits to clinics, and more ready access to testing in areas lacking proper laboratory facilities or reagent supplies.

Non-invasive WBC count techniques that exploit the optical properties of WBCs may be used to observe the WBCs as gaps in nailfold capillaries, retinal capillaries, or moving particles in oral mucosa capillaries. However, specialized and/or non-portable devices (e.g., adaptive optics and confocal microscopy) may be required to derive WBC counts. Optical devices referred to as capillaroscopes may be used to acquire optical images of the morphology of nailfold capillaries and diagnose rheumatological diseases; however, the acquired images require time-consuming analysis by trained human reviewers.

Overview of Non-Invasive and In Vivo Analysis of Blood Cell Dynamics

Figure 1:
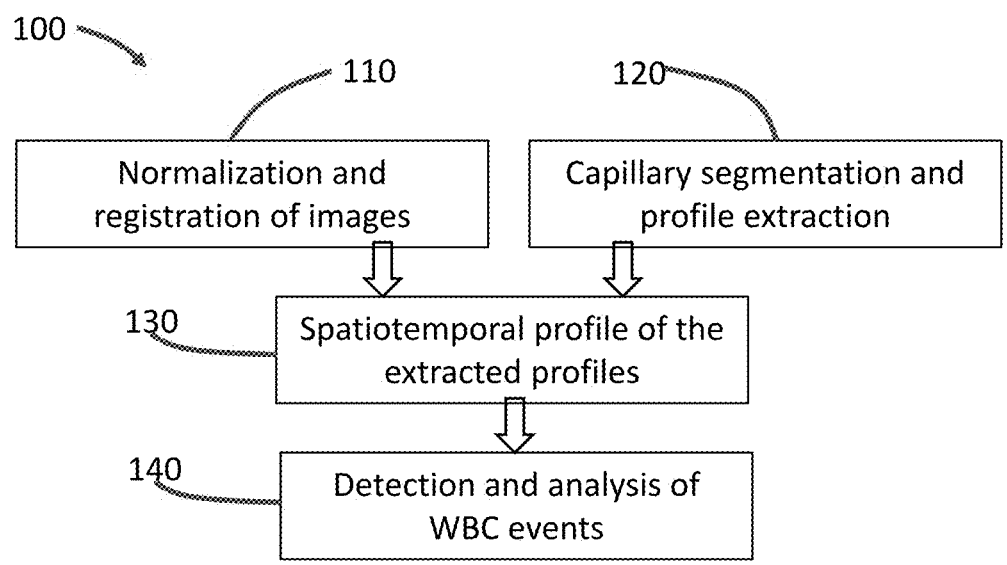
FIG. 1 is a flow chart illustrating methods of analyzing blood cell dynamics in accordance with some embodiments.

FIG. 1 is a flow chart illustrating non-invasive and in vivo methods of analyzing blood cell dynamics according to some embodiments, including but not limited to, detecting a number of WBCs passing through a given capillary over a time period, the speed of one or more of the WBCs flowing through the capillary, and the total number of WBC events per µL. In some embodiment, some or all aspects of the method 100 can be implemented by one or more of the systems, apparatuses, and devices as described herein such as, for example, the system 2300 and/or the device 2340, as described in greater detail with respect to FIG. 23.

More specifically, method 100 illustrated in FIG. 1 includes step 110, at which source image(s) of a subject that contains capillaries are normalized and/or registered. Normalization (also referred to as contrast stretching, histogram stretching, or dynamic arrange expansion) of source images may change the range of pixel intensity values so as to, for example, increase the contrast of images. Registration of source images may align the source images such that same pixel locations on different images correspond to same physical locations on the subject. In some embodiments, the source images are taken within a finite time span, during which the camera, the subject, or both, may be moving. Image registration may address such movements. In image registration, one of the images (e.g., the first image in the sequence, the last image in the sequence, or the image that might have the desired field of view) may be used as a reference image, and the other images in the sequence may be compared to the reference image to make corrections. Corrections may be made to maximize certain image similarity measures that quantify the similarity between the reference image and the other images. Examples of image similarity measures include, for example, cross-correlation, mutual information, sum of squared intensity differences, and ratio image uniformity.

At step 120 of method 100, capillary segmentation and/or profile extraction are performed. Capillary segmentation may be used to identify the segments of capillaries in either the original or the registered images (e.g., by identifying the boundaries of the capillary segments). Profile extraction may be used to extract pixel information within the capillary segments for further analysis. Since WBC information is normally contained only in capillaries, it may be helpful to extract pixel information inside the capillary segments and set aside information in other areas in the images. The pixel information to be extracted may include the locations and values (also referred to as intensities) of the pixels inside the capillary segments. The locations of the pixels in each image may be represented in 2D Cartesian coordinates, and the capillaries may be curved. Therefore, it may be helpful to transform the image from the 2D Cartesian coordinate system into a different coordinate system, in which the same points in the same capillary but on different images in the sequence of images have the same coordinates. One example of such a coordinate system is the curvilinear coordinate system, which uses one point in the curved capillary as the origin point and any other point has a one-dimensional (1D) coordinate that is the distance between that point and the origin point.

At step 130 of method 100, profiles extracted from the sequence of images are compiled into a single image (also referred to as spatiotemporal profile) so as to analyze WBC events. Profiles extracted from each image may include information about spatial distribution (i.e., locations) of WBC events or other events of interest. Profiles extracted from different images, taken at different time points, in the sequence of images may include information about WBC events at different time points. Therefore, the spatiotemporal profile, compiled from all of these extracted profiles from the entire sequence of images, may provide rich information relating to both spatial distribution and temporal evolution of WBC events. For example, traces of a particular WBC may be visualized from the spatiotemporal profile. The velocity of a particular WBC flowing in a capillary also may be derived by, for example, taking into account the time lapse between two or more images in the sequence of images.

At step 140 of method 100, the spatiotemporal profile is processed to detect and/or analyze WBC events. In some embodiments, the processing is manual. A user may inspect the spatiotemporal profile and identify a WBC event by, for example, detecting a visual gap (e.g., pixels having higher or lower pixel values compared to surrounding pixels) in the spatiotemporal profile. The user also may derive the motion traces and flow speed from the spatiotemporal profile. In other embodiments, the processing is automatic or semi-automatic. For example, the spatiotemporal profile may be, for example, transformed to the Radon domain. WBC events then may be detected based on local maxima in the Radon domain. Based on the detected WBC events, additional analysis, such as WBC counts and WBC flow speed, may be derived. Furthermore, WBC counts, flow speed, etc., may be used for subsequent diagnosis, monitoring, and/or treatment of diseases or conditions.

According to some embodiments, systems, apparatus, and methods for analysis of blood cell dynamics are based on in vivo images of capillaries without blood drawing or other invasions into a subject's body and also without removing WBCs from their natural environment in the subject's body. In addition, these systems, apparatus, and methods may be used for real-time or substantially real-time results. For example, the processing of the images (from source images to the detection of WBC events and calculation of the WBC counts) may be performed while new images are being taken. WBC events may be monitored to test the response of a subject's body to a medical treatment, thereby providing feedback regarding the efficiency of the treatment. Furthermore, systems, apparatus, and methods here can identify WBC events from relatively low-resolution, low-frame-rate, and noisy source images. For examples, the source images can be frames of a video clip taken by off-the-shelf cameras, cellphone, or other image taking devices.

Methods of Non-Invasive and In Vivo Analysis of Blood Cell Dynamics

Figure 2:
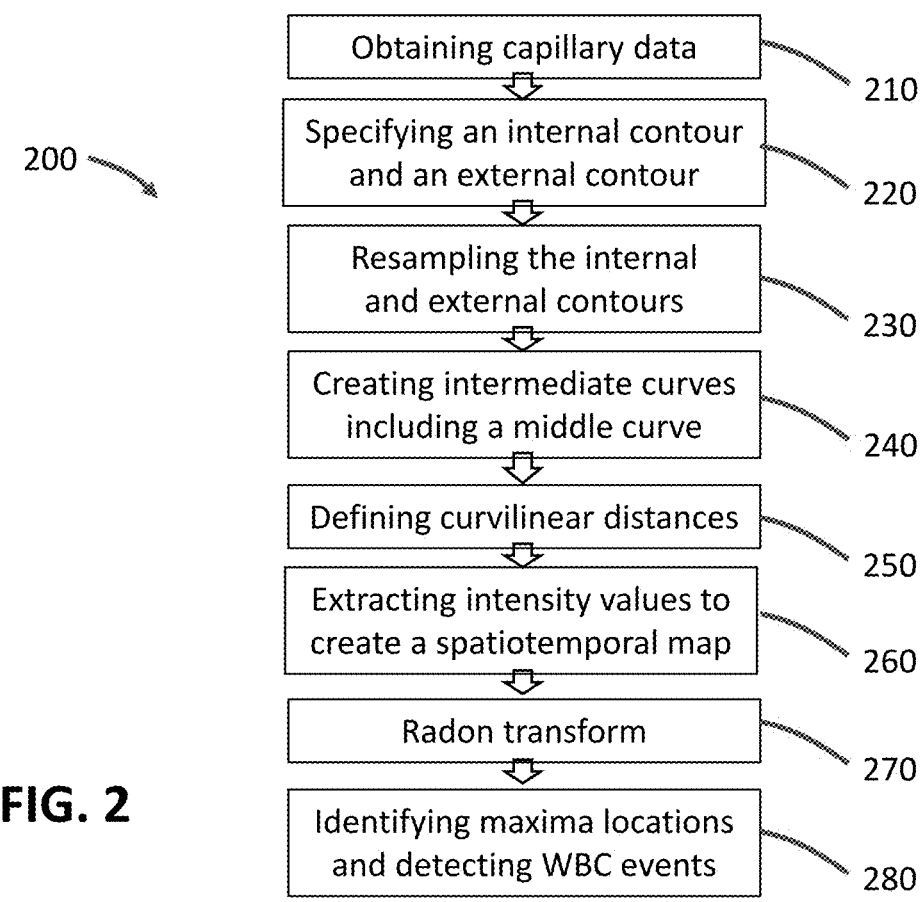
FIG. 2 is a flow chart illustrating methods of analyzing blood cell dynamics using spatiotemporal profiles and Radon transform in accordance with some embodiments.

FIG. 2 is a flow chart illustrating methods of analyzing blood cell dynamics using Radon transforms of spatiotemporal profiles of capillary images according to some embodiments. Method 200 may be used to detect a WBC event from in vivo capillary data associated with a subject. In some embodiment, some or all aspects of the method 200 can be implemented by one or more of the systems, apparatuses, and devices as described herein such as, for example, the system 2300 and/or the device 2340, as described in greater detail with respect to FIG. 23.

At step 210 of method 200, capillary data is non-invasively obtained. The capillary data may include a plurality of images of one or more capillary segments captured over a first time period.

At step 220 of method 200, the contours of the one or more capillary segments in the images are specified. In particular, for each image in the plurality of images, a first set of two-dimensional (2D) coordinates may be specified to correspond to internal contour points of a capillary segment visible in the images. Step 220 also may include specifying a second set of 2D coordinates corresponding to external contour points of the capillary segment. These sets of 2D coordinates in each image may define the boundaries of the capillary segment in the image.

At step 230 of method 200, each of the first set of 2D coordinates and the second set of 2D coordinates are interpolated so as to generate a first set of resampled coordinates and a second set of resampled coordinates, respectively. The interpolation may fill potential gaps between adjacent contour points specified at step 220 and therefore define smoother boundaries of the one or more capillary segments.

At step 240 of method 200, a plurality of intermediate curves are generated based on the first set of resampled coordinates and the second set of resampled coordinates. These intermediate curves may be within the capillary segment defined by the internal contours points and the external contour points. The plurality of intermediate curves may include a middle curve, which may be used to define a plurality of curvilinear distances as in step 250 of method 200.

In step 260 of method 200, a plurality of intensity values are extracted from the plurality of images. Each extracted intensity value corresponds to one of the plurality of images, one of the plurality of intermediate curves, and one of the plurality of curvilinear distances. That is, each extracted intensity value may be indexed by a vector including three values representing (1) a particular image, (2) a particular intermediate curve, and (3) a particular curvilinear distance.

At step 270 of method 200, the extracted intensity values are transformed to the Radon domain. In step 280 of method 200, a plurality of maxima locations in the Radon domain correspond to a flow trajectory inside the capillary such that a visual gap in the flow trajectory inside the capillary indicates a WBC event.

Capillary Data Collection

According to some embodiments, capillary data (e.g., source images) for the analysis of blood cell dynamics may be obtained from various subjects including, but not limited to, humans and other mammals. In some embodiments, capillary data is collected or captured from one or more locations on or in the body of the subject. For example, capillary data may be collected and/or captured from nailfold capillaries, retinal capillaries, and/or oral mucosa capillaries.

Source images may be captured using various methods. For example, source images may include a sequence of images extracted from a video clip. Each image in the sequence of the images may be captured at a different time point such that the analysis of blood cell dynamics may include, for example, the flow speed of WBCs.

In some embodiments, a location on or in the body of the subject is illuminated by pulsed light sources, and source images are captured by a camera synchronized with the pulsed light sources. For example, a location may be illuminated by pulsed lasers of a particular wavelength (e.g., blue light at about 430 nm), at which WBCs (or other objects of interest) have good reflectivity, so as to improve the contrast of the resulting images.

In some embodiments, the source images include one or more color images such that each pixel in the source images include three values corresponding to, for example, the values of the red, green, and blue components, respectively. In some embodiments, the source images include one or more gray-scale images such that each pixel in the source images has a bit depth of, for example, 2, 4, 6, 7, 8, or 10, corresponding to a gray level of 4, 16, 64, 128, 256, and 1024, respectively.

In some embodiments, the capillary data (e.g., obtained at step 210 in FIG. 2) includes a video acquired in 24-bit RGB format from a given subject. In general, video data may be viewed as a three-dimensional stack I of a sequence of image frames represented as $N_h \times N_v \times N_f$, where $N_h$ and $N_v$ are the horizontal and vertical sizes (also referred to as pixel numbers) of each image frame, respectively, and $N_f$ is the total number of frames in the video data. Each pixel in this video data may be represented as I[k, l], which corresponds to an RGB vector (R[k; l], G[k; l], B[k; l]). The indices $k=(k_1, k_2)$ designate the location of a pixel within a certain frame, and l refers to the index of the frame in the plurality of frames included in the video data. R[k; l], G[k; l], and B[k; l] corresponds to the value of red, green, and blue component, respectively, of the pixel I[k, l]. For example, I[(15, 20), 5] points to a pixel located at the fifteenth row and the twentieth column in the fifth frame of the video data.

Figure 3:
FIG. 3 is an example image of a nailfold that can be used in the methods illustrated in FIGS. 1-2 in accordance with some embodiments.

FIG. 3 is an example image of a human nailfold that may be used in the methods described above for the analysis of blood cell dynamics in one or more of the nailfold capillaries. The image is a frame taken from a nailfold capillaroscopy video, which has a frame rate of r frames per second and a camera pixel size of $S_p$ μm. In FIG. 3, the relatively darker U-shaped profiles of capillaries 300 are readily identifiable in the image, despite the presence of white saturated areas 310 associated with non-ideal acquisition conditions.

Capillary Data Preprocessing

Some pre-processing steps of the images in the capillary data may be performed to facilitate subsequent processing and analysis. These pre-processing steps may include image normalization and/or image registration. In some embodiment, some or all aspects of these pre-processing steps can be implemented by one or more of the systems, apparatuses, and devices as described herein such as, for example, the system 2300 and/or the device 2340, as described in greater detail with respect to FIG. 23.

In some embodiments, the capillary data includes one or more grayscale images. Normalization may be used to compress and/or stretch the gray level to a desired range. In some embodiments, the capillary data includes one or more color images. Normalization may be used to convert a color image into a grayscale image before compressing and/or stretching the gray level. The conversion from color images to grayscale images may be achieved via various methods. In one example, the resulting gray level of a color pixel is a sum of the red, green, and blue values in the pixel. In another example, the resulting gray level is the difference between the value of the red component and green component (R-G) so as to emphasize the capillary structures. More sophisticated methods may be employed to calculate the gray level so as to emphasize specific objects of interest (e.g., a WBC or a red blood cell). For example, particular weighted averages of red, green, and blue components may be calculated, or in other types of channel conversion that are non-linear (e.g., RGB to HSV (Hue, Saturation, Value) conversion).

In some embodiments, image registration includes one or more intensity-based methods, which compare intensity patterns in images via correlation metrics. Intensity-based methods can register entire images or sub-images. If sub-images are registered, centers of corresponding sub-images may be treated as corresponding feature points.

In some embodiments, image registration includes one or more feature-based methods, which find correspondence between image features such as points, lines, and contours. Feature-based methods can establish a correspondence between one or more distinct points in an image. Knowing the correspondence between these distinct points in images, a geometrical transformation may be determined to map the target image to other images, thereby establishing point-by-point correspondence between a reference image and other images.

In some embodiments, the capillary data includes a 24-bit RGB format video, including frames like the image in FIG. 3. In these embodiments, stack I may be converted into a single-channel version $I_n$ that can be suitably exploited for further profile segmentation and analysis. The scalar-valued stack $I_n[k; l]$ may be obtained by first averaging the RGB channels of I for each pixel point ("point-wise") and then normalizing the resulting intensities. The normalization may be performed such that the mean and standard deviation of the intensity values of $I_n$ over every given frame l is 0 and 1, respectively. The frames constituting In may be registered to, for example, compensate for camera movements. The frame registration may be achieved by applying respective corrective shifts to each frame l>1 of $I_n$, that is, using the first image (l=1) as reference.

More specifically and first, a point-wise operation may be performed to obtain temporary stack $$I'[k;l]=R[k;l]-G[k;l], \quad (1)$$

for all k and l, i.e., $k_1$=1, 2, . . . , $N_h$; $k_2$=1, 2, . . . , $N_v$; and $k_3$=1, 2, . . . , $N_f$. This operation emphasizes capillary-like structures while discarding surrounding artefacts.

Second, binary-thresholded stack $I_t'$ may be obtained using a threshold value $\tau_c$ that is specified for every separate frame of the sequence, the value of which may be determined either experimentally, using a priori information existing in the images (e.g., total brightness, contrast, gray-scale variance, skewness, etc.), or through feature learning from a training dataset. In this step, the pixel value at a location [k; l] in the temporary stack I'[k; l] is set to zero if I'[k; l] is smaller than $\tau_c$ and is set to one if I'[k; l] is equal to or greater than $\tau_c$, that is:

$$I_t[k;l]=0 \text{ if } I'[k;l]<\tau_c \quad (2)$$

and $$I_t[k;l]=1 \text{ if } I'[k;l]\geq\tau_c \quad (3)$$

Third, a 2D registered stack $I_r$ is calculated such that the applied corrective shifts can maximize the correlation (i.e., the normalized scalar product) between $I_t'$ [k; l] and $I_t'$ [k; l], for l>1.

Capillary Profile Segmentation

Step 220 of method 200 in FIG. 2 is performed to achieve capillary profile segmentation, i.e., identify segments of capillaries in the images, in accordance with some embodiments. In some embodiments, segmentation is performed on the source images (with or without pre-processing). In some embodiments, segmentation is performed on normalized and/or registered images. In some embodiments, segmentation is performed on source images after some other processing, such as noise filtering and/or contrast improvements intended to emphasize capillary structures.

In some embodiments, capillary segmentation is manual. A user may draw lines along the boundaries of the capillaries visible in the images. For example, step 220 may be performed by a user. The user may mark some internal contour points and external contour points on an image, after which a computer may retrieve the 2D coordinates of these marked internal and external contour points for further processing (e.g., resamples at step 230).

In some embodiments, capillary segmentation is automated or semi-automated using methods such as thresholding and/or edge detection. Artificial intelligence methods may be used to train a computer-based pattern recognition model. In one example, a pattern recognition model may be based on historical images of capillaries such that the pattern recognition model can recognize similar capillary structures when a new image is provided. In another example, a pattern recognition model may be based on one or more capillary structures in one portion of an image such that the pattern recognition model can recognize similar capillary structures in other portions of the image.

In some embodiments, capillary segmentation may involve a hybrid approach, in which a user makes some initial and rough indications of the boundaries of capillaries and a computer-based program refines the initial indications using interpolation (e.g., linear interpolation, polynomial interpolation, or spline interpolation), curve fitting (e.g., using linear or nonlinear regression), and/or extrapolation (e.g., using linear extrapolation, polynomial extrapolation, conic extrapolation, or French extrapolation).

In some embodiments, segmentation of each capillary is semi-automated with minimal user-defined 2D coordinates. For example, a user may define two sets of 2D coordinates, $P_{int}[j]$ and $P_{ext}[j]$, with j=1, 2, . . . , $N_p$, that follow the internal and external capillary boundaries as defined on the first frame of the stack I. Here, j is the index of the jth point on the contour, and $N_p$ is the total number of points specified by the user in each contour (internal or external). The total number of specified point $N_p$ can be dependent on several factors including, but not limited to, the complexity of the capillary boundaries and the length of the capillaries. Fewer points can be specified for straight capillaries or straight portions of capillaries, compared to capillaries with sharp turns. In some embodiments, the number of specified points $N_p$ may range from about 3 points to about 20 points. In some embodiments, the number of specified point $N_p$ may be about 5 points to about 10 points.

The value of the point $P_{int}[j]$ or $P_{ext}[j]$ includes a vector that designates the location of this point in the 3D stack I or $I_r$. For example, $P_{int}[5]$ refers to the fifth point on the internal contour of a capillary. The value of $P_{int}[5]$ may be, for example (20, 30), which indicates the 2D location of the point on the image, i.e., twentieth row and thirtieth column. After acquiring the 2D location of this point on the curve, the pixel value (or intensity) of the pixel may be retrieved from the image stack I or $I_r$. In this way, index on the curve (j), pixel location (k), and pixel value are correlated to each other in a one-to-one manner.

Resampling of Capillary Contour Points

The contour points specified, for example, at step 220 of method 200, are usually sparse and may only mark, for example, certain characteristic points on the internal and external boundaries of capillaries (e.g., starting point, ending point, or turning points). Therefore, at step 230 of method 200, the specified internal and external contour points are resampled so as to further refine the boundaries for further processing in accordance with some embodiments.

At least one of three methods and/or a combination thereof may be used to resample the specified contour points. In some embodiments, interpolation (e.g., linear interpolation, polynomial interpolation, or spline interpolation) is used to generate new data points between two adjacent specified points so as to fill the gap. In some embodiments, curve fitting (e.g., using linear or nonlinear regression) is used to fit the specified contour points to a curve, which generally has an analytic expression and therefore can contain an arbitrary number of data points for further processing. In some embodiments, extrapolation (e.g., using linear extrapolation, polynomial extrapolation, conic extrapolation, or French extrapolation) is employed to generate projected points beyond the curve section defined by the specified contour points. In further embodiments, a combination of two or more these methods is used.

In some embodiments, a denser set of points $P'_{int}$ and $P'_{ext}$ is generated using cubic-spline interpolation of the original points with a resampling factor $\alpha$. The total number of contour points after resampling is therefore $\alpha(N_p-1)+1$, where $N_p$ is the number of contour points specified. The resampling factor $\alpha$ may be at least partially dependent on the desired resolution of the resampled contours, i.e., the distance between two adjacent resampled contour points (also referred to as point spacing). For example, if WBC events are to be detected, it is preferred to set the point spacing smaller than the size of WBCs so as to resolve each WBC in subsequent processing. In some embodiments, the point spacing may be substantially similar to the pixel size in the source images in the capillary data.

Figure 4A:
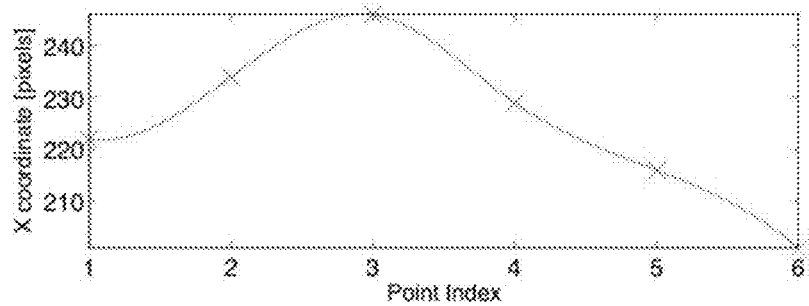
FIGS. 4A-4B are plots of cubic spline interpolation that can be used in the methods illustrated in FIGS. 1-2 for resampling user-specified contour points of capillaries in accordance with some embodiments.
Figure 4B:
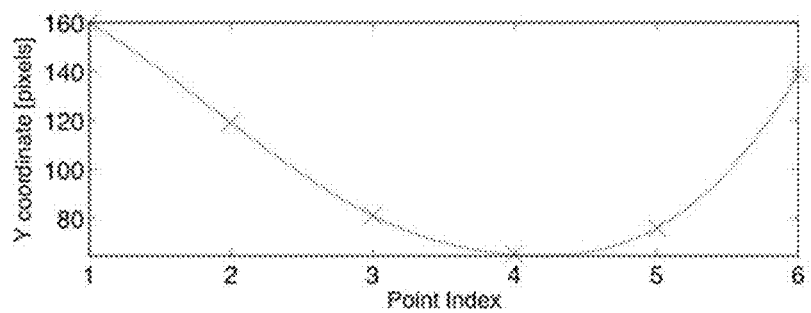

In some embodiments, resampling is performed directly on the 2D coordinates specified at step 220. For example, 2D spline (also referred to as bicubic interpolation) may be used to resample the specified contour points. In some embodiments, the point-resampling operation at step 230 includes separate 1D resampling of the corresponding horizontal and vertical coordinate sequences (also referred to as row and column sequences, respectively). FIG. 4A is a plot of a cubic spline interpolation of x-coordinates, and FIG. 4B is a plot of a cubic spline interpolation of y-coordinates. In FIGS. 4A-4B, the contour points specified at step 220 are marked as crosses (e.g., cross 400) and the resampled contour points connect the crosses. Note that the resampled data points are so numerous that they appear as continuous curves (e.g., apparent curve 410).

Definition of Intermediate Curves and Curvilinear Distances

At step 240 of method 200, a series of intermediate curves are defined between the internal contour and the external contour of each identified capillary according to some embodiments. In some embodiments, the series of intermediate curves are evenly distributed in the space defined by the internal and external contours. In some embodiments, the distribution of intermediate curves is uneven. For example, the central portion of the capillary may have a higher density of intermediate curves compared to an edge portion of the capillary.

In some embodiments, a series of $N_c$ intermediate curves $P'_m[j]$ is generated by linear combinations of the form:

$$tP'_{int}+(1-t)P'ext \quad (4)$$

where m=1, 2, ..., $N_c$, $N_c$ is the total number of intermediate curves; j=1, 2, ..., $\alpha(N_p-1)+1$, $\alpha(N_p-1)+1$ is the total number of data points in each curve; and $t=(m-1)/(N_c-1)$ is a linear combination coefficient.

The total number of intermediate curves $N_c$ may be dependent on the desired resolution of the collection of intermediate curves, i.e., the distance between two adjacent intermediate curves (also referred to as curve spacing). For example, if WBC events are to be detected, the curve spacing may be set smaller than the size of WBCs so as to resolve each WBC in subsequent processing. In some embodiments, the curve spacing may be substantially similar to the pixel size in the source images in the capillary data.

The resampling of contour points at step 230 may be regarded as improving the longitudinal resolution (i.e., the resolution along the direction of the capillary) from specified contour points at step 220. The creation of intermediate curves, on the other hand, may be regarded as improving the lateral resolution (i.e., the resolution along the cross-section of the capillary) based on two boundaries (i.e., the internal and external contours) of the capillary.

In some embodiments, step 230 is performed before step 240 such that intermediate curves can be created based on the resampled contour points acquired at step 230. In some embodiments, step 240 is performed before step 230. For example, a series of intermediate points may be created between one user-specified point on the internal contour and one user-specified point on the external contour so as to fill gaps along the cross-section of the capillary. The same step may be performed for each pair of user-specified points, thereby generating a series of sets of intermediate contour points between the internal contour points and the external contour points. Then a resampling step, like the one at step 230, may be performed for each set of intermediate contour points to string together the intermediate contour points, thereby generating a series of intermediate curves.

At step 240, a middle curve $P'_{mid}$ may be defined as:

$$P'_{mid}=\tfrac{1}{2}P'_{int}+\tfrac{1}{2}P'ext \quad (5)$$

This middle curve $P'_{mid}$ may be used to define curvilinear distances. Curvilinear distance may be defined as the Euclidian norm between each point in $P'_{mid}[j]$ with respect to the starting point $P'_{mid}[1]$. In some embodiments, for simplicity, the jth data points on different intermediate curves $P'm[j]$ are assigned the same curvilinear distances as $P'_{mid}[j]$.

Figure 5:
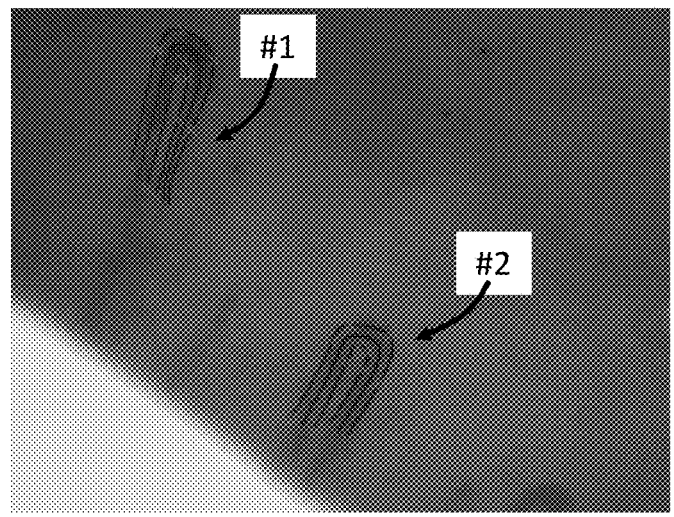
FIG. 5 is an image of a nailfold including two capillaries, user-specified contour points, and resampled contour curves in accordance with some embodiments.

FIG. 5 is a normalized and registered image frame $I_r$ from a video clip including capillary 500 and capillary 510. Both capillaries are highlighted in the processed image along with the corresponding user-defined contour points (shown as crosses) and interpolated points (shown as curves) that follow the internal and external curves of each profile. The middle curve $P'_{mid}$ from which the curvilinear distances are computed is also shown. Note that the user has specified only six points and yet the resampled curves already appear to be in good agreement with the actual boundaries of the two capillaries.

Intensity Profile Extraction

At step 260 of method 200, the intensities of the pixels (i.e., pixel values) within the capillary segments are extracted as a function of curvilinear distance so as to form a spatiotemporal profile $f[j; m; l]$, wherein j is the curvilinear index (the jth point on certain curve), m is the curve index (the mth curve in the plurality of curves including the internal boundary, the external boundary, and the intermediate curves generated in between), and l is the frame index (the lth image in a sequence of images). More specifically, each $P'm[j]$ on $I_r$ is associated with an intensity value. In some embodiments, bilinear interpolation is used to compute the resulting intensities $f[j; m; l]$ with sub-pixel precision at given curvilinear index j, curve m, and frame l.

In some embodiments, given $f[j; m; l]$, the average of the capillary intensities of all curves can be computed for every frame and curvilinear distance so as to generate an averaged spatiotemporal profile $f[j; l]$ (i.e., averaged over all m from 1 to $N_c$). As an analogy, this averaging step can be regarded as collapsing all capillary curves (internal contour, external contour, and intermediate curves) into a single curve.

In some embodiments, the averaged spatiotemporal profile $f[j; l]$ is resampled to generate a resampled spatiotemporal profile $g[j; l]$, which contains the same number of samples as $f[j; l]$ but with equidistant curvilinear spacing. The resampling may be performed using linear interpolation.

Spatiotemporal Profile Analysis

The profile $g[j; l]$ may include an intensity profile evolving as a function of time for each point j along the curvilinear distance of each capillary. This profile can exhibit correlations in space and time, which may be extracted to overcome possible challenges in analyzing noisy source images taken at relatively low-frame-rate and/or with low-resolution.

In some embodiments, to emphasize the intensity variations created by WBC events, a median-normalized version of g is computed. More specifically, the medians of the time-varying intensity lines of $g[j; l]$ may be first set to zero at every curvilinear coordinate j. Then the same operation may be performed column-wise at every frame l. To reduce noise, the contrast-normalized profile g' may be filtered along the time axis with a symmetric and unit-sum rectangle function of size σ, which yields g". The filtering operation may be performed through convolution with said rectangle function.

Figure 6A:
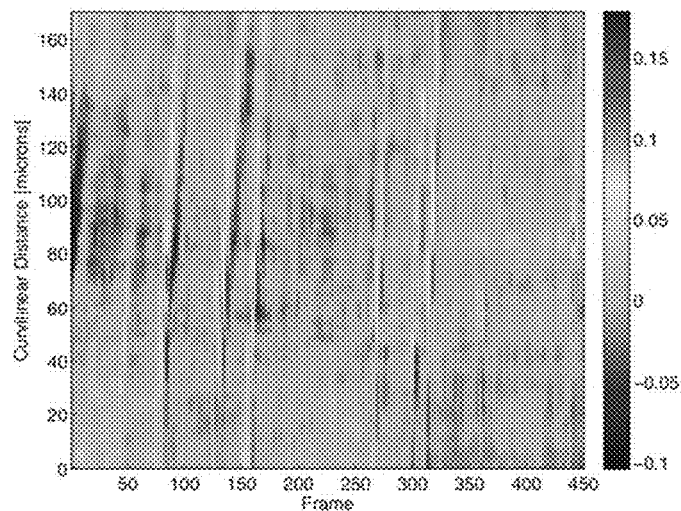
FIGS. 6A-6B are representations of spatiotemporal profiles extracted from the two capillaries shown in FIG. 5 in accordance with some embodiments.
Figure 6B:
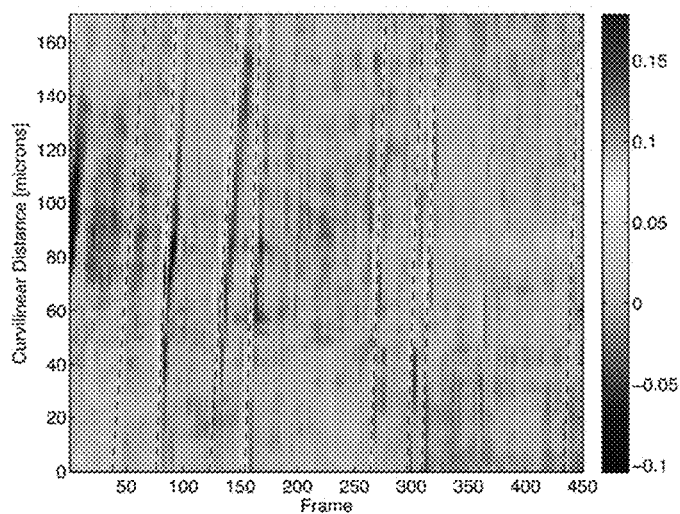

FIG. 6A shows an example spatiotemporal profile g" of capillary 500 from FIG. 5. The spatiotemporal profile g" was generated based on the original spatiotemporal profile $f[j; m; l]$, after averaging over all m from 1 to $N_c$ (achieve $f[j; l]$), resampling to have equidistant curvilinear spacing (achieve $g[j; l]$), median-normalization (to achieve g' [j; 1]), and filtering (to achieve g"[j; l]). On the spatiotemporal profile shown in FIG. 6A, spatiotemporal trajectories corresponding to WBC events can be identified. FIG. 6B illustrates these trajectories by dashed lines spanning the 2D intensity plot. The slope of each line may be associated with the average speed of the corresponding WBC event inside the capillary. Therefore, the spatiotemporal profiles like those shown in FIGS. 6A-6B already provide important information about WBC events in the capillaries such as the number of events and the flow speed. This information may be extracted manually, automatically, or semi-automatically using the methods described above.

Radon Transform

At step 270 of method 200, a Radon transform is performed on the spatiotemporal profiles generated in step 260 according to some embodiments. The Radon transform maps 2D lines to peaks located at particular positions so as to identify events and their associated parameters. Event detection using Radon transform is not only convenient but robust to noise.

Without being bound by any particular theory or mode of operation, given a continuous 2D image $f(x)$, wherein x is a 2D Cartesian coordinate defined with respect to the center of the image $f(x)$, the Radon transform called $\hat{f}=Rf$ may be defined as $$\hat{f}(\theta, x_1') = \int_{-\infty}^{\infty} f(x_1' \cos\theta - x_2' \sin\theta, x_1' \sin\theta + x_2' \cos\theta) dx_2' \quad (6)$$

where the radial coordinate x' is defined as $x'=[x_1 \cos\theta+x_2 \sin\theta, -x_1 \sin\theta+x_2 \cos\theta]$.

In some embodiments, $f(x)$ is a discrete image, in which case a discrete-domain Radon transform $R^0$ involving a finite amount of radial-coordinate values and of angles in $[0; \pi]$ may be used. The largest radial-coordinate value can correspond to half of the image-diagonal length. The profile in Radon-domain $\hat{g}$ is thus represented as:

$$\hat{q}[k_\theta, k_r] = R^1 g'' \quad (7)$$

The number of angles is denoted by $N_\theta$, the number of radial coordinates $N_r$ being proportional to $(N_f^2+N_{p,i}^2)^{1/2}$, where $N_{p,i}=\alpha(N_p-1)+1$ is the number of interpolated curvilinear points.

Figure 7:
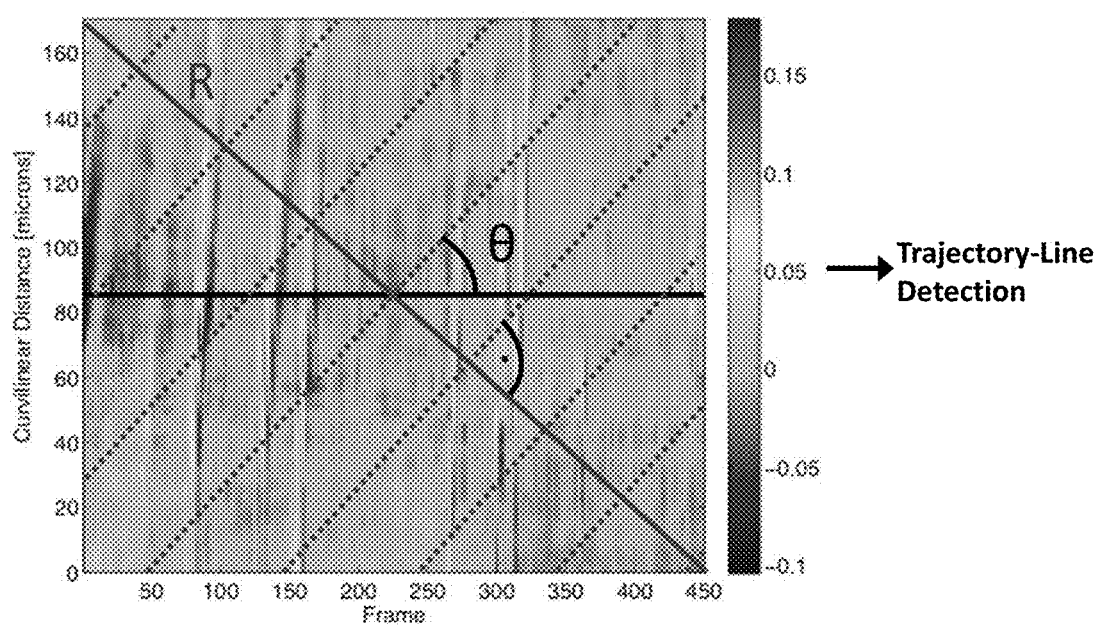
FIG. 7 is a representation of a Radon transform performed on a spatiotemporal profile in accordance with some embodiments.

FIG. 7 illustrates the application of the Radon transform on the spatiotemporal profile shown in FIGS. 6A-6B according to some embodiments. The projection angle θ and radial coordinate R are shown in FIG. 7. The solid arrow illustrates the direction for trajectory-line detection. Considering a predefined set of angles θ and radial coordinates R, the Radon transform computes projections of the spatiotemporal-profile intensities (i.e., the intensities in the non-transformed domain, as shown in FIG. 7). More specifically, the Radon-transformed-domain value (see FIG. 8A) for a given angle θ and radial coordinates R corresponds to the integral of all values (i.e., the intensity values in the non-transformed domain, as shown in FIG. 7) that are found on the line whose counterclockwise angular inclination with respect to the horizontal axis is θ and whose radial coordinate is R.

Figure 8A:
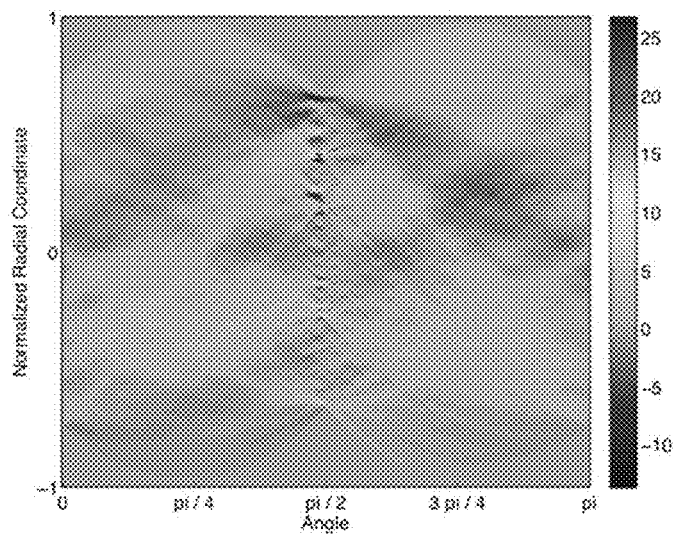
FIGS. 8A-8B are representations of spatiotemporal profiles in the Radon domain with local maxima highlighted to indicate WBC events in accordance with some embodiments.

FIG. 8A shows the Radon transform $\hat{g}$ of the map in FIG. 7 according to some embodiments. The horizontal and vertical axes correspond to the projection angle and to the associated normalized radial coordinate, respectively. In FIG. 8A, several peaks may be readily identified. Each peak may correspond to the linear trajectories observed in the spatial domain (e.g., FIG. 6B). These peaks may be identified and located based on, for example, local-maxima detection within a window of odd pixel size $S_w \times S_w$. In some embodiments, the local-maxima are limited to those greater than a threshold $\tau_m$. In some embodiments, the maxima locations are limited to locations with angular values within the range $[0; \pi/2]$, thereby imposing one single flow direction inside the capillary.

Figure 8B:
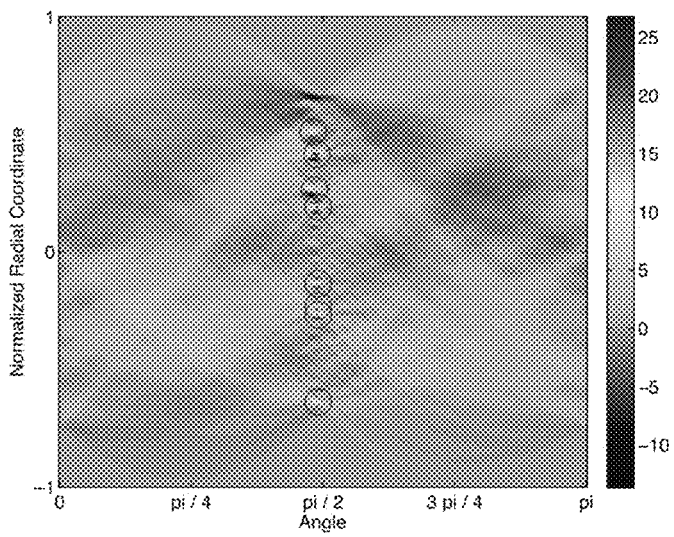

FIG. 8B shows the spatiotemporal profile in the Radon domain with identified peaks highlighted in circles. The original physical time and speed parameters of WBC events in the capillaries may be analytically deduced from the maxima locations based on the known frame rate and pixel size through elementary trigonometric relations. More specifically, the speed is associated with the tangent of the projection angle θ in the Radon domain, and is thus proportional to the vertical slope of the corresponding trajectory line in the aforementioned spatiotemporal profile g". The original physical time is associated with the intersection between said trajectory line and the time axis of said spatiotemporal profile. In some embodiments, the time of each WBC event corresponds to the first frame in which a visual gap appears in the capillary.

Figure 9A:
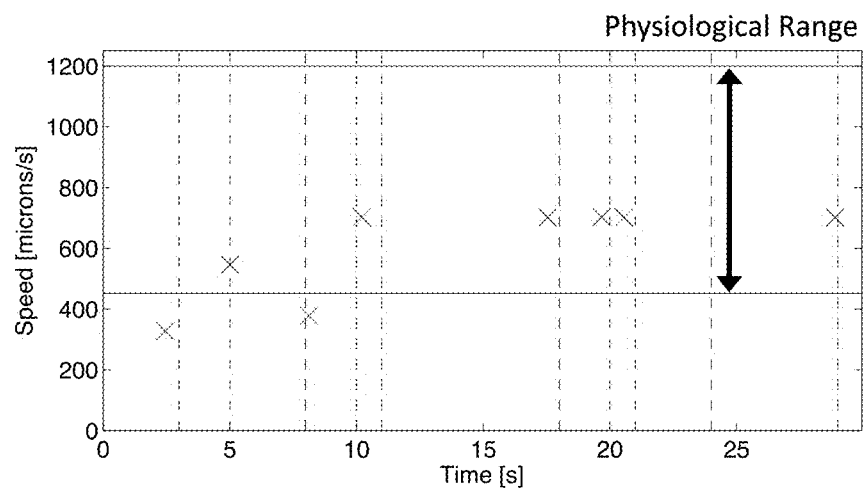
FIGS. 9A-9B are plots representing experimental results of WBC events occurring inside the two capillaries shown in FIG. 5 in accordance with some embodiments.
Figure 9B:
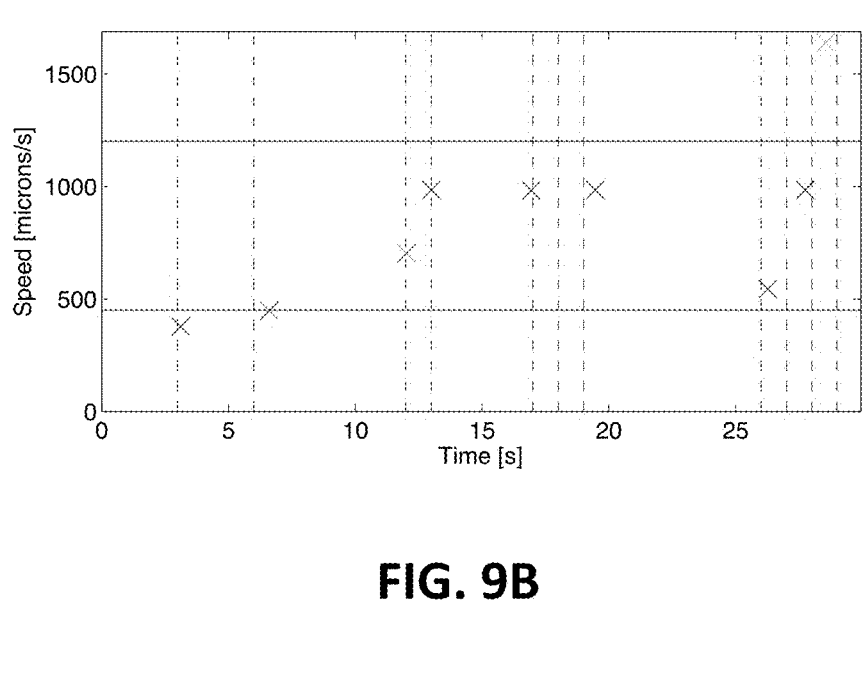

FIG. 9A shows experimental results of WBC events occurring inside capillary 500, and FIG. 9B shows experimental results of WBC events occurring inside capillary 510 shown in FIG. 5 according to some embodiments. The experimental results are compared to manual counts performed by four trained human reviewers. In FIGS. 9A-9B, WBC events detected by the methods described above are marked by a cross, while the event times estimated by a trained human reviewer are denoted by the dashed vertical lines. The horizontal lines represent the maximum and minimum blood-flow-related limits.

The source images are taken from a video clip of a human nailfold. The acquisition parameters are $N_h$=1280, $N_v$=960, $N_f$=450, r=15, and $S_p$=0.65 μm, the duration of the video clip is 30s. The threshold $\tau_c$ is heuristically set to ¾ of the maximum intensity value for each frame l in I'. The amount of user specified curve points is set to $N_p$=6, which can yield accurate segmentations. The number of interpolated curves is set to $N_c$=10, using α=100 for resampling. The size of the filter used for noise reduction is set to σ=3. Finally, the window size and threshold value used for Radon-domain maxima detection are selected as $S_w$=11 and $\tau_m$=7, the number of Radon angles being set to $N_θ$=400.

In FIGS. 9A-9B, more than 80% of the WBC events detected by the methods described above are consistent with those of a trained human reviewer. Missed events may correspond to temporally adjacent visual gaps that can be challenging for automatic methods to resolve due to the poor frame rate.

Figure 10:
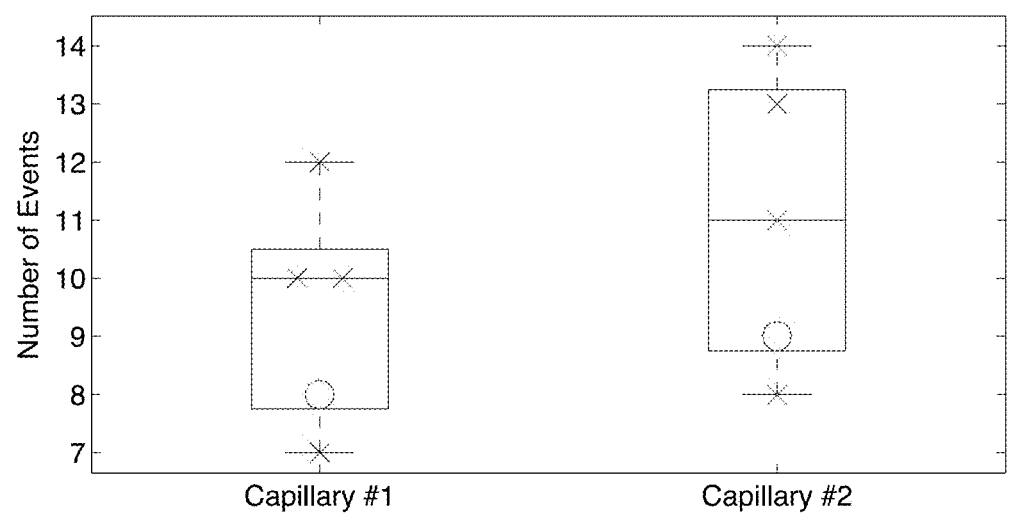
FIG. 10 is a plot comparing WBC events obtained from methods illustrated in FIG. 2 in accordance with some embodiments and WBC events identified by trained human reviewers.

FIG. 10 shows a further comparison between the total WBC event counts obtained from methods described above in accordance with some embodiments and those obtained from all four trained human reviewers. FIG. 10 also shows significant inter-observer variability of manual counts. Each capillary is associated with a box where the central mark is the median. The edges of the box are the 25th and 75th percentiles, and the whiskers extend to the extreme data points. The crosses and the circles denote the counts completed by each of the four trained human reviewers and by the approaches described herein, respectively. The results obtained from the described methods are shown in these box plots to fall within the human inter-rater variability.

The slope of the visual gap trajectories in FIGS. 6A-7B may be employed to compute the speed associated with WBC events for both capillary 500 and capillary 510. The results, represented in FIGS. 9A-9B, fall within the range for blood-flow values of human nailfold capillaries previously reported in literature, that is, about 450 μm/s to about 1200 μm/s.

Interpolated inner and outer capillary curves, $P_{int}[j]$, $P_{ext}[j]$ may be employed to extract the vessel radius r, which corresponded to approximately 7.5 μm for both capillary 500 and capillary 510, a value consistent with previous published data.

Without being bound any particular theory or mode of operation, capillaries may be assumed to have circular cross-sections. Given that the average speed v derived above is approximately 600 μm/s, the total sampled blood volume per second V may be determined as:

$$V = \pi v r^2 = \pi \cdot 600 \frac{\mu m}{s} \cdot (7.5 \; \mu m)^2 \approx 105 \cdot 10^{-6} \frac{\mu L}{s} \quad (8)$$

Given that a healthy WBC range is about 3500 WBCs per 4 to about 9000 WBCs per μL, and given that the duration of the video clip is 30 seconds, a number c of WBC counts may be determined as:

$$c = [3.5, 9] \cdot 10^3 \frac{wbc}{\mu L} 105 \cdot 10^{-6} \frac{\mu L}{s} \cdot 30s \approx [11, 28] wbc \quad (9)$$

which is consistent with the median counts of ten WBC events and eleven WBC events obtained for capillary 500 and capillary 510, respectively.

Figure 11A:
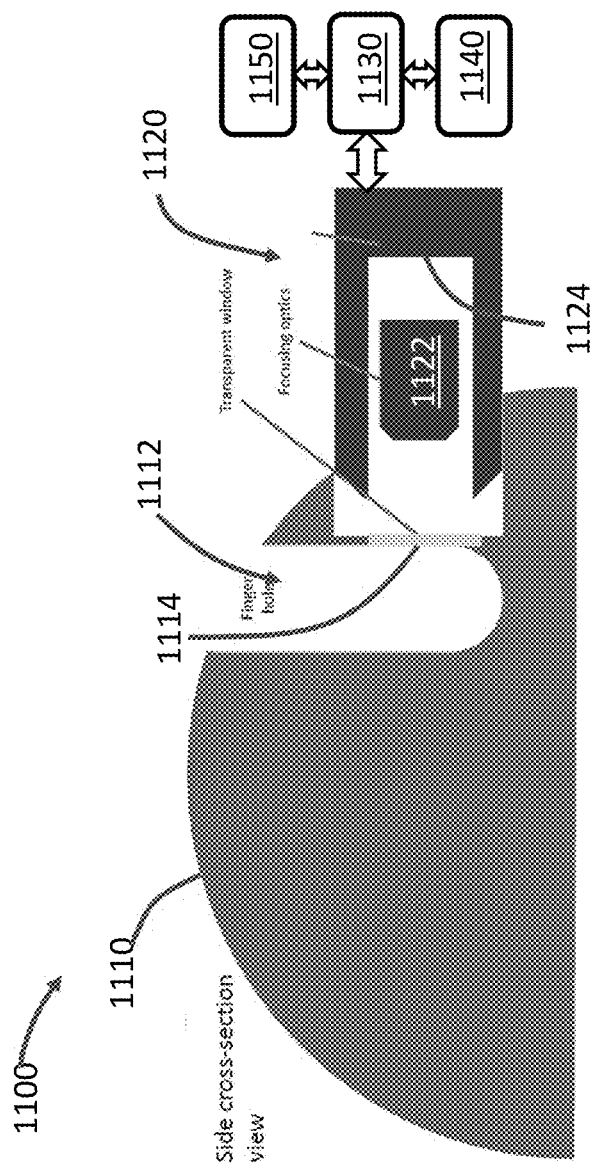
FIGS. 11A-11C are schematics of systems for analyzing blood cell dynamics using a finger holder and an imager in accordance with some embodiments.
Figure 11B:
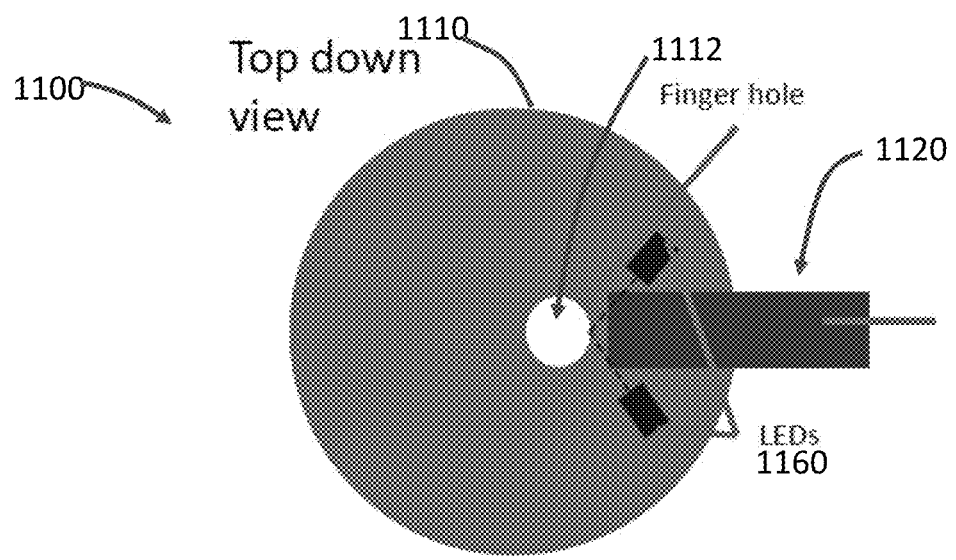

Apparatus and Systems for Non-Invasive and In Vivo Analysis of Blood Cell Dynamics FIGS. 11A-11B are schematics of a system for detecting white blood cell (WBC) events in an in vivo and non-invasive manner according to some embodiments. In some embodiment, some or all aspects of the system of FIGS. 11A-11B can be structurally and/or functionally similar to one or more of the systems, apparatuses, and devices as described herein such as, for example, the system 2300 and/or the device 2340, as described in greater detail with respect to FIG. 23.

FIG. 11A is a side view of the system, and FIG. 11B is a top view of the system. For purposes of illustration, embodiments described herein analyze WBC events in a human nailfold; however, the embodiments may be modified for analysis in other subjects and/or other locations in or on the body of a subject. In FIGS. 11A-11B, system 1100 includes finger holder 1110 having finger hole 1112 to receive at least a portion of a human finger (e.g., a nailfold portion of the finger). Finger holder 1110 is also configured to receive imager 1120, which is in optical communication with the finger received by finger hole 1112 through transparent window 1114 so as to capture images or videos of the finger. The imager further includes focusing optic 1122 to collect light reflected or scattered from the finger and detector 1124 to receive the reflected or scattered light so as to form images of the finger. System 1100 further includes processor 1130 operably coupled to imager 1120 and memory 1140 operably coupled to processor 1130. Memory 1140 is encoded with processor-executable instructions, which, when executed by processor 1130, may perform the methods described above to analyze images received from imager 1120. System 1100 also includes display 1150, which can display the images or videos taken by imager 1120 and/or data associated with WBC events detected by processor 1130.

In some embodiments, finger holder 1110 has an igloo shape (as shown in FIGS. 11A-11B) such that the hand can rest on the dome of the finger holder while a finger in the hand is received by finger hole 1112 for imaging. Finger holder 1110 may have other configurations such as a flat top, a handle configuration (the hand can grip the handle while a finger can be imaged), or any other configurations known in the art.

In some embodiments, system 1100 also includes illumination source 1160 (shown in FIG. 11B) to illuminate the finger and facilitate image taking by imager 120. In some embodiments, illumination source 1160 includes a pair of light emission diodes (LEDs), each of which is disposed on one side of finger hole 1112. In some embodiments, illumination source 1160 is configured to emit monochromatic light. Capillary structures in the finger can have a high reflectivity at the wavelength of the monochromatic light.

Figure 11C:
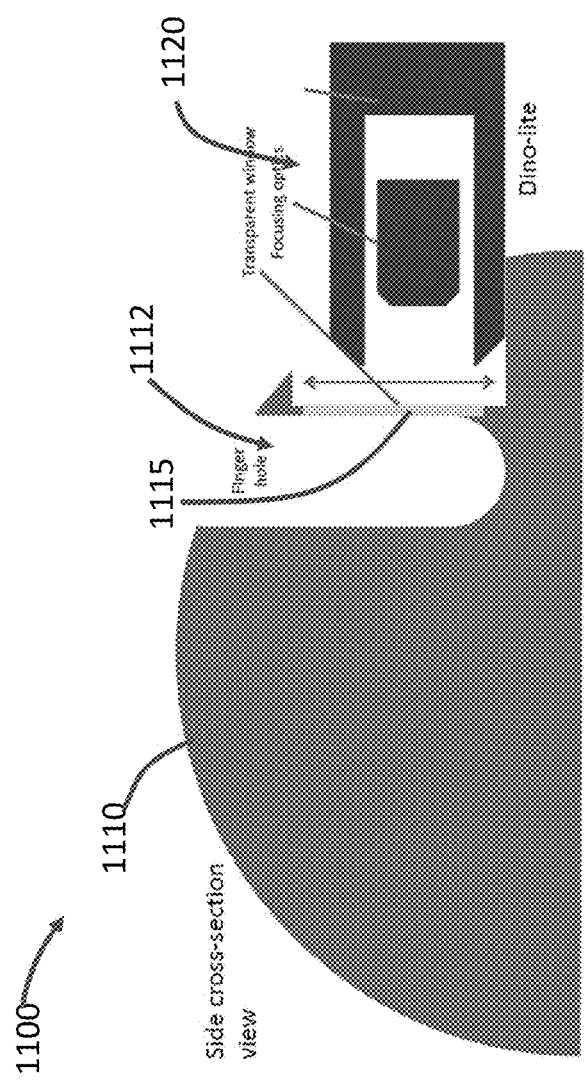

FIG. 11C shows a schematic of a system 1100 substantially similar to the system shown in FIGS. 11A-11B in accordance with some embodiments. The system 1100 includes an adjustable transparent window 1115 disposed between finger hole 1112 and imager 1120. By adjusting the height of window 1115, imagers 1120 having different sizes may be used to capture images of the finger.

Figure 12A:
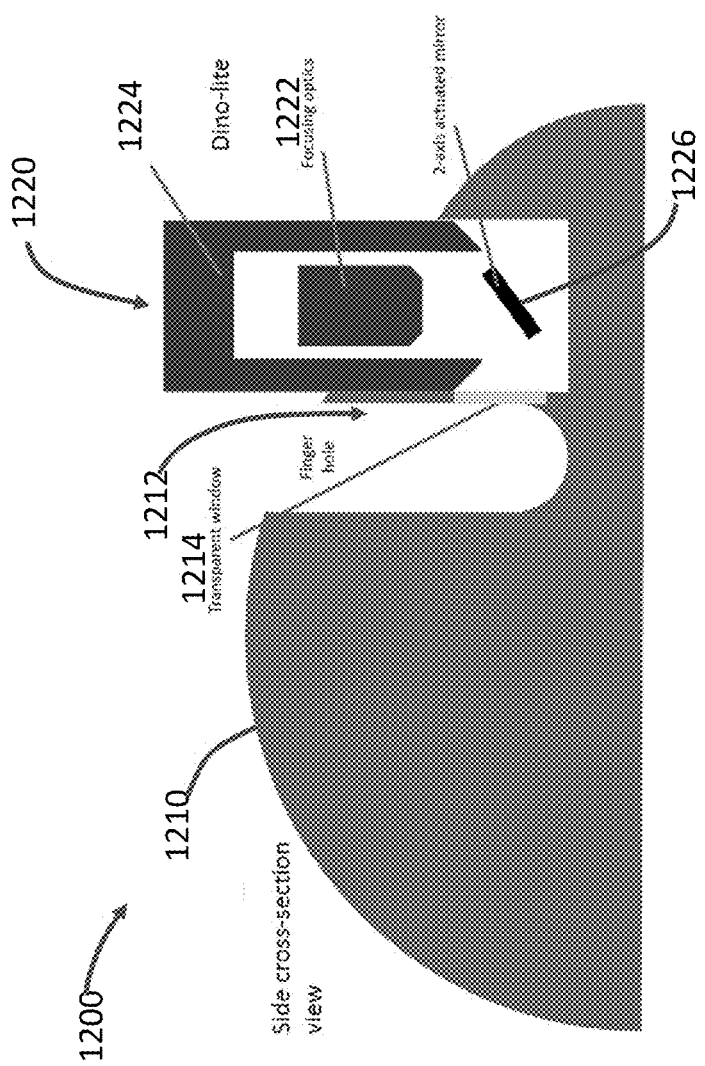
FIGS. 12A-12B are schematics of systems for analyzing blood cell dynamics using an imager in vertical configuration in accordance with some embodiments.
Figure 12B:
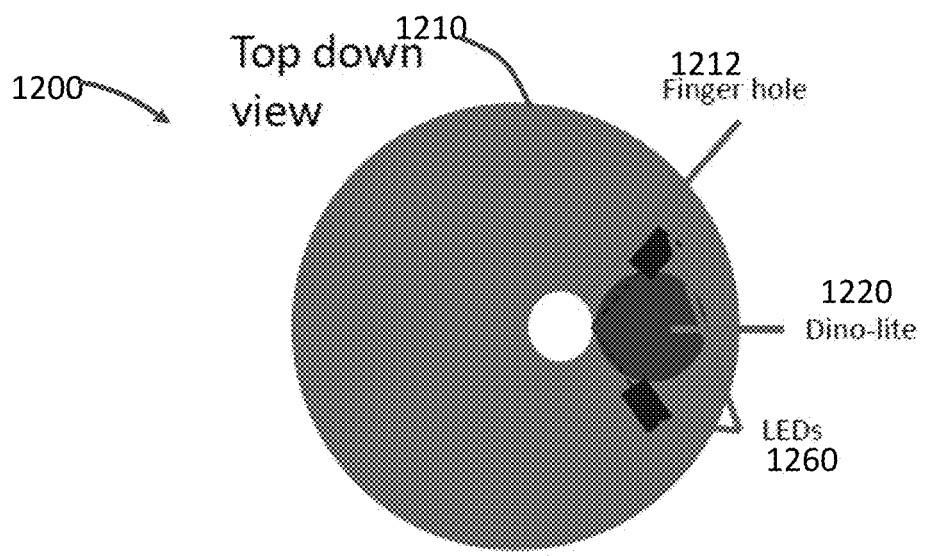

FIGS. 12A-12B are schematics of a system for capturing in vivo images for non-invasive analysis of WBC events according to some embodiments. In some embodiment, some or all aspects of the system of FIGS. 12A-12B can be structurally and/or functionally similar to one or more of the systems, apparatuses, and devices as described herein such as, for example, the system 2300 and/or the device 2340, as described in greater detail with respect to FIG. 23.

FIG. 12A is a side view of system 1200, and FIG. 12B is a top view of system 1200. System 1200 includes finger holder 1210 having finger hole 1212 to receive at least a portion of a human finger (e.g., a nailfold portion of the finger). Finger holder 1210 is also configured to receive imager 1220, which is in optical communication with the finger received by finger hole 1212 through transparent window 1214 and mirror 1226 so as to take images or videos of the finger. The imager further includes focusing optic 1222 to collect light reflected or scattered from the finger and detector 1224 to receive the reflected or scattered light so as to form images of the finger. In system 1200, imager 1220 is disposed in a vertical configuration. Mirror 1226 is configured to reflect the image of the finger toward imager 1220. In some embodiments, mirror 1226 is coupled to an actuator (not shown), which can tilt mirror 1226 in two directions. The tilting may help imager 1220 point at the desired portion of the finger for imaging. Similar to system 1100, system 1200 also may have an illumination source 1260 to facilitate capturing images by imager 1220.

Figure 13:
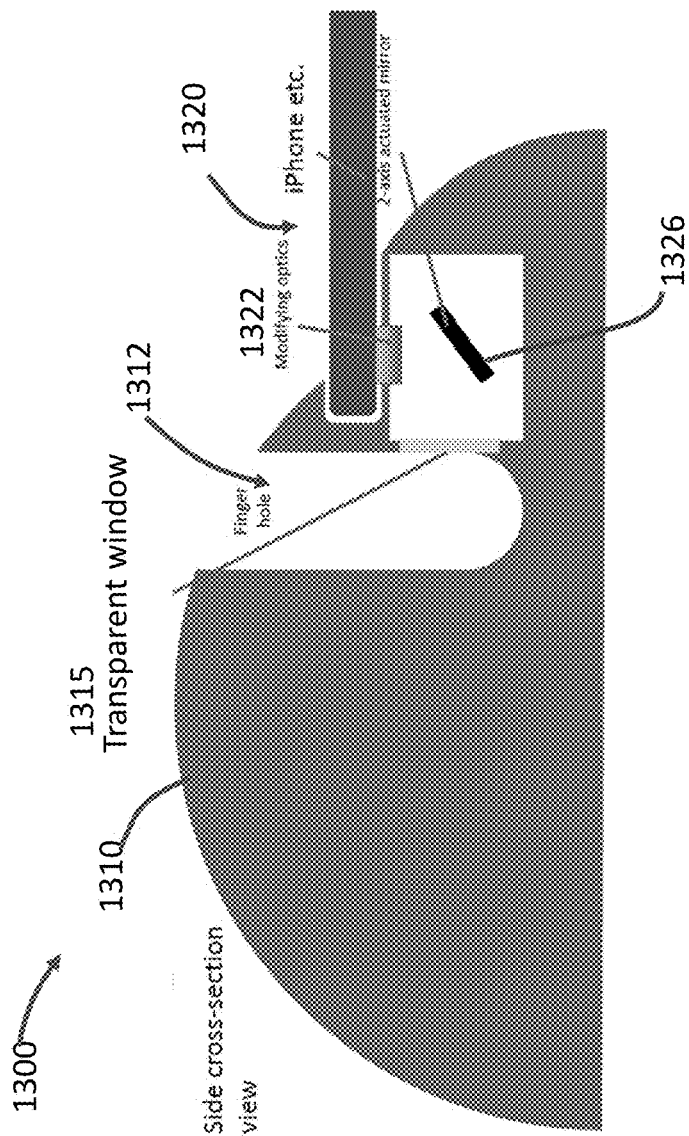
FIG. 13 is a schematic of a system for analyzing blood cell dynamics analysis using a smartphone in accordance with some embodiments.

FIG. 13 is a schematic of a system for performing in vivo and non-invasive analysis of blood cell dynamics using a camera-equipped device (e.g., a smartphone) according to some embodiments. In some embodiment, some or all aspects of the system of FIG. 13 can be structurally and/or functionally similar to one or more of the systems, apparatuses, and devices as described herein such as, for example, the system 2300 and/or the device 2340, as described in greater detail with respect to FIG. 23.

System 1300 includes finger holder 1310 having finger hole 1312 to receive at least a portion of a finger for imaging. Finger holder 1310 is also configured to receive smartphone 1320 such that the camera in smartphone 1320 is in optical communication with the finger in finger hole 1312 via transparent window 1315 and mirror 1326. System 1300 also may include modifying optic 1322, disposed in front of the camera in smartphone 1320, so as to adapt smartphone 1320 for better image capture. For example, modifying optic 1322 may include a lens to adjust the focal length (optical zooming) of the camera in smartphone 1322. Cameras in many smartphones do not have optical zooming, thus including lens 1322 may increase the optical flexibility of the camera. The focal length of the camera is also related to the resolution of the images captured by the camera. Therefore, use of lens 1322 also may adjust the resolution of the images for further processing.

Smartphone 1320 generally includes its own memory and processor. Methods described in earlier sections of this application can be encoded as processor executable instructions into the memory of smartphone 1320. In operation, images taken by the camera may be transmitted to the processor for the analysis of blood cell dynamics. In some embodiments, images taken by the camera are transmitted wirelessly (e.g., via Bluetooth, WiFi, 3G network, 4G network, or any other wireless communication protocols known in the art) to another processor for processing. In some embodiments, images taken by the camera are locally saved into the memory of smartphone 1320.

FIGS. 14A-14D are images of systems and apparatus for in vivo and non-invasive analysis of blood cell dynamics according to some embodiments. In some embodiment, some or all aspects of the systems and apparatus of FIG. 14A-14D can be structurally and/or functionally similar to one or more of the systems, apparatuses, and devices as described herein such as, for example, the system 2300 and/or the device 2340, as described in greater detail with respect to FIG. 23.

Figure 14A:
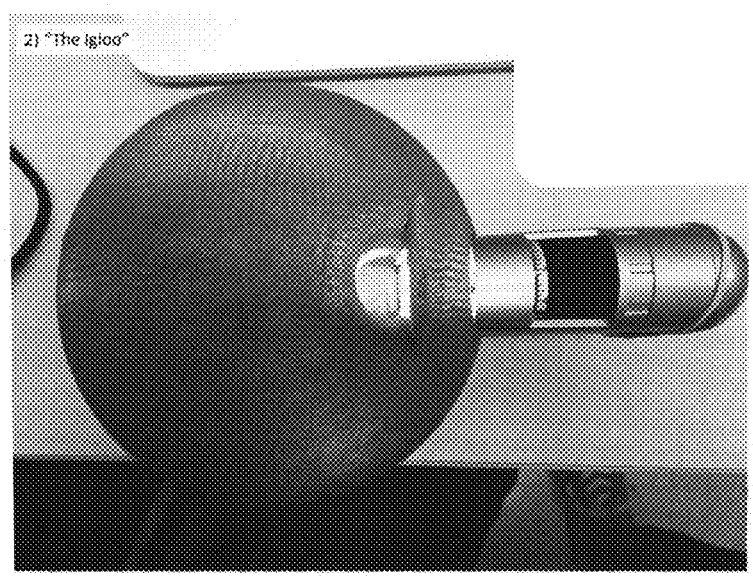
FIGS. 14A-14D are images of systems and apparatus for analyzing blood cell dynamics analysis in accordance with some embodiments.
Figure 14B:
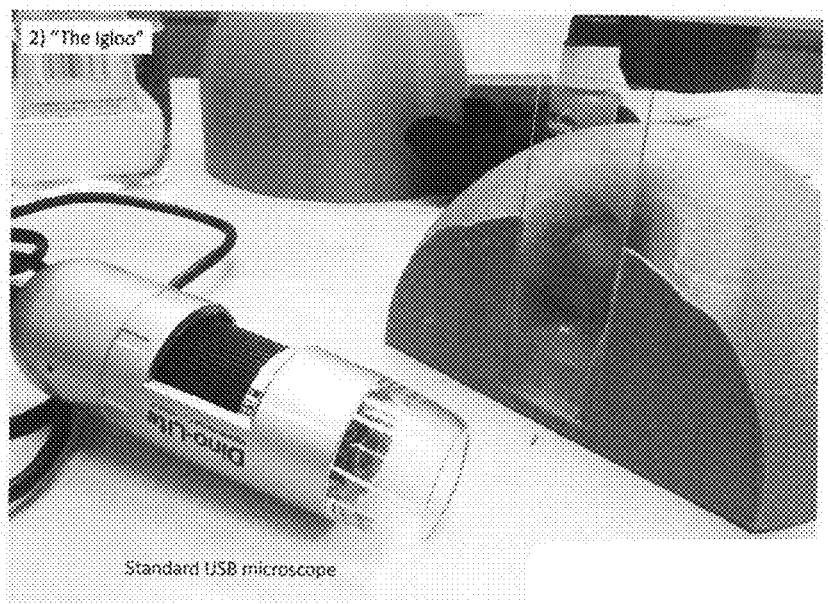
Figure 14C:
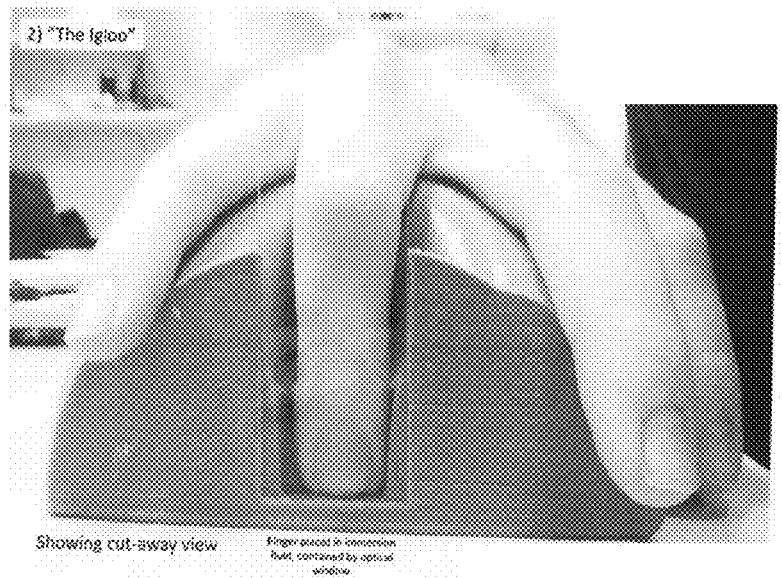
Figure 14D:
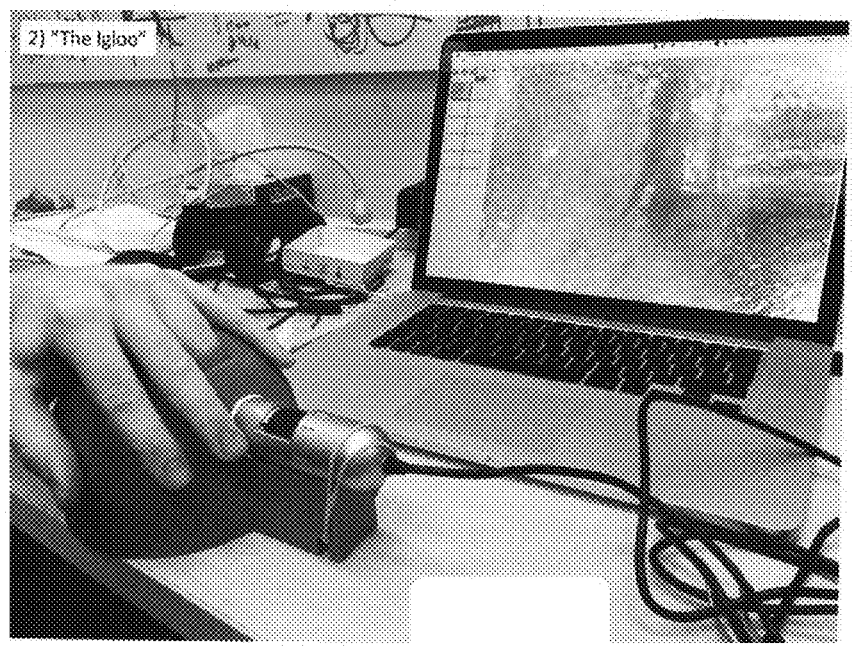

FIG. 14A shows a finger holder coupled to an imager. The imager may use a commercially available capillaroscope (e.g., Dino-Lite Digital Microscope (available from BigC-.com (Torrance, Calif.)). The imager may include its own illumination source such that when a finger is placed in the finger hole, the finger is well illuminated for imaging. FIG. 14B shows an imager and a finger holder de-coupled. FIG. 14C shows a finger holder when a finger is placed in the finger hole. FIG. 14D shows a system including a finger holder, an imager, and a computer that is connected to the imager via, e.g., a USB connection. The computer may display, in real time, images or video captured by the imager. Methods described in earlier sections of this application may be saved as processor executable instructions in a memory of the computer, a processor of which then may perform analysis of the images to detect WBC events.

Figures 15A, 15B, 15C:
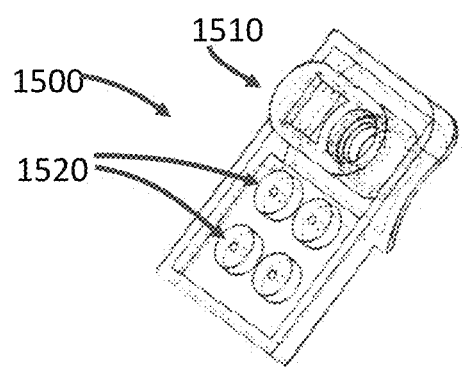

FIGS. 15A-15G are views of an adapter that can be attached to a smartphone for capturing images of a nail fold with a camera-equipped device for blood cell dynamics analysis in accordance with some embodiments. FIG. 15A is a perspective view of adapter 1500 including window section 1510 and a plurality of suction cups 1520. Window section 1510 may be aligned with the camera typically available in smartphones. Suction cups 1520 may secure adapter 1500 to, for example, a smartphone. While four suctions cups are shown in FIG. 15A, the number of the suction cups can be any number that is applicable. Alternatively or in addition, an adapter may be attached or secured to a smartphone or other device using a clip, adhesive, etc.

FIG. 15B shows adapter 1500 from perspective angle to illustrate the structure of window section 1510, which further includes window 1512 and finger receptor 1514. Window 1512 is substantially transparent or at least transparent at certain wavelengths so as to allow the camera to take images of fingers. Finger receptor 1514 has an internal contour that fits the general shape of fingers so as to firmly secure fingers with adapter 1500, thereby reducing burden of image registration (e.g., due to movement) in subsequent processing.

Figures 15D, 15E, 15F, 15G:
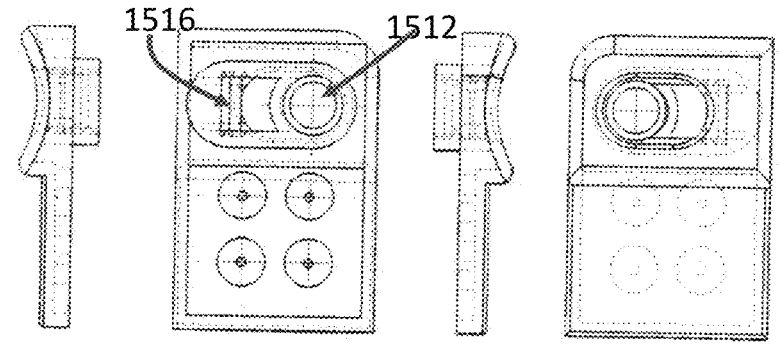

FIG. 15C is a top view of adapter 1500, FIG. 15D is a first side view of adapter 1500, and FIG. 15F is a second side view of adapter 1500. FIG. 15E is a back view of adapter 1500 illustrating illumination channel 1516 and window 1512. FIG. 15G is a front view (the side receiving the finger) of adapter 1500. As shown in FIGS. 15E and 15G, illumination channel 1516 is generally not through the entire depth of adapter 1500. Instead, illumination channel 1516 may be in optical communication with a flash light that is generally available in smartphones and other camera-equipped devices beside the camera lens. Illumination channel 1516 may receive light emitted by the flash light and reflect it toward window 1512 so as to illuminate at least a portion of the finger to be imaged.

FIGS. 15H-15J illustrate illumination channel 1516. FIG. 15H is a perspective view of adapter 1500. FIG. 15I is a perspective cross-sectional view of part of adapter 1500 to illustrate window 1512 and illumination channel 1516. FIG. 15J is a cross-sectional view of adapter 1500 to illustrate structures of illumination channel 1516. In particular, illumination channel 1516 may include a curved surface 1517 that reflects received light toward window 1512 so as to illuminate a finger typically disposed in front of window 1512 for imaging.

Figure 16:
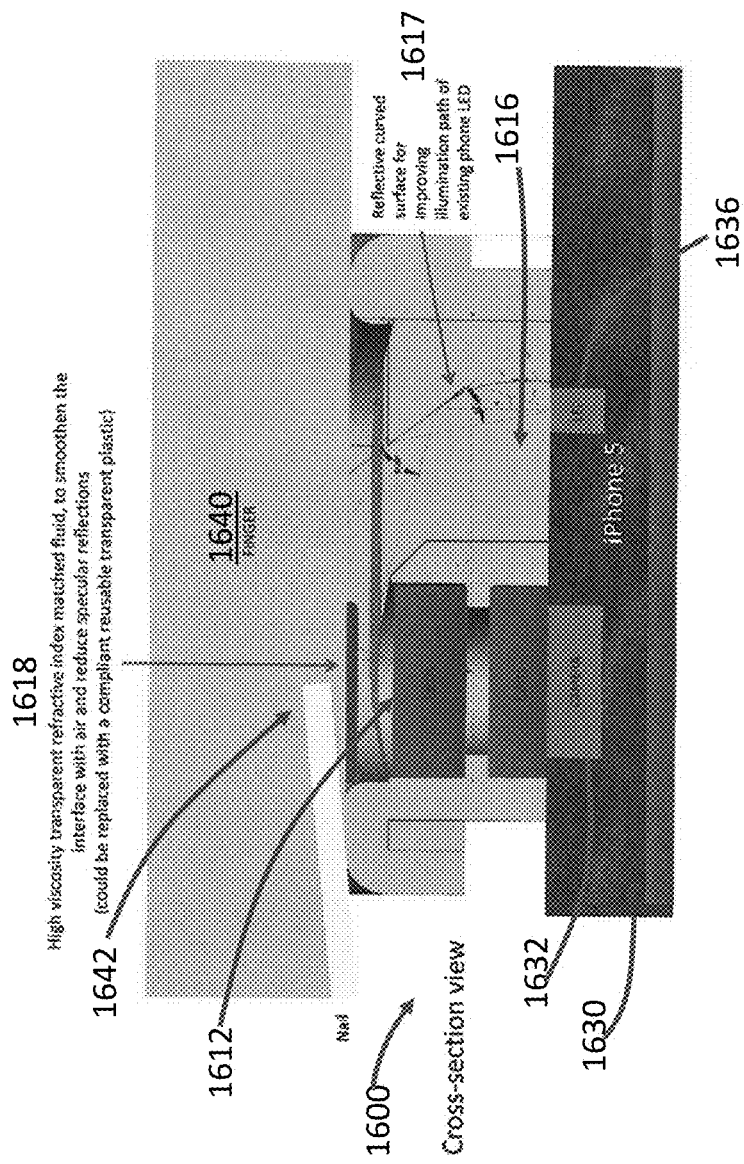
FIG. 16 is a schematic of a system including a smartphone and an adapter for capturing images of a nailfold for blood cell dynamics analysis in accordance with some embodiments.

FIG. 16 is a schematic of a system including a smartphone and an adapter for capturing images of a nail fold for blood cell dynamics analysis in accordance with some embodiments. In some embodiment, some or all aspects of the system of FIG. 16 can be structurally and/or functionally similar to one or more of the systems, apparatuses, and devices as described herein such as, for example, the system 2300 and/or the device 2340, as described in greater detail with respect to FIG. 23.

Adapter 1600 includes window 1612 in optical communication with camera 1632 of smartphone 1630. Adapter 1600 also includes illumination channel 1616 in optical communication with LED light 1636 of smartphone 1630. Illumination channel 1616 receives light emitted by LED light 1636, and curved surface 1617 in illumination channel 1616 reflects the received light toward window 1612 so as to illuminate the finger 1640 (more specifically nailfold 1642), which is in close contact with window 1612.

In some embodiments, window 1612 may include two lenses to change the focal length of camera 1632 in smartphone 1630. Changing the focal length can also change the resolution of the images taken by camera 1632. In some examples, index matched fluid 1618 may be disposed between window 1612 and nailfold 1642. Index matched fluid 1618 may have a refractive index similar to that of a nailfold or of the material of window 1612 so as to reduce specular reflection at the surface of window 1612 or at the surface of nailfold 1642. In some embodiments, index matched fluid 1618 has high viscosity. In some embodiments, index matched fluid 1618 may be replaced by a compliant reusable transparent plastic.

Figure 17A:
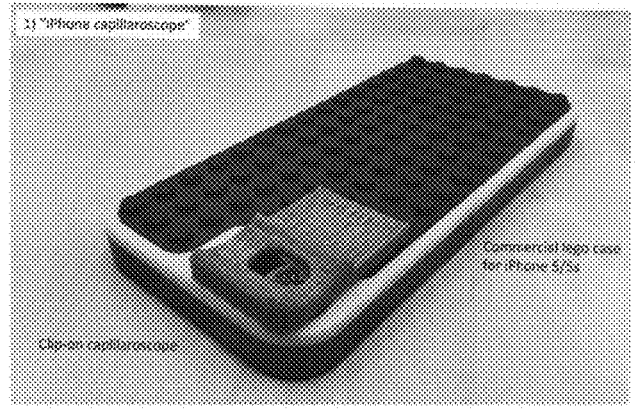
FIGS. 17A-17B are images of a system including a smartphone and an adapter for capturing images of a nailfold for blood cell dynamics analysis in accordance with some embodiments.
Figure 17B:
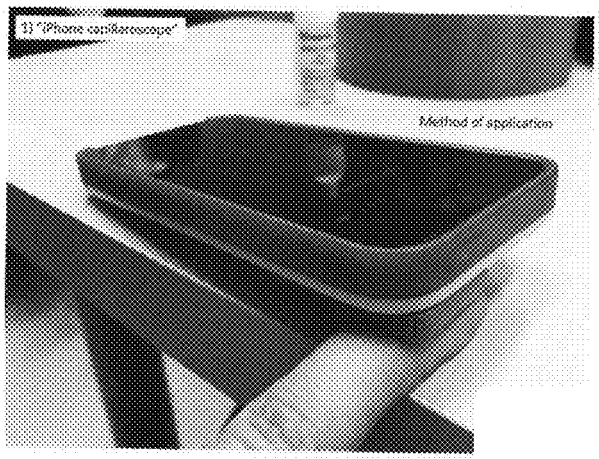
Figure 18:
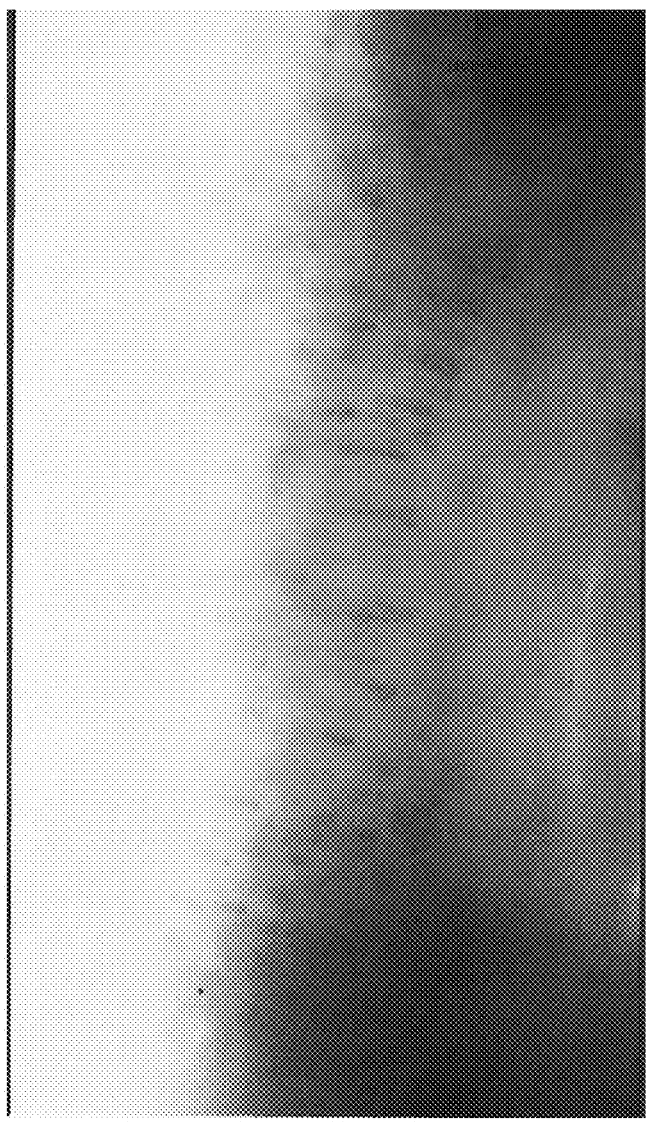
FIG. 18 is an example image captured by the system shown in FIGS. 17A-17B in accordance with some embodiments.

FIG. 17A shows a smartphone with an adapter attached to the smartphone so as to allow image taking of a nailfold according to some embodiments. FIG. 17B shows the smartphone and the adapter when a finger is placed in front of the adapter for imaging. FIG. 18 is an image captured by the smartphone using the adapter shown in FIGS. 17A-17B. Multiple capillary structures are visible in the image for further analysis of blood cell dynamics in accordance with some embodiments.

Figure 19:
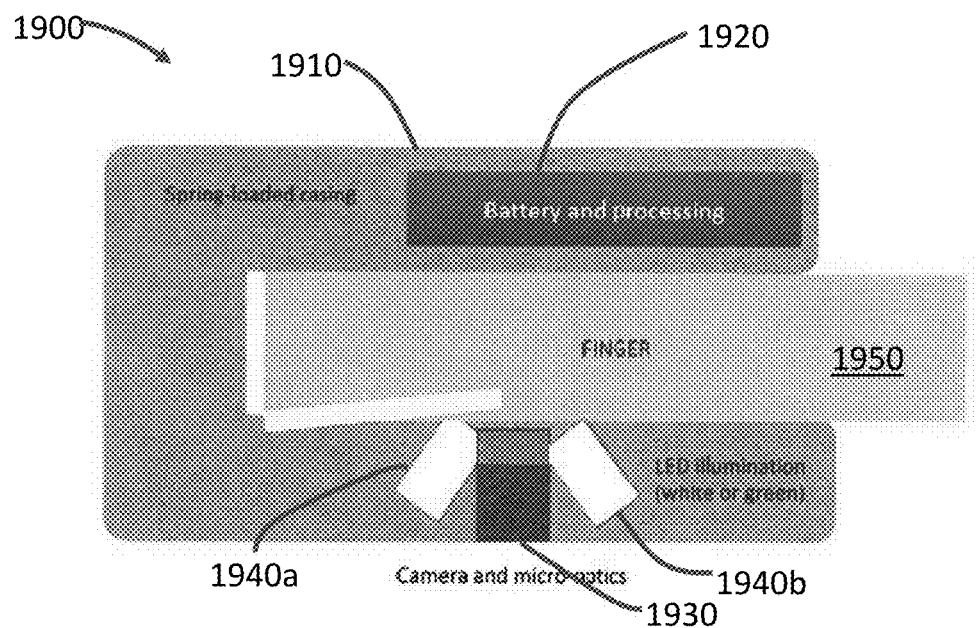
FIG. 19 is a schematic of a clamp device for performing blood cell dynamics analysis from images of a nailfold in accordance with some embodiments.
Figure 20:
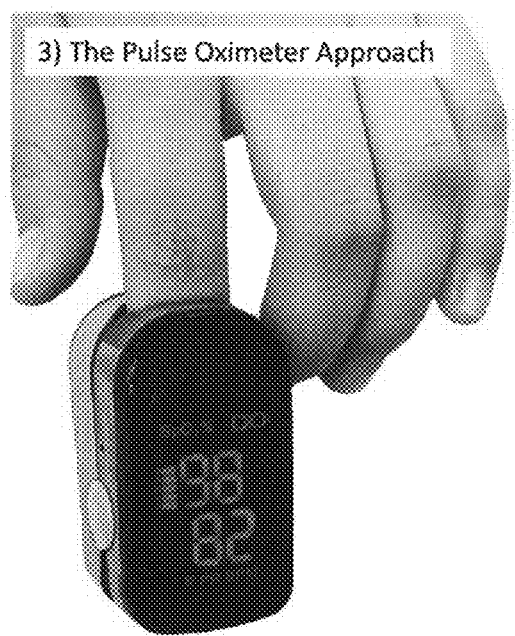
FIG. 20 is an image of a clamp device being used to capture images of a nailfold and analyzing blood cell dynamics.

FIG. 19 is a schematic of a clamp device for capturing images and performing blood cell dynamics analysis according to some embodiments. Clamp device 1900 includes spring-loaded casing 1910 for securely receiving finger 1950. When finger 1950 is placed in clamp device 1900, camera 1930 can take images of finger 1950 with finger 1950 illuminated by a pair of LED lights 1940a and 1940b. In some embodiments, LED lights 1940a and 1940b emit broad-spectrum white light. In some embodiments, LED lights 1940a and 1940b emit green light which can be effectively reflected by WBCs. Clamp device also may include a battery and/or processing unit 1920 for processing images taken by camera 1930 according to methods described above. FIG. 20 shows a clamp device coupled with a finger for blood cell dynamics analysis. As can be seen from FIG. 20, the spring-loaded casing helps to secure the finger with the clamp device so as to reduce or eliminate relative movement between the finger and the camera.

Figure 21A:
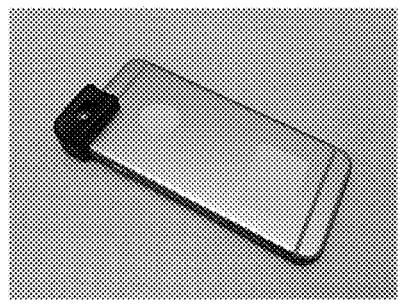
Figure 21B:
Figure 21C:
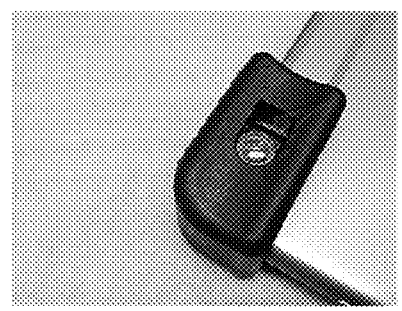
Figure 21D:
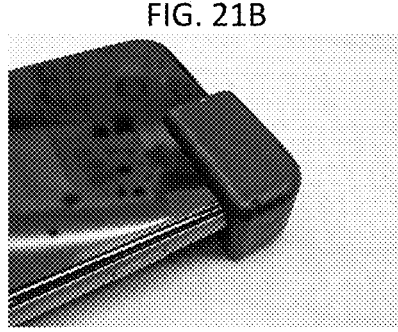
Figure 21E:
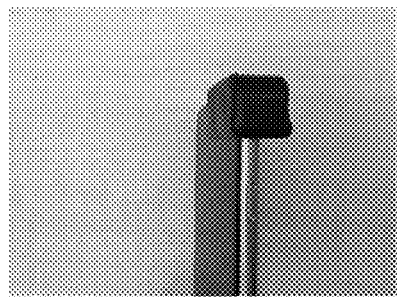
Figure 21F:
Figure 22A:
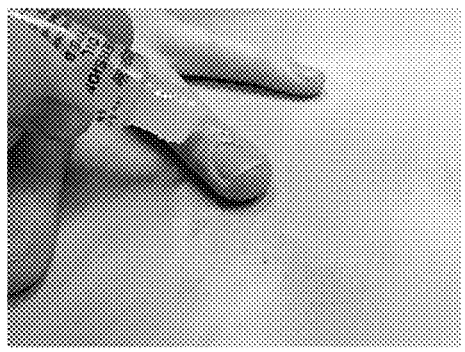
FIGS. 22A-22D are images illustrating a method of using a smartphone adapter for capturing images of a nailfold with a smartphone camera for capillaroscopy and hematology analysis in accordance with some embodiments.
Figure 22B:
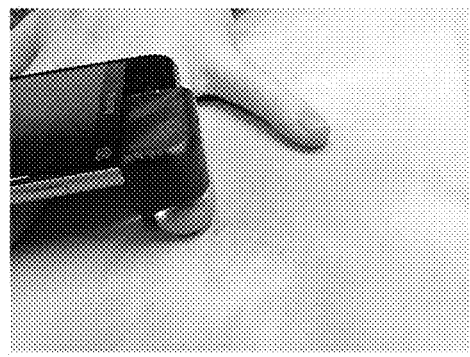
Figure 22C:
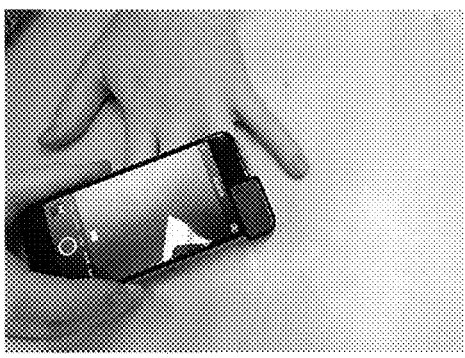
Figure 22D:

FIGS. 21A-21O are views of an adapter for capturing images of a nailfold with a smartphone camera for capillaroscopy and hematology analysis in accordance with some embodiments. In particular, FIGS. 21A-21F are images of perspective views of a smartphone adapter. In FIGS. 21A-21E, the adapter is attached to a smartphone such that the smartphone camera may be utilized. In FIG. 21F, the adapter is shown unattached. FIGS. 21G-21O are wireframes showing the side and perspective views of the adapter. FIGS. 22A-22D illustrate a method of using a smartphone adapter attached to a smartphone such that the smartphone camera may be used for capillaroscopy and hematology analysis according to some embodiments. In FIG. 22A, index matched fluid is disposed on the surface of a nail fold of a user. In FIGS. 22B-22D, the smartphone is positioned over the finger such that the adapter rests on the finger and the smartphone camera is aligned with the nailfold.

Figure 23:
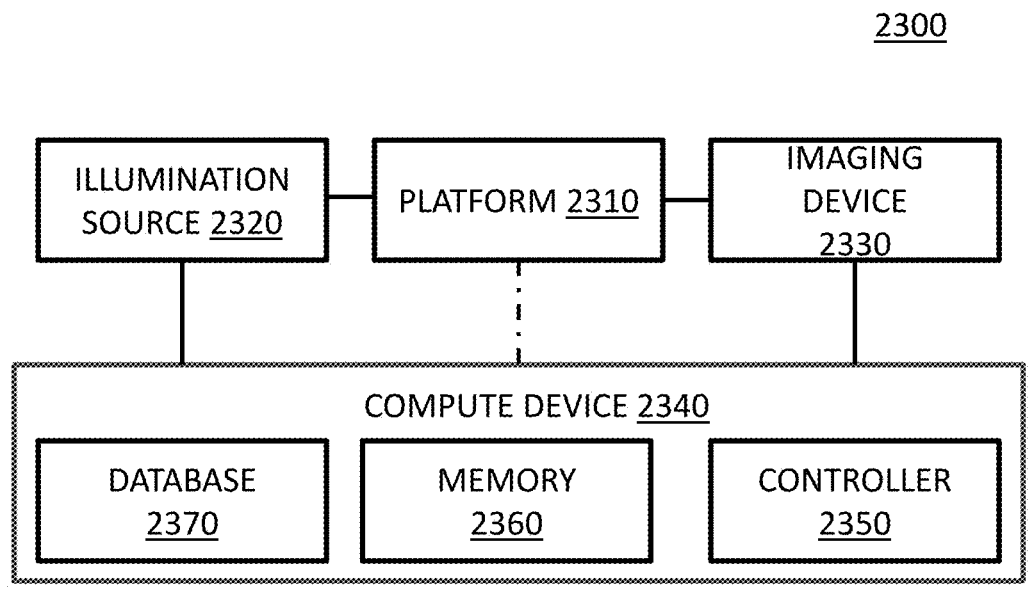
FIG. 23 illustrates a system for non-invasive hematological measurements, according to embodiments.

FIG. 23 is a schematic illustration of an environment/system 2300 in which non-invasive hematological measurements can be implemented and/or carried out. In some embodiments, aspects of the system 2300 can be structurally and/or functionally similar to the systems, apparatuses, and/or devices described herein with respect to FIGS. 1-22 and 31-60, and/or can perform the methods described in FIGS. 1-2.

The system 2300 includes a platform 2310, an illumination source 2330, an imaging device 2320, and a compute device 2340. In some embodiments, all components of the system 2300 can be included in a common casing such as, for example, a single housing that presents the system 2300 as an integrated, one-piece device for a user. In other embodiments, at least some components of the system 2300 can be in separate locations, housings, and/or devices. For example, in some embodiments, the compute device 2340 can be a smartphone in communication with the illumination source 2320 and/or the imaging device 2330 via one or more networks, each of which can be any type of network such as, for example, a local area network (LAN), a wide area network (WAN), a virtual network, a telecommunications network, and/or the Internet, implemented as a wired network and/or a wireless network. Any or all communications can be secured (e.g., encrypted) or unsecured, as is known in the art. The system 2300 and/or the compute device 2340 can be or encompass a personal computer, a server, a work station, a tablet, a mobile device, a cloud computing environment, an application or a module running on any of these platforms, and/or the like.

It is understood that while described herein as a system for hematological measurements in a nailfold portion for ease of explanation, aspects of the systems, devices, and methods disclosed herein are useful for hematological measurements in any tissue having a capillary structure (e.g., a capillary bed, superficial capillaries, peripheral capillaries, capillaries in other portions of the finger of the user, and/or the like) that can be imaged as described herein. Non limiting examples include capillaries in retina, ear lobes, lips, gums, and/or the like. As an example, the platform 2310 can be adapted to be pressed against a gum line of a user during use for hematological measurements in a capillary bed of the gum line. As another example, the platform 2310 can encompass a tonometer-like instrument for pressing against the retina during use for hematological measurements in capillaries of the retina.

In some embodiments, the platform 2310 receives a finger of a user during use. In some embodiments, the platform 2310 can be structurally and/or functionally similar to the finger holder(s) described in FIGS. 11-14, 19. In some embodiments, the platform 2310 is shaped to guide the placement of the finger of a user so as to position a nailfold portion of the finger in a predetermined location within the platform.

The illumination source can be any suitable source of substantially monochromatic light including, but not limited to, light emitting diodes (LEDs), laser light, filtered light, and/or the like. The illumination source can be positioned with respect to the platform 2310 to illuminate the nailfold portion of the finger of the user during use.

The imaging device 2330 can include any suitable imager as disclosed herein, including a smartphone camera, a capillaroscope, and/or the like. In some embodiments, the imaging device 2330 captures images of the nailfold portion of the finger of the user during use in response to the illumination of the nailfold portion by the illumination source 2330, such as, for example, based on a synchronization/timing signal from the device 2340. In some embodiments, the imaging device 2330 captures a set of images per acquisition such as, for example, a time-lapse series. In some embodiments, the imaging device 2330 captures the set of images as a video/video file at a capture rate of, for example, 60 frames/second, for 60 seconds.

In some embodiments, the platform 2310 is optically coupled to the illumination source 2330 and the imaging device 2330 via any suitable and independent means such as, for example, beam shaping and/or beam steering optics, one or more optical conduits such as optical fiber(s), direct/optics-free coupling, and/or the like.

The compute device 2340 includes at least a controller 2350 and a memory 2360. FIG. 23 also illustrates a database 2370, although it will be understood that, in some embodiments, the database 2370 and the memory 2360 can be a common data store. In some embodiments, the database 2370 constitutes one or more databases. Further, in other embodiments (not shown), at least one database can be external to the device 2340 and/or the system 2300. The compute device 2340 can also include one or more input/output (I/O) interfaces (not shown), implemented in software and/or hardware, for other components of the system 2300, and/or external to the system 2300, to interact with the device 2340.

The memory 2360 and/or the database 2370 can independently be, for example, a random access memory (RAM), a memory buffer, a hard drive, a database, an erasable programmable read-only memory (EPROM), an electrically erasable read-only memory (EEPROM), a read-only memory (ROM), Flash memory, and/or so forth. The memory 2360 and/or the database 2370 can store instructions to cause the controller 2350 to execute processes and/or functions associated with the system 2300.

The controller 2350 can be any suitable processing device configured to run and/or execute a set of instructions or code associated with the device 2340. The controller 2350 can be, for example, a general purpose processor, a Field Programmable Gate Array (FPGA), an Application Specific Integrated Circuit (ASIC), a Digital Signal Processor (DSP), and/or the like.

The controller 2350 receives the set of images/video data from the imaging device 2330. The controller 2350 can execute computer-executable instructions (e.g., those stored in the memory 2360 and/or the database 2370) to process the set of images in any suitable manner In some embodiments, for example, given an input raw video/set of images with a resolution of 1280×1024 pixels and a frame rate of 60 frames/images per second, and given an input initial frame index, the controller 2350 can extracts two uncompressed videos restricted to a duration of one minute (3600 frames) starting from that initial frame index. In some embodiments, the first video at the native pixel resolution, is downsampled at, for example, half of the pixel resolution (640×512), in order to accelerate processing during registration and capillary detection, as described herein. An uncompressed image is also extracted as the first frame/image of the second video.

In some embodiments, the controller 2350 executes a global registration process on the set of images to eliminate movements that occur between frames/images. For example, in some embodiments, the controller 2350 aligns all images with respect to the first image of the set of images. In some embodiments, the alignment includes correcting for horizontal and/or vertical translations of the view captures in the set of images. In some embodiments, the controller 2350 corrects the horizontal and/or vertical translation for each image in a manner that maximizes its cross-correlation with the first image.

In some embodiments, prior to such an alignment process, the controller 2350 normalizes the intensity of each image of the set of images by, for example, a spatial high-pass filter based on predetermined characteristics (e.g., a square filter of size 75×75 pixels), and/or any other suitable image-flattening techniques. In this manner, the resulting, processed set of images (sometimes also referred to simply as "the set of images") are cropped to a viewing area that remains in view across the entire set of images.

The controller 2350 can execute computer-executable instructions to (e.g., those stored in the memory 2360 and/or the database 2370) detect, in each image of the processed set of images, one or more capillaries in the nailfold portion of the finger to identify a first set of capillaries across the set of images. In some embodiments, detecting the first set of capillaries includes detecting each capillary of the first set of capillaries on at least one image of the set of images.

In some embodiments, the controller 2350 detects each capillary of the first set of capillaries as follows. The controller 2350 receives training data that includes images of capillaries that fulfill one or more predetermined criterion for one or more attributes (e.g., at least for a first attribute of the one or more attributes) of the identified capillaries. In some embodiments, the one or more attributes include structural attributes of the capillary itself such as, but not limited to, capillary length (e.g., a sufficient length such that a cellular event moving at a typical or maximum blood flow speed would appear in more than one frame given the imager/imaging device's frame rate), capillary width (e.g., a capillary width from about 10 μm to about 20 μm, including all values and sub-ranges in between), capillary depth (e.g., a capillary depth from about 10 μm to about 350 μm, including all values and sub-ranges in between), average capillary diameter, lateral capillary diameter, vertical capillary diameter, capillary shape (e.g. capillaries must exhibit clear arterial and venous limbs), and/or the like.

The average capillary diameter can be generally characterized as any average of multiple diameter measurements of the capillary, either at a single cross section, or at multiple cross sections along the length of the capillary. In some embodiments, the structural attribute is average capillary diameter, and the predetermined criterion is that the average capillary diameter must be between about 10 μm to about 20 μm.

In some embodiments, the one or more attributes include flow attributes such as, but not limited to, blood flow speed in the capillary, transit time for a cell within the visible portion of the capillary, volumetric flow rate, mass flow rate, directionality of the flow, blood flow speed stability, and/or the like.

In some embodiments, the one or more attributes include imaging attributes of the image of the capillary such as, but not limited to, contrast (e.g., based on measurement of luminance contrast, root mean square (RMS) contrast, Weber contrast, Michelson contrast, histogram-based techniques, and/or the like), focus/detail (e.g., as measured by gradient-based operators, Laplacian operators, wavelet operators, discrete cosine transform (DCT), frequency domain analysis, phase coherency, luminance map, singular value decomposition, learning algorithm(s), and/or the like), signal-to-noise ratio, image stability (e.g. as measured by image registration techniques, optical flow and/or the like), and/or the like. In some embodiments, a combination of structural and imaging attributes can be employed. In some embodiments, the training data is human-expert generated data that also accounts for requirements that the capillaries be generally clear (e.g., no air bubbles can occlude the capillaries) and have clear morphology (e.g., have clear arterial and venous limbs). The controller 2350 trains a deep learning neural network (e.g., a fully convolutional neural network, such as the deep learning YOLO method/technique as generally disclosed in Joseph Redmon et al. 2016, The IEEE Conference on Computer Vision and Pattern Recognition, the entire disclosure of which is incorporated herein by reference) based on the training data to recognize the first set of capillaries in the set of images.

In some embodiments, the controller 2350 generates, for each detected capillary in each image of the set of images, a bounding box around that capillary, and also generates a confidence value associated with the likelihood that the detection corresponds to a capillary, and not another structure/artifact. In some embodiments, the first set of capillaries include those detected capillaries having a corresponding confidence value that meets or exceed a predetermined confidence threshold.

In some embodiments, the controller 2350 identifies a second set of capillaries from the first set of capillaries. In some embodiments, the second set of capillaries includes those capillaries that are detectable in a threshold number of images, of the set of images. For example, if the set of images includes 60 images, the second set of capillaries can include those capillaries visible in at least 40 of the 60 images. In some embodiments, the second set of capillaries includes those capillaries that are detectable in a threshold number of images and are associated with a confidence value that exceeds the confidence threshold in a minimum or all of those images. In some embodiments, the controller 2350 generates an indication of the threshold number of images based on training data.

In an example embodiment, the controller 2350 feeds the neural network as described herein with 130 training images having 795 corresponding bounding boxes (around capillaries) created manually. The training images were extracted as the first frames/images of 130 distinct capillary videos/sets of images stemming from 43 distinct patients, thus ensuring sufficient data diversity. The bounding boxes were manually defined by one human expert around each capillary that fulfill the set of criteria as described herein. The image dataset is split into a first set and a second set based on temporal order of acquisition, and the confidence threshold was set to C=0.45 to avoid detections of unsuitable capillaries or artefacts. This condition detected, as the first set of capillaries, in the first set, 66 images from 23 patients with a total of 416 annotated bounding boxes around identified capillaries, and in the second set, 64 images from 19 patients with a total of 379 annotated bounding boxes around identified capillaries. The neuronal network was fed with the first set and the second for a total of 900 iterations each time, thus creating corresponding learned weights $W_{s1}$ and $W_{s2}$. Explained with reference to the exampled YOLO technique, in some embodiments, these learned weights learned weights $W_{s1}$ and $W_{s2}$ are determined as the free parameters of a convolutional-neural-network structure and optimized in such a way that the capillaries detected by the neural network, when executed on the images from the training set, best match those that the human-rater pre-labeled on these same images as a reference.

Figure 24A:
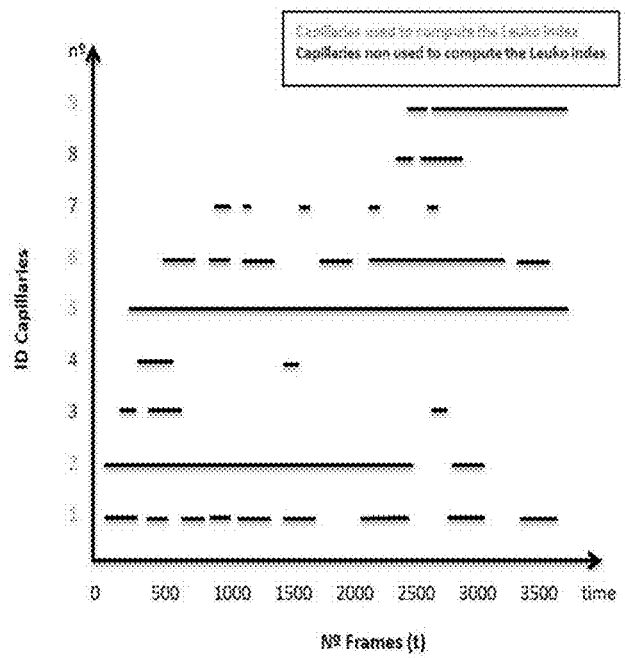
FIGS. 24A-24B illustrates Capillary tracking criteria to select suitable capillaries. Each capillary was tracked with a given identifier (id) during 3600 frames of a video.
Figure 24B:
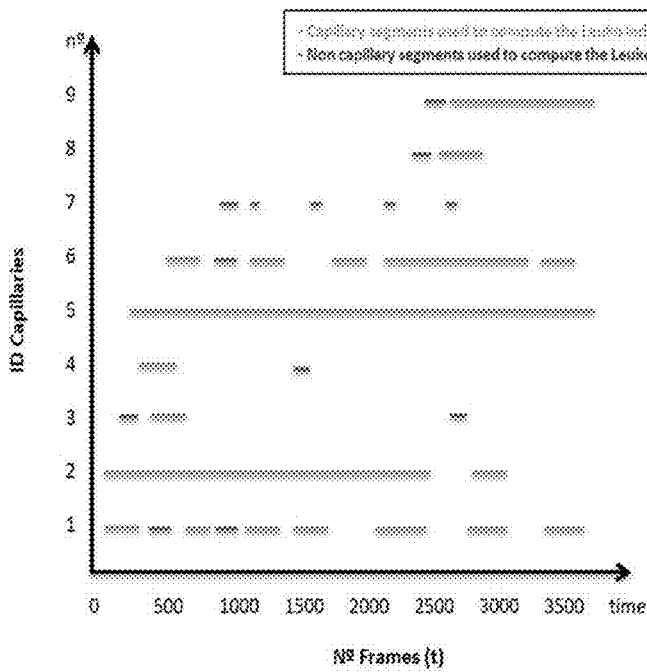

Following the above single-frame-detection step/identification of the first set of capillaries, each capillary was then tracked with a given identifier. The capillary tracking is based on overlapping and Kalman filtering, in the event missed detection occurs during frames, though it is understood that any other suitable technique may be used for capillary tracking including, but not limited to, mathematical morphology, cross-correlation, mutual information, optical flow, machine learning, and/or the like. A capillary is selected for the second set of capillaries if it is in at least $t_f$ images (threshold number of images) i.e., if it is associated with a bounding box exceeding the confidence parameter $\mathbb{C}$ in $t_f$ images, as shown in FIGS. 24A-24B. The parameter $t_f$ was empirically set to 600, except if less than 3 capillaries were selected. In the latter case, $t_f$ was set such that 3 capillaries were detected if possible (i.e., provided that at least 3 distinct capillaries were detected in single images).

Figure 25:
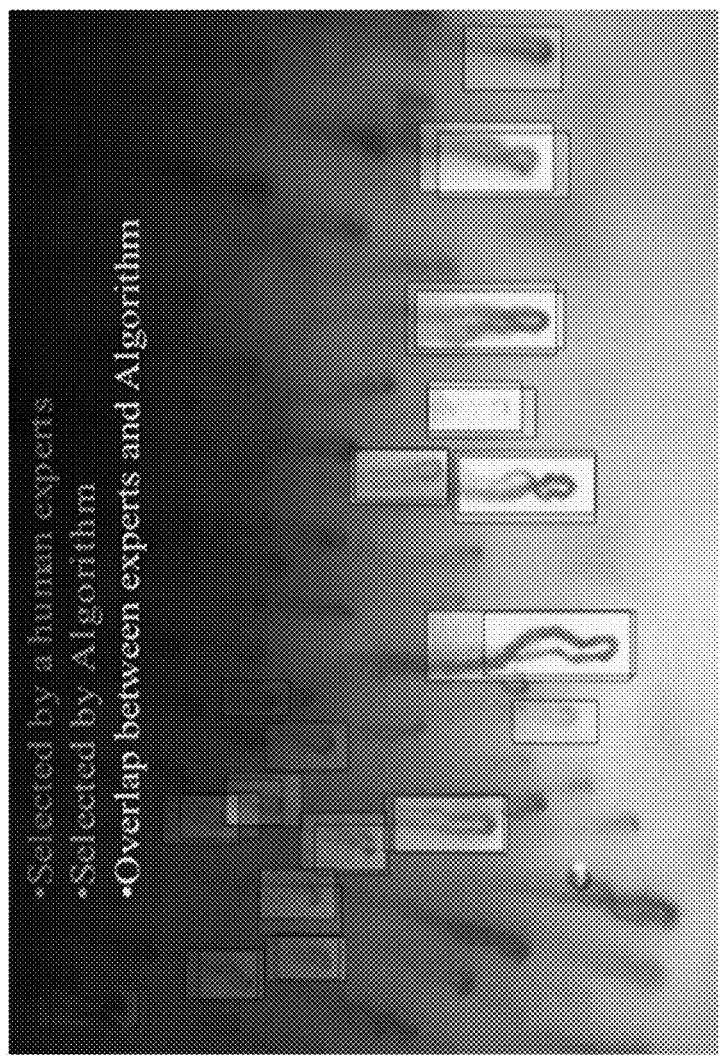
FIG. 25 illustrates capillary detection in a raw video using the neural network-based method/approach described herein, and comparison with human-expert-based performance. Results from the union between two raters (green) vs. results from neural network analysis (red; yellow if overlap).

To test the selection of the first set of capillaries, the steps mentioned herein (for detecting the first set of capillaries) are run on the first set with the weight $W_{s2}$, and the set second set with the weight $W_{s1}$. To validate the detection of the first set of capillaries, a comparison is made to a reference of 24 first images from 24 distinct sets of reference images/reference videos, where capillary boxes are annotated by two human experts who selected capillaries according to the following set of criteria: (A) Illumination. Capillaries must be visible with sufficient contrast to an observer; (B) Focus. Detailed capillary structures/dynamics must be visible and not blurred out; (C) Flow. Blood flow must exist to allow for potential events to be identified and counted; (D) Stability. Capillaries must fully remain within the video FOV in all frames; (E) Visibility. No object (e.g., air bubbles) can occlude capillaries. (F) Morphology. Capillaries must exhibit clear arterial and venous limbs. In the test videos/sets of images, for instance, 95% of the videos had 3 or more detected capillaries, and is associated with improved classification results. An example of capillary detection performed as detailed herein is illustrated in FIG. 25.

Referring again to FIG. 23, in some embodiments, the controller 23 detects, in the second set of capillaries, a set of (i.e., one or more) cellular events. In some embodiments, each cellular event of the set of cellular events is associated with passage of a white blood cell in a capillary of the second set of capillaries. As described in more detail herein, since red blood cells exhibit greater optical absorption than white blood cells at the wavelength(s) described herein, passage of a white blood cell in a capillary results in an "absorption gap" due to the presence of the white blood cell.

Accordingly, the term "cellular event" as used herein, and also sometimes referred to as a "gap" or simply an "event", can refer to one or more of the following: a) detection of an area of relatively greater absorption (indicative of the likely presence of red blood cells) adjacent to an area of relatively lower absorption compared to the first area (indicative of the likely presence of one or more white blood cells) within a capillary; b) detection of a first area of relatively greater absorption (indicative of the likely presence of red blood cells) adjacent to a second area of relatively lower absorption compared to the first area (indicative of the likely presence of one or more white blood cells downstream of the first area), where the second area is adjacent to a third area of differing absorption than that of the second area (indicative of either the likely presence of red blood cells downstream of the second area, or of an area substantially devoid of any cells) within a capillary.

It is understood that while disclosed herein for detection of white blood cells in capillaries, aspects of this disclosure are useful for detecting any other suitable cells as long as those cells exhibit a contrast in absorption relative to red blood cells. As an example, circulating tumor cells (CTCs) may be detectable by selecting capillaries (i.e., by selecting the first set of capillaries or the second set of capillaries) having a diameter similar to that of CTCs. As another example, one or more white blood cell types (e.g., neutrophils, lymphocytes, monocytes, eosinophils, and/or basophils) may be detectable by suitable capillary selection as described herein.

In some embodiments, for every capillary of the second set of capillaries, the controller 2350 detects one or more cellular events that flow through that capillary as follows. In some embodiments, the controller 2350 loads all the images showing the capillary as a 3D matrix into the memory 2360 and/or the database 2370, with matrix dimensions associated with to the x pixel location, the y pixel location, and the image. Every matrix value corresponds to a brightness level for that pixel. In some embodiments, the controller normalizes the brightness level of the 3D matrix by a) normalizing the brightness level spatially with respect to the first image showing that capillary to compensate for potential brightness variations associated with the illumination source 2320. In some embodiments, this is accomplished by a) flattening individual images by dividing (for each pixel) the pixel brightness by local brightness averages estimated with a Gaussian filter with a standard deviation of 25 pixels, and b) adjusting the average brightness of every image showing that capillary such that brightness values remain closest to those in the first image showing that capillary (in terms of mean-squared error).

Each pixel in this preprocessed, normalized 3D matrix has a time-signal associated with it that will be similar for all pixels under which the same cellular event passes; the main difference between these pixels will be a pixel specific time shift. Another difference is that not all time signals are equally strong/of adequate amplitude. As a first approximation, the controller 2350 chooses a pixel away from the edge of the image with the 'strongest' time-signal to be a reference pixel. Generally, a strong/desirable signal is one having a large contrast between the bright gaps (indicative of likely presence of a white blood cell) and the dark red blood cells such as, for example, a contrast that exceeds the noise level in the signal by a predetermined threshold. This signal can be a candidate reference signal for temporal alignment. In some embodiments, the controller estimates the strength of this candidate reference signal based on the ratio between the sum of its squared values and the sum of its absolute values; this ratio can be interpreted as an estimation of the strength of its peaks relative to its nominal fluctuations. In some embodiments, the reference signal estimation can employ the following pre- and post-normalization steps: (a) local temporal averages are subtracted from the time signals based on an averaging window (e.g., a window size of 200 ms), (b) for robustness, the aforementioned ratio is estimated as the median of 10 estimates from 10 successive time chunks of same size, (c) the resulting ratio estimates, which form a 2D map for the set of images showing the capillary, are further filtered spatially (across the spatial dimensions) with a Gaussian filter with standard deviation of 1 pixel. In some embodiments, the controller 2350 ignores and/or does not otherwise account for other capillaries near the edge of the region-of-interest, as there may be intensity fluctuations due to imperfect registration, by introducing a weighting factor to penalize reference-pixel candidates that are near the border of the frame. The controller 2350 then chooses the pixel that maximizes the product of the peak intensity of the preprocessed time-signal and its distance from the edge of the region of interest.

In some embodiments, the controller 2350 further filters out other structures that are not likely to be a cellular event through spatial filtering of every separate frame. In some embodiments, this is accomplished by, for every frame, applying a band-pass filter in the discrete Fourier domain to remove all features of unsuitable size, the low-frequency and high-frequency band-pass parameters being adjusted to fit the range of expected cellular event sizes/expected white blood cell size.

In some embodiments, the controller 2350 further sets the intensity of a red-blood-cell-filled capillary to zero. The goal of this step is to ensure that flow without events will display proper contrast with respect to the passage of events, the latter being then ideally associated with (significant) non-zero brightness values after bias removal. In some embodiments, the controller accomplishes this by subtracting the temporal (frame-wise) medians from all corresponding pixels in all images showing that capillary. The pixel-wise operation is performed on all pixels separately and indiscriminately, i.e., independently of whether the pixels are inside or outside a capillary. An assumption of this step is that a capillary is filled with red blood cells for most of its length, and for most of the time.

The controller 2350 then compares the time-signal that is associated with every pixel location of the images showing the capillary of the second set of capillaries to the reference time signal at the reference pixel, that was estimated as disclosed herein. First, the controller 2350 suppresses long-term intensity fluctuations by applying a high-pass filter to every separate time signal along the time dimension. The controller 2350 then estimates the correlation between every time signal and the reference time signal, which results in an amplitude and a phase value for each pixel. A large positive amplitude indicates a strong correlation, and the phase indicates the time shift with respect to the signal at the reference pixel. This per-pixel amplitude and phase information is used as described below to estimate an averaged signal that is more robust to noise. The controller 2350 performs all operations by replicating the first and last frame to avoid false detections at the start or end of the sequence of images showing the capillary.

Based on the reference time signal and on the other times signals with associated phase and amplitude correlation information, the controller 2350 generates an averaged time signal that is relatively more robust to noise. This averaged time signal combines all time signals that are deemed to be part of the capillary. In some embodiments, the controller 2350 retains any time signals where a) their correlation with the reference signal exceed the reference-signal autocorrelation times a threshold value, and b) the time signal's (positive or negative) time delay with respect to the reference signal (i.e., the phase) is no larger than the maximum time that a gap/cellular event takes to flow through the capillary, which is a relatively fixed parameter.

Figure 26A:
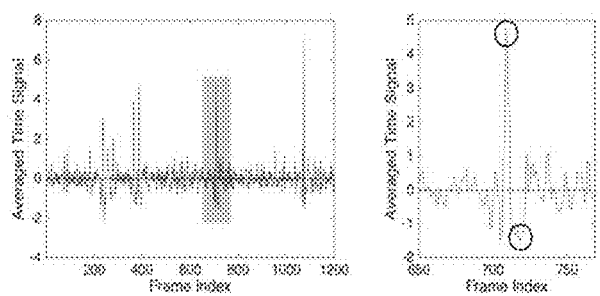
FIGS. 26A-26C illustrate an averaged time signal.
Figure 26B:
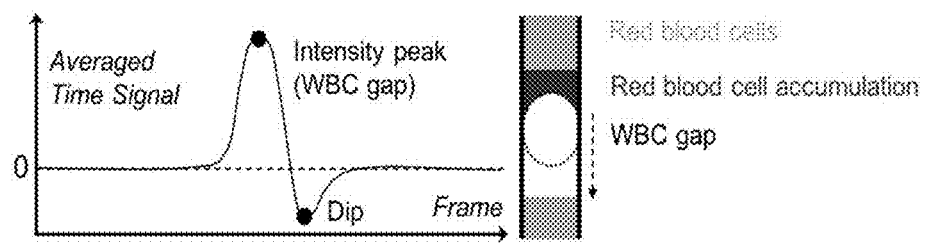
Figure 26C:
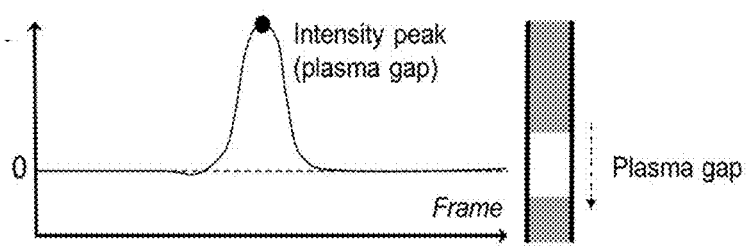

The controller 2350 then calculates a superior reference time signal as follows: (a) all time signals are aligned in time with respect to the reference time signal, based on the phase information, (b) the aligned time signals are averaged, (c) the resulting averaged signal is high-pass-filtered in time, based on a fixed minimum-frequency parameter. The resulting filtered one-dimensional signal is useful for detection of cellular events, noting that the time at which cellular events are detected is associated with the reference pixel position. FIGS. 26A-C illustrates an example of a real time signal produced by analyzing a set of images for one capillary, and also shows the types of time-signal profiles that can be expected around a single cellular event versus a plasma gap. It is hypothesized that gaps containing a white blood cell have a higher concentration of red blood cells, corresponding to a darker area, upstream, as best illustrated in FIG. 26B.

Each gap/cellular event is associated with an uninterrupted stream of values for which the averaged time signal, which reflects the spatially averaged normalized brightness in the capillary, exceeds a threshold value. While all non-zero values should reflect a passing event, due to noise, the threshold value can be set as a non-zero, positive value. In some embodiments, the threshold value is optimized to achieve the best possible separation between the signal and the noise. For example, in some embodiments, the threshold value is set to capture most peak signal information (associated with values above that threshold) while rejecting most noise artefacts (associated with values below that threshold). In some embodiments, the controller 2350 sets this threshold value as a multiple of the noise's standard deviation, where the noise is estimated following a positive exponential model (i.e., a decaying exponential is fitted to the positive part of the signal distribution). In some embodiments, the standard deviation of the signal itself can serve as a noise estimate. In some embodiments, before thresholding, the controller checks the averaged time signal to avoid repeated spurious event detections: specifically, if the ratio between the median-filtered version of the signal (e.g., with filter size of 240 frames) and the first-quartile thereof exceeds unity, the controller locally divides the signal by this ratio. For each detected gap/cellular event, associated time information is defined with respect to the reference pixel; if the signal exceeds the threshold for more than one image showing that capillary, the controller chooses the center image in the series of images showing that capillary.

In some embodiments, the controller maps the cellular events back to a series of x, y, and t in the 3D matrix, maximum one per image for that capillary. Each cellular event can occur in multiple images, a number that depends on the flow speed, capillary length, and the frame rate of the acquisition. The ability to detect a cellular event is limited by the maximum crossing time of a gap around the reference frame, the frame in which the gap passed the reference pixel. For each image, controller 2350 marks the brightest pixel that is deemed to be inside the capillary.

For each capillary of the second set of capillaries, the controller 2350 then generates an associated event count. As described in more detail herein, in some embodiments, after averaging the event count across all capillaries in the second set of capillaries, each set of images can be can be used for classification of the user.

Figure 27A:
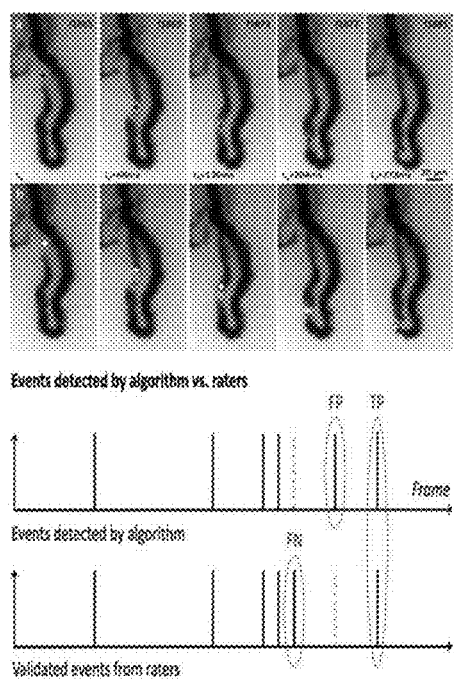
FIGS. 27A-27B illustrate cellular event detection by automated approach vs manual raters.
Figure 27B:
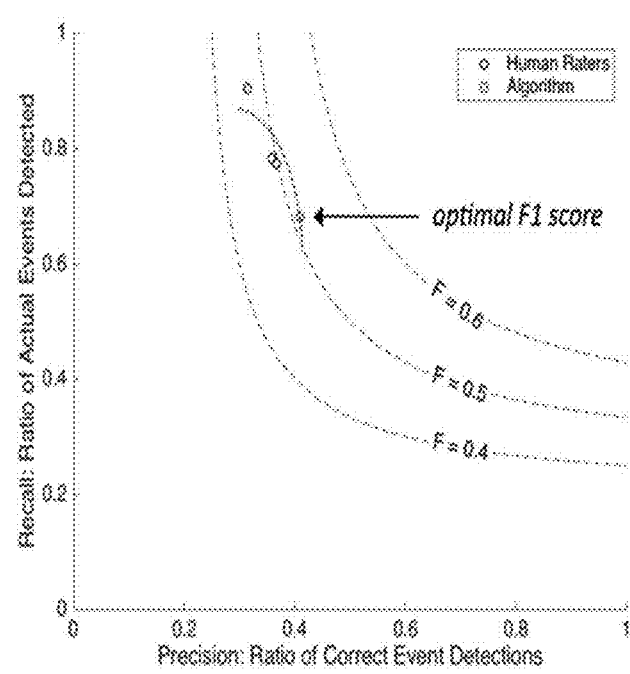
Figure 28A:
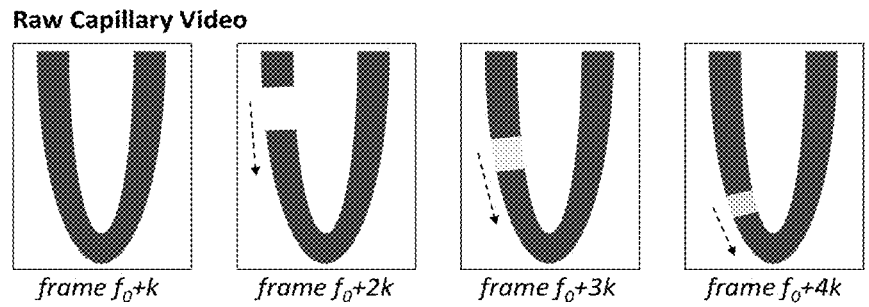
FIGS. 28A-28D illustrate an example event detection method/approach.
Figure 28B:
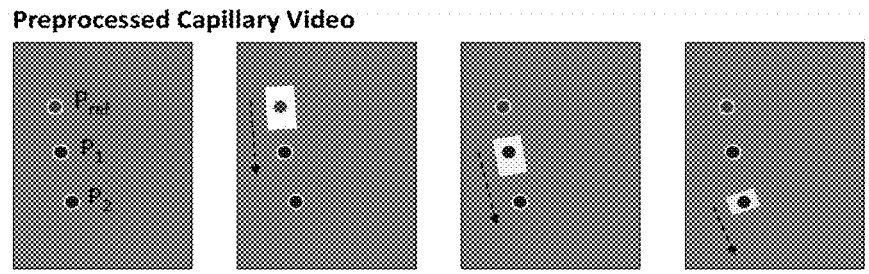
Figure 28C:
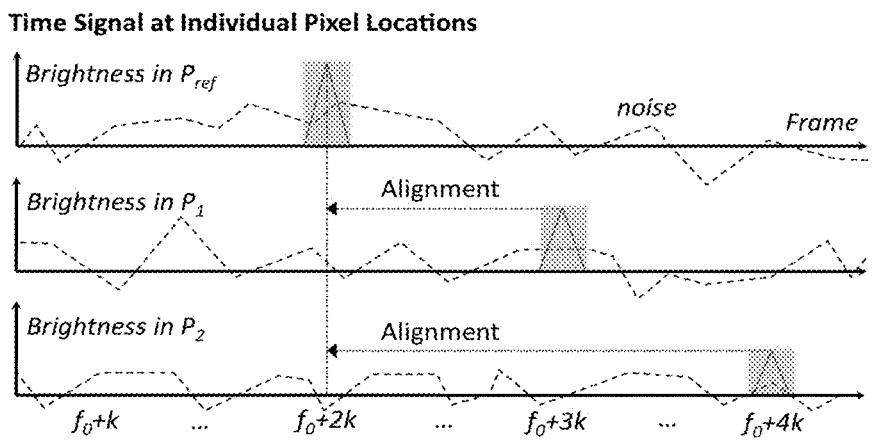
Figure 28D:
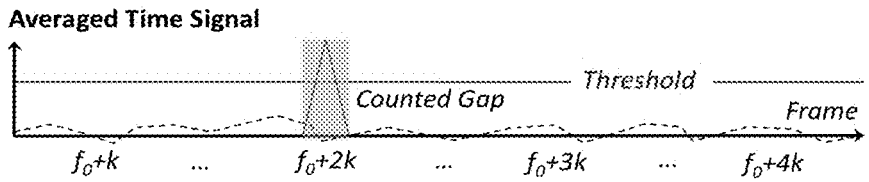

FIGS. 27A-27B illustrate results from cellular event detection on 26 raw videos/sets of images, with comparison to human raters. Comparing against one of the individual raters, F1 score is used as a metric measuring the consistency of the detected events (defined as the harmonic mean of precision P and recall R, where P=TP/(TP+FP) and R=TP/(TP+FN)). For individual experts (3 in total), the F1 score was evaluated against the cellular events consistently detected by the rest of experts (i.e., groups of 2). For the embodiments disclosed herein, the F1 score was evaluated as an average between the results with respect to these 3 groups of 2 experts, which ensured an unbiased comparison. The F1 score takes true positives, false positives, and false negatives into account.

FIGS. 28A-28D illustrate an example, overall approach to cellular event detection as described herein with respect to the controller 2350.

Referring again to FIG. 23, in some embodiments, the controller 2350, based on the number of cellular events detected in the second set of capillaries, classifies the user to a user type of a set of user types. In some embodiments, at least one of the user types is associated with a diagnosis of neutropenia (absolute neutrophil count <500 cells/up, and at least one other user type is associated with the user not being neutropenic. In some embodiments, the controller 2350 executes a weighting approach (i.e., employing a weighted average of event count across all capillaries) to improve classification quality. In some embodiments, the weighting approach can be based on the estimated quality of the set of images.

In some embodiments, the controller 2350 generates a single event index value (also sometimes referred to as a "Leuko-index value") summarizing all event counts. In some embodiments, the controller compares the event index value against an event threshold that can (in some embodiments) be a learned parameter, as described in more detail herein. The classification of the user to a user type (e.g., a first user type) associated with severe neutropenia is if the event index value $<\mu$, and to another user type (e.g., a second user type). While described herein for two user types, it is understood that the controller 2350 can classify the user to three, four, or more user types, depending on the thresholding parameter(s).

As noted herein, the controller 2350 can assign weights to each capillary of the second set of capillaries based on the estimated quality of that capillary. As an example, in some embodiments, the weight for a capillary can beset to $\frac{1}{10}$ if the threshold used to detect events was greater than a fixed level relative to the standard deviation of the signal (which indicated a lower quality) and to 1 otherwise.

As noted above, in some embodiments, the event threshold can be a learned parameter. For example, in some embodiments, the event threshold was determined based on a total of 116 raw videos/sets of images. Specifically, a total of 116 imaging sessions (mostly associated with 1 raw video/set of images each) from 42 patients were employed. From these sessions, 60 corresponded to a reference blood-draw value of ANC<500 and 56 to ANC>500 (15 of which to 500<ANC<1,500). In cases where consecutive daily blood draws showed a transition from ANC<500 to ANC>500, the imaging session took place within 8 hours of the first one.

Figures 29A, 29B:
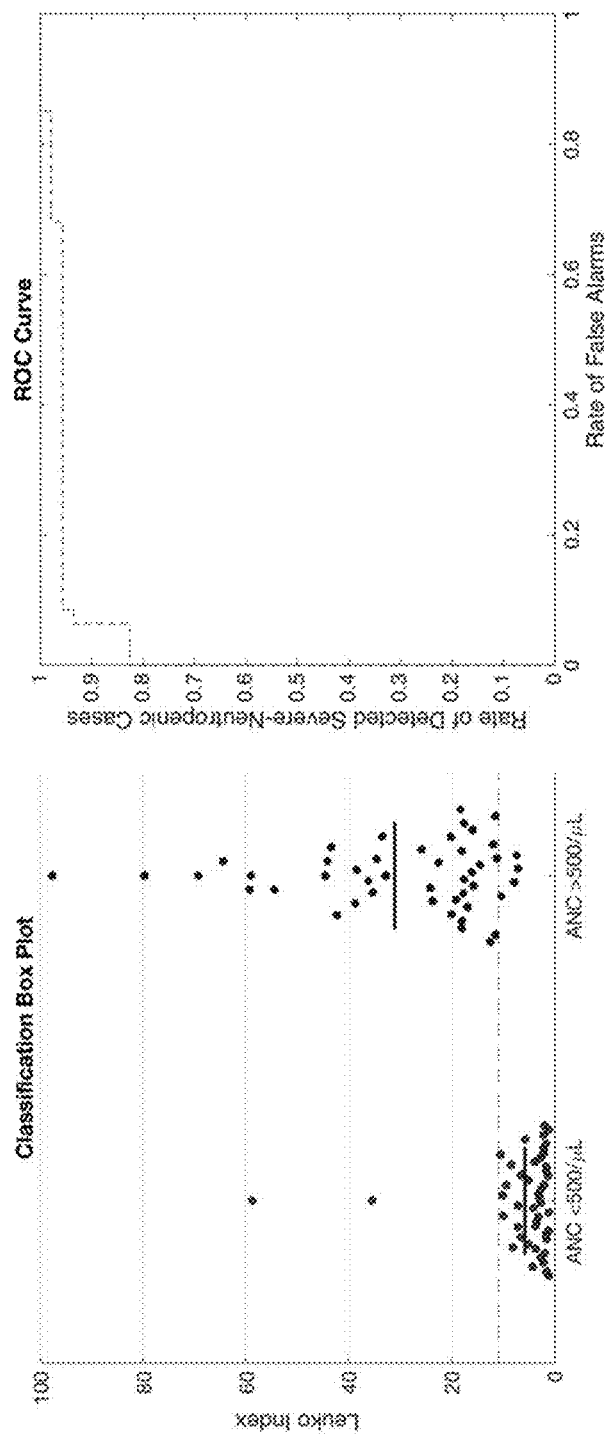
FIGS. 29A-29B illustrate classification results generated by the full automated approach as disclosed herein on 116 data points.
Figures 61A, 61B:
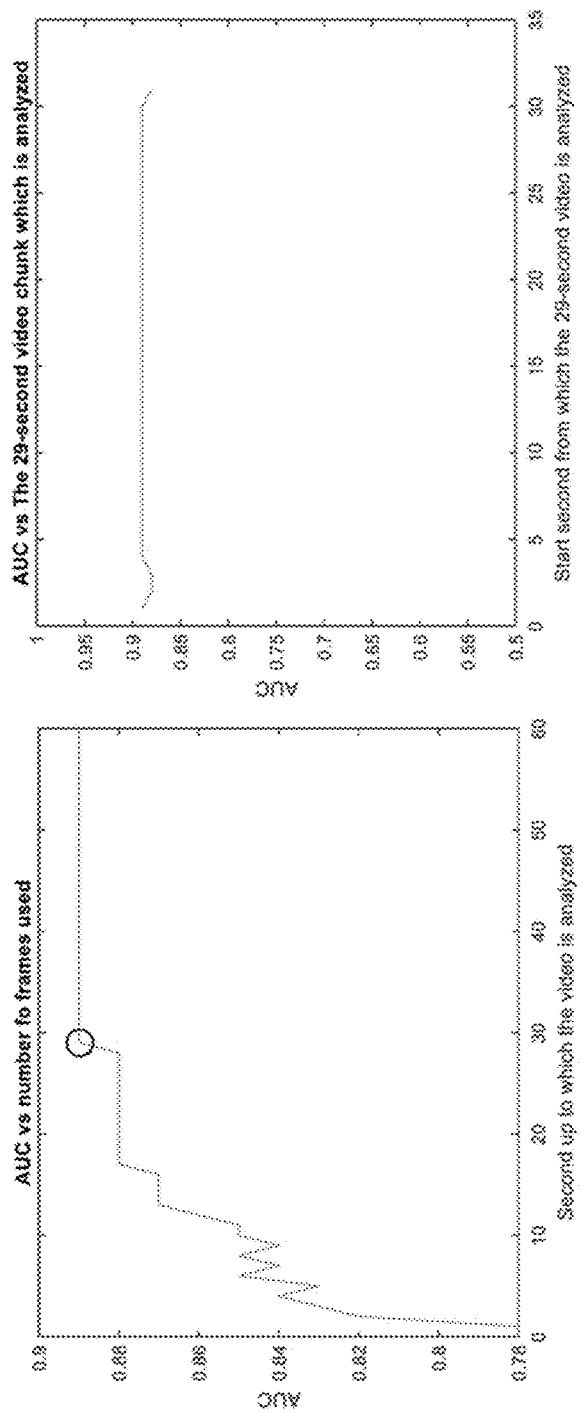
FIGS. 61A-61B illustrate classification results for video segments of a specific duration.

FIGS. 29A-29B shows results from classification of the aforementioned data using the systems, devices, and methods disclosed herein. A performance of 9% of false alarms (i.e., 9% of cases wrongly deemed severely neutropenic) under a 96% rate of detected severe neutropenia (AUC=0.96) was obtained. In these results, 20% of sessions were deemed unsuitable during analysis and were thus discarded. The corresponding conditions are: (a) no session with <3 detected capillaries, (b) no session with zero Leuko index: individual capillaries (i.e., individual capillaries with no detected events) being also discarded as part of (b). FIGS. 61A-61B illustrates how classification can be affected by the length of the video/number of images in the set of images employed.

FIG. 30 illustrates a method 3000 for non-invasive hematological measurements, according to some embodiments.

The method 3000 can be carried out by the system 2300, or a structurally and/or functionally similar variant thereof. The method 3000 includes, at 3100, acquiring a set of images of at least a nailfold portion of a finger of a user. In some embodiments, step 3100 further includes acquiring the set of images as a set of frames of a video. In some embodiments, the method 3000 further includes illuminating the nailfold portion, the acquiring the set of images being in response to the illumination of the nailfold portion.

The method 3000 further includes, at 3200, detecting, in each image of the set of images, one or more capillaries in the nailfold portion of the finger to identify a first set of capillaries across the set of images. The detecting can include estimating one or more attributes of each capillary of the first set of capillaries. The one or more attributes includes one or more structural attributes, one or more flow attributes, one or more imaging attributes, or combinations thereof, such that a first attribute of the one or more attributes of each capillary of the first set of capillaries meets a predetermined criterion for the first attribute. In some embodiments, the one or more structural attributes selected from the group consisting of average capillary diameter, lateral capillary diameter, vertical capillary diameter, capillary length, capillary shape, and/or the like. In some embodiments, the one or more flow attributes is selected from the group consisting of blood flow speed in the capillary, transit time for a cell within the visible portion of the capillary, volumetric flow rate, mass flow rate, and/or the like. In some embodiments, the one or more imaging attributes selected from the group consisting of contrast, focus, signal-to-noise ratio, image stability, and/or the like. In some embodiments, the first attribute is average capillary diameter, wherein each capillary of the second set of capillaries has an estimated average capillary diameter from about 10 µm to about 20 µm.

In some embodiments, the method 3000 can further include generating a confidence value associated with the image of each capillary of the first set of capillaries in the set of images. The first set of capillaries can include those capillaries for which the confidence value, for each image in which that capillary is detected, exceeds a confidence threshold.

In some embodiments, the method 3000 can further include receiving a set of training images including a specification of one or more capillaries visible within each image of the set of training images. The method 3000 can further include training a neural network on the set of training images, and applying the set of images to the neutral network to detect the first set of capillaries.

In some embodiments, the detecting the first set of capillaries further including applying the set of images to a neutral network, the neural network being trained on a set of training images including a specification of one or more capillaries visible within each image of the set of training images.

The method 3000 further includes, at 3300, identifying a second set of capillaries from the first set of capillaries such that each capillary of the second set of capillaries is visible in a predetermined number of images of the set of images.

In some embodiments, the method 3000 further includes detecting, for the set of images and in the second set of capillaries, a set of cellular events. Each cellular event of the set of cellular events is associated with passage of a white blood cell in a capillary of the second set of capillaries. The method 3000 can further include estimating an event count for the second set of capillaries based on the set of cellular events.

In some embodiments, the method 3000 further includes, for each capillary of the second set of capillaries, estimating a quality factor. The method 3000 can further include estimating the event count based on the set of cellular events and the quality factor associated with each capillary of the second set of capillaries.

In some embodiments, the method 3000 further includes receiving a set of training images associated with nailfold portions of a set of training users. The method 3000 can further include generating, via supervised learning, an event count threshold based on the set of training images. The method 3000 can further include classifying the user to a first user type of a set of user types based on the event count and the event count threshold, at least one user type of the set of user types associated with a diagnosis of neutropenia. The method 3000 can further include transmitting an indication of the first user type to the user (e.g., via an interface of the system 2300, of the device 2340.

Additional detail on various embodiments of the systems, devices, and methods as laid out herein are provided below.

Volumetric Estimation and Capillary Sub-Selection for Improved Accuracy of Counts As described above (e.g., with reference to Equation (8)), the WBC concentration can be estimated based on the estimation of the number of WBC cells (e.g., as estimated by the number of cellular events) and the volume of blood passing through the capillary of interest during the total video-acquisition time. The total blood volume passing through a given capillary section usually depends on the local diameter of the capillary section and the average local speed of the blood. In addition, the conservation of volume (or conservation of the mass of the blood) indicates that the total blood volume of interest can be maintained at a constant value during propagating within the capillary. In other words, the total blood volume can be a constant independent of the capillary section that is considered. Therefore, the estimation of the volume of a capillary section can be employed as an estimation of the blood volume of interest.

Based on this observation, a method of robust volumetric estimation is based on cross-correlation or optical flow techniques.

At least two approaches can be used to estimate the volume of a capillary section. In one approach, it can be assumed that the capillary section at issue has a perfectly cylindrical shape. In this case, the width of the capillary, as acquired from the video or image, can be used also as the depth of the capillary.

In another approach, a method of estimating the volume of a capillary section is performed based on the analysis of pixel-intensity values. Specifically, the capillary depth at a given position in the image plane is expected to inversely correlate with the measured light intensity due to light absorption. The vertical and horizontal diameter of the capillary may not be equal, meaning that diameter of the visible projection may not be representative of the vertical diameter. In other words, a lower pixel value indicates a larger value of capillary depth and vice versa. Accordingly, this resolved depth estimation can be used to more accurately compute the cross sectional area of the capillary section.

FIGS. 31A-31F illustrate a method of estimating the volume of a capillary section based on analysis of pixel intensities. In some embodiment, some or all aspects of the method of FIGS. 31A-31F can be executed by one or more of the systems, apparatuses, and devices as described herein such as, for example, the system 2300 and/or the device 2340.

FIGS. 31A and 31B show two images of capillary sections, where the pixel value is FIG. 31A is greater than the pixel value in FIG. 31B (i.e. FIG. 31A is brighter). The two capillary sections have the same width of about 15 µm at a given location indicated in FIGS. 31A and 31B. In conventional methods, this width is also used as the depth of the capillary sections and the reconstructed capillary cross sections are perfectly round, as shown in FIGS. 31C and 31D. In contrast, when the pixel intensities are taken into account, the different pixel values indicate that the depths of the two capillary sections are different. FIGS. 31E and 31F show the reconstructed cross sections corresponding to the capillary sections shown in FIGS. 31A and 31B, respectively, using the method based on pixel intensity analysis. As seen from FIGS. 31E and 31F, the larger pixel value in FIG. 31A indicates a smaller depth, while the lower pixel value in FIG. 31B indicates a greater depth. The cross sectional shapes of the two capillary sections are now elliptical instead of being circular.

The same analysis can be performed along the entire capillary shown in FIGS. 31A and 31B and a cross sectional area A as a function of the curvilinear coordinate (e.g., length 1) can be acquired. The total volume of the capillary V can then be calculated by taking the integral of A(l) with respect to l, i.e., $V=\int A(l)dl$.

The volume calculated from the above method can also be used for volume resampling of the capillary profile. This method can analyze the flow speed in one given capillary using a one-dimensional curvilinear coordinate system. In one example, coordinates in a one-dimensional curvilinear coordinate system are usually a function of length along the capillary (see, e.g., FIGS. 6A and 6B and descriptions above). In another example, the coordinates in a one-dimensional curvilinear coordinate system can be a function of the cumulative capillary volume. One advantage of resampling coordinates according to the cumulative capillary volume is that the particle/event speed can become constant in the particular coordinate system, thereby facilitating accurate estimation using cross-correlation or similar techniques.

FIGS. 32A-32C illustrate volume resampling of a capillary profile. FIG. 32A shows a representation of a capillary having a constant blood flow speed but varying diameters along the capillary length. Due to light absorption, red blood cells are represented in black whereas a single white blood cell squeezing through the capillary is represented in white. FIG. 32B shows a spatio-temporal map representing the gray-scale values (color map from blue—dark—to red—bright—) along the linear capillary length (y-axis) across time (x-axis). FIG. 32C shows a spatio-temporal map acquired using volume resampling and the map is shown with the capillary length coordinates (y-axis) as a function of the cumulative capillary volume at each cross-section in FIG. 32A. In this case, the white blood cell trajectory (red—bright— line) at constant speeds becomes a straight line thus being easier and more accurate to estimate using cross-correlation or similar techniques.

Sub-Selection of Capillary Events

Further improvement of WBC detection and estimation (e.g., as generally described herein with respect to FIGS. 23-30) can be achieved via sub-selection of capillaries whose events are most easily detectable and most likely to correlate with the presence of WBCs. The sub-selection of capillary events can be carried out according to several criterions.

Figure 33:
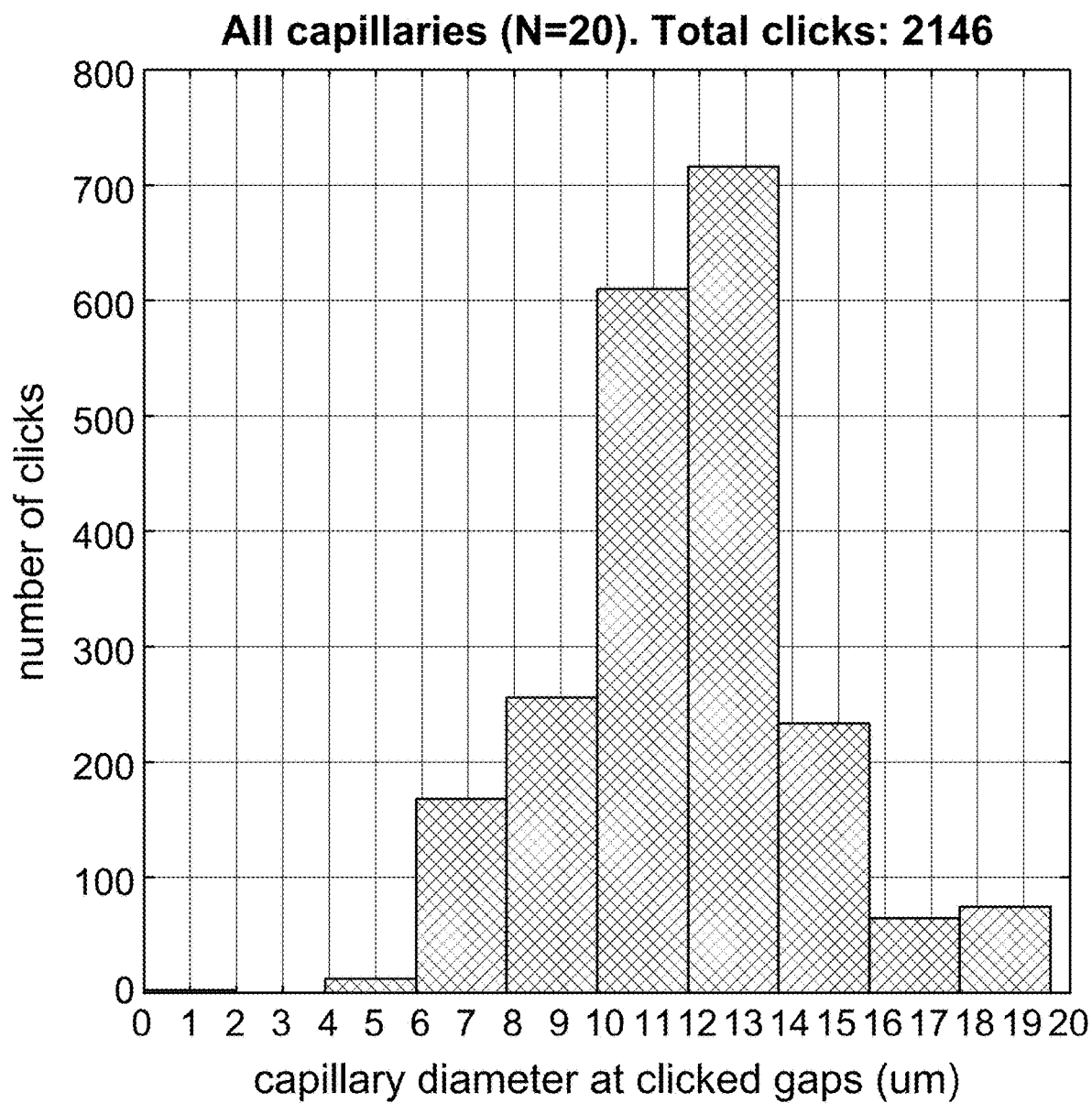
FIG. 33 illustrate sub-selection of capillaries based on observed size.

In one example, the sub-selection can be according to the observed size, i.e., average diameter and/or diameter profile. The size usually correlates with the presence of clear, high-contrast, and whole-capillary-diameter events for a given range, such as the range between about 10 µm and about 20 µm). FIG. 33 shows the range of capillary diameters with the presence of clear gaps. Sub-selecting capillaries based on their diameter can improve correlation with WBCs.

Figure 34A:
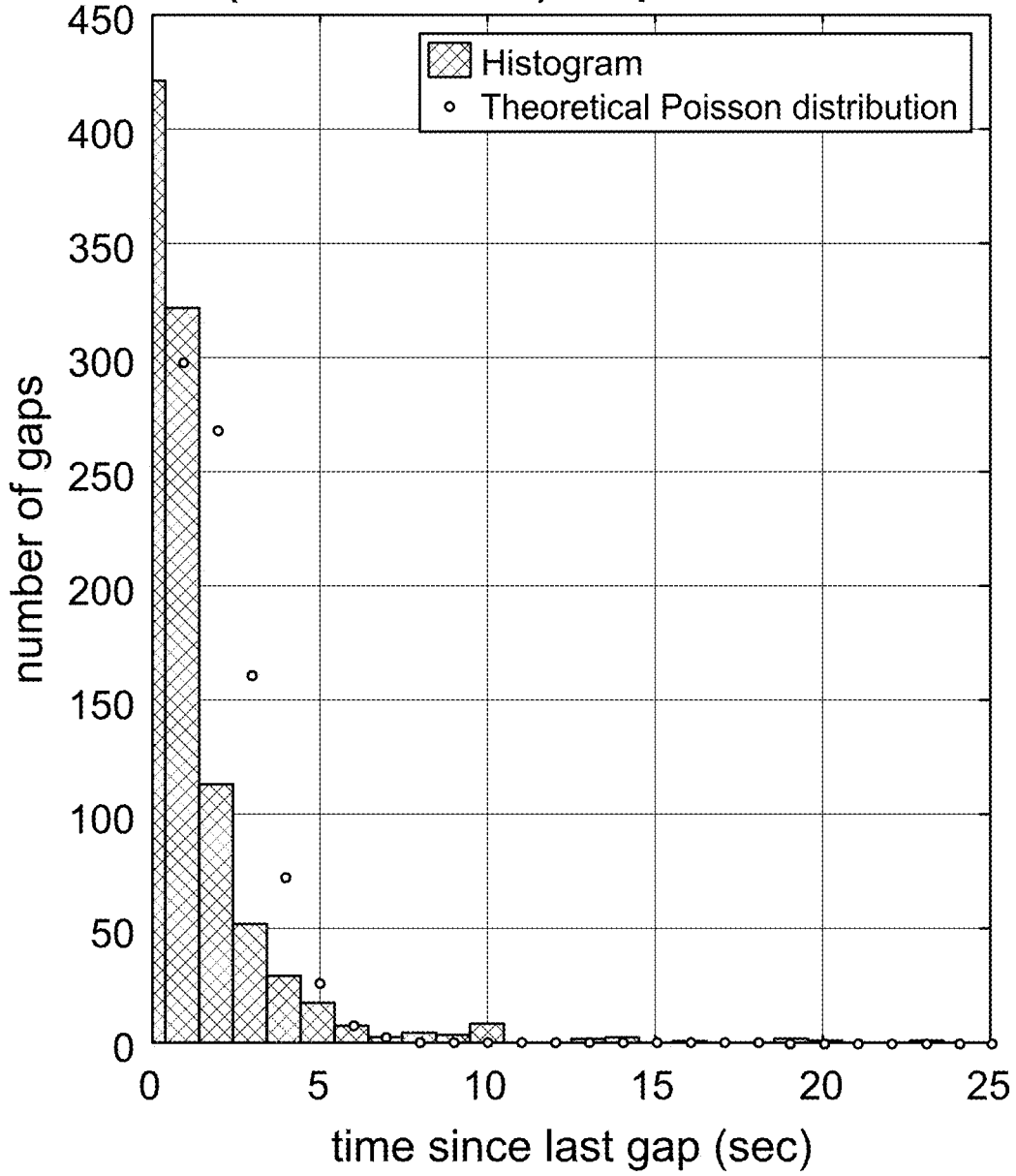
FIGS. 34A and 34B illustrate sub-selection of capillaries based on the distribution of time of arrival between observed gaps.
Figure 34B:
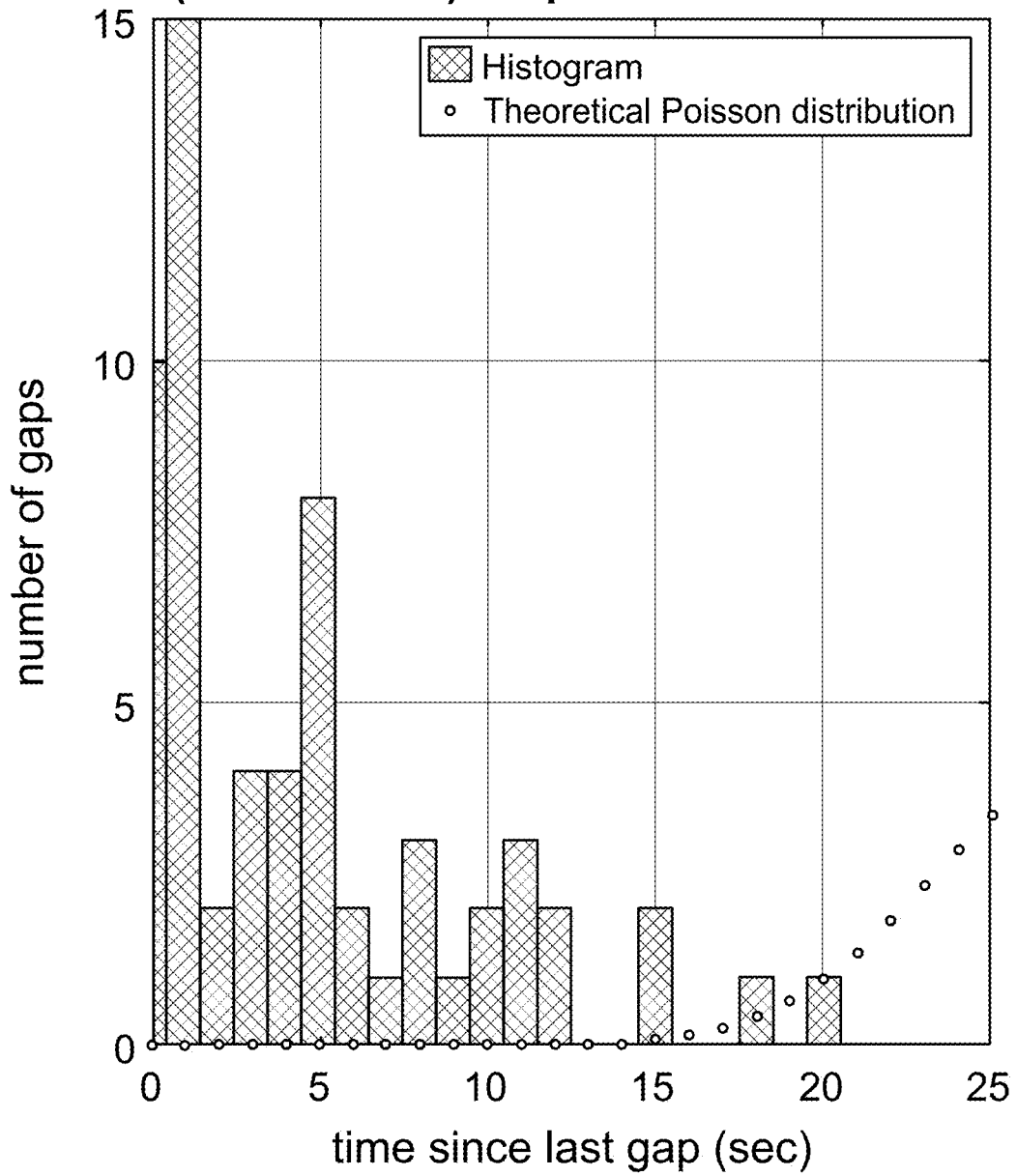

In another example, the sub-selection can be according to the temporal distribution in the arrival of clear, high-contrast, and whole-capillary-diameter events, which are showed to be different in the presence/absence of white blood cells. FIG. 34A shows the distribution of the time of arrival (TOA) between gaps in a sample with 5,500 WBC/µL. With this high concentration of WBC, the TOA substantially follows a Poisson distribution. In contrast, FIG. 34B shows the distribution of TOA between gaps in a sample with 100 WBC WBC/µL, much lower than the concentration shown in FIG. 34A.

In yet another example, the sub-selection can be performed according to the dynamical behavior of the capillaries. In this approach, a method can directly sub-select capillaries based on the event features, including length, contrast-to-noise ratio, and speed. For example, clogging effects can be identified as being due to red blood cells in some small-diameter capillaries.

Figures 35A, 35B, 35C:
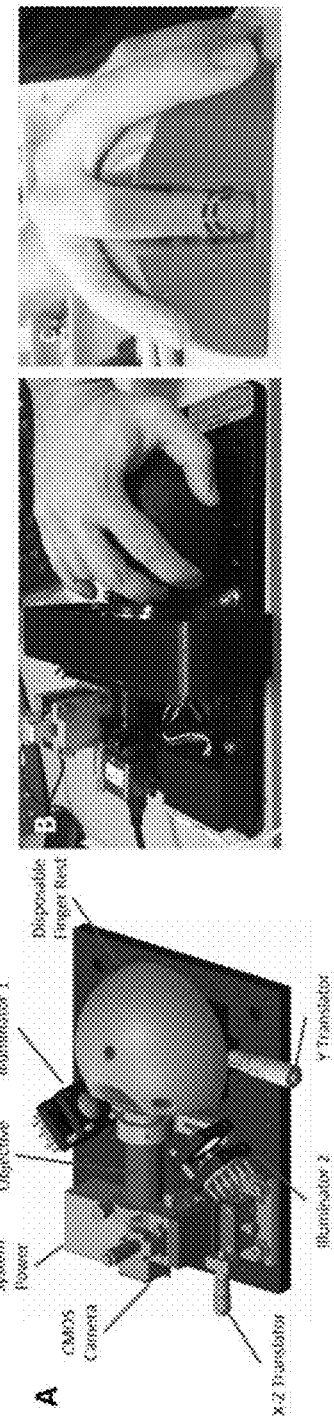
FIGS. 35A-35C illustrate an apparatus for detecting severe neutropenia based on images of nailfold capillaries.

Acquisition of High-Speed, High-Contrast, and Stable Videos of Multiple Nailfold Capillaries FIGS. 35A-35C illustrate an apparatus for detecting severe neutropenia based on images of nailfold capillaries. In some embodiment, some or all aspects of the apparatus of FIGS. 35A-35C can be structurally and/or functionally similar to one or more of the systems, apparatuses, and devices as described herein such as, for example, the system 2300 and/or the device 2340.

FIG. 35A shows a rendered 3D model of the apparatus employed to record microscopy videos of the microcirculation in nailfold capillaries of patients, with its different components. FIG. 35B illustrates that patients place their ring finger in a 3D-printed holder, which plays a dual role: achieving stability throughout the one-minute recording duration and holding the oil employed for optical coupling. FIG. 35C shows that the finger is placed in such a way that illumination and imaging is directed at the nailfold area (purple circled area as indicated in the figure).

Figure 36:
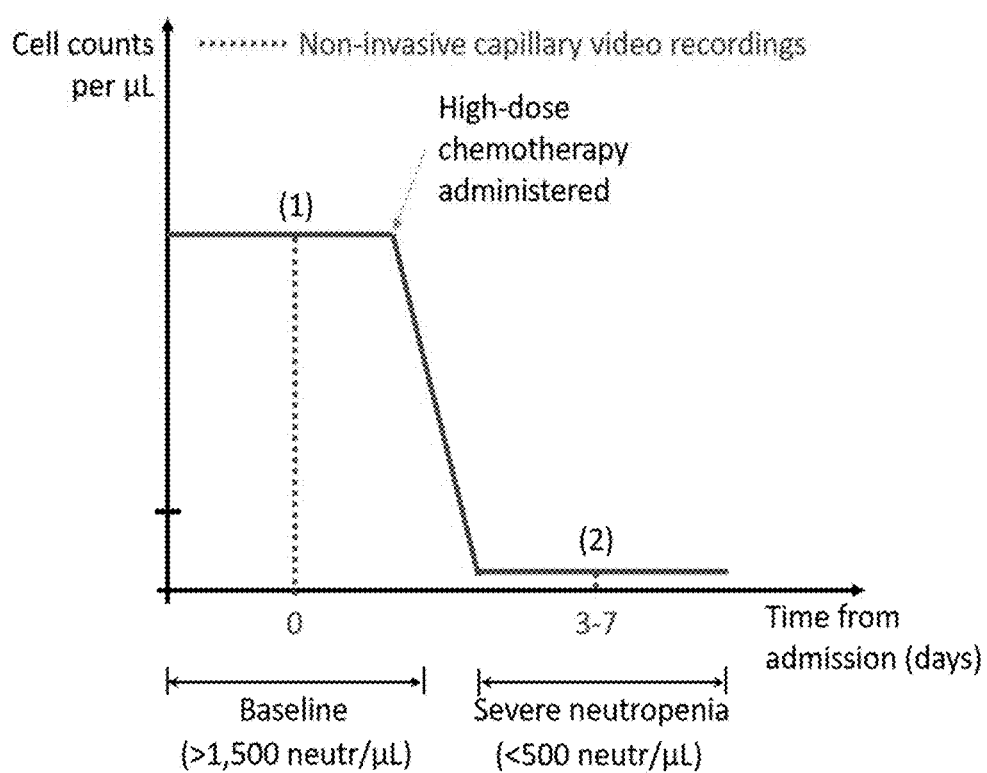
FIG. 36 illustrates two different timing points to acquire images from patients in a clinical study using the apparatus shown in FIG. 35A.

The apparatus shown in FIG. 35A can be used to record high-quality microscopy videos of the microcirculation in human nailfold capillaries, and employed it on ASCT patients (see, FIG. 36). The patient's finger is inserted from the top into the well of a 3D-printed semi-spherical easily-sanitized hand rest (FIG. 35B), which is designed to ergonomically hold the patient's hand with sufficient stability to record one-minute videos. Capillary videos are acquired from the nailfold region in the finger of a subject (FIG. 35C).

Figures 37A, 37B:
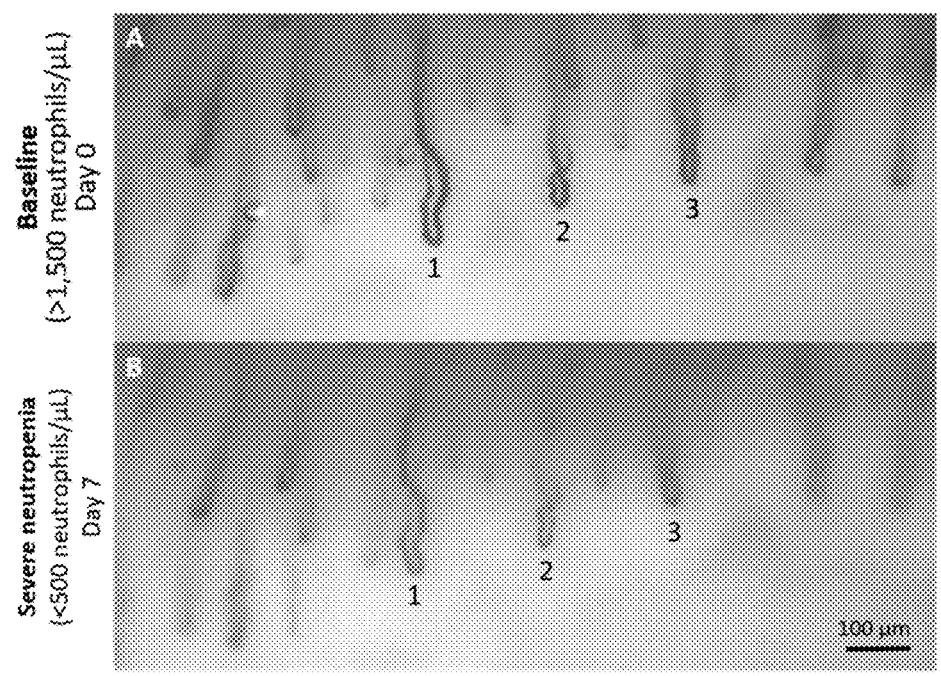
FIGS. 37A and 37B show examples of raw images acquired by the apparatus shown in FIG. 35A.

FIGS. 37A and 37B show examples of raw images acquired by the apparatus shown in FIG. 35A. The pair of wide-field videos was acquired with the apparatus from one ASCT patient at two time points where the same capillaries can be observed (three numbered pairs shown). FIG. 37A shows the image taken with baseline neutrophil concentration (i.e., greater than 1,500/µL) and FIG. 37B shows the image taken with when the patient had severe neutropenia (neutrophils concentration less than 500/µL). The scale bar in the images is 100 µm.

It can be seen from FIGS. 37A and 37B that the apparatus can optically capture capillary-nailfold videos with appropriate contrast, resolution, stability, and depth of focus. Raw videos acquired with the apparatus contain multiple capillaries within the field of view. The acquisition of several capillaries was made particularly convenient with this simple optical approach which allowed imaging of multiple capillaries at a time in the same field of view. In contrast, many existing techniques, such as encoded confocal microscopy (SECM), can only image a single capillary at one time.

FIGS. 38A-38E illustrate an example of optical gap flowing in a capillary. The image sequence shows several raw frames of a video centered on one capillary acquired with the apparatus on one of the patients at baseline. The dark loop corresponds to the capillary vessel filled with RBCs that absorb light at the illumination wavelength. An optical absorption gap in the microcirculation, approximately the same size as the capillary width (about 15 μm) can be observed flowing through the arterial limb of the capillary (indicated as black arrowheads). Frame numbers are labeled at the top right corner. The frame rate was 60 frames per second and the exposure time was 16.7 ms. The contrast was adjusted for the region of interest shown.

These capillaries in the acquired images are very narrow, with typical widths of about 10 μm to about 20 μm. In this case, the WBCs are typically forced to squeeze through the capillaries one by one. Focusing in on a single capillary, the frames reveal the passage of an event in the microcirculation, which can be perceived as a moving "bright" object, approximately of the same size as the capillary diameter (about 15 μm). The bright object (or a gap in the dark background) has a brightness that is significantly higher than the surrounding RBCs and therefore can be readily observed and monitored.

The event movement can be clearly followed across successive frames and, as such, are visually identifiable by a human observer. Accordingly, all events in the capillary videos were marked and labeled by three blinded human raters, following specific visual criteria (see more details below). Spatio-temporal (ST) maps provide a convenient alternative representation for showing all event trajectories with the marks from these raters in the one-minute capillary videos.

Figures 39A, 39B, 39C, 39D, 39E:
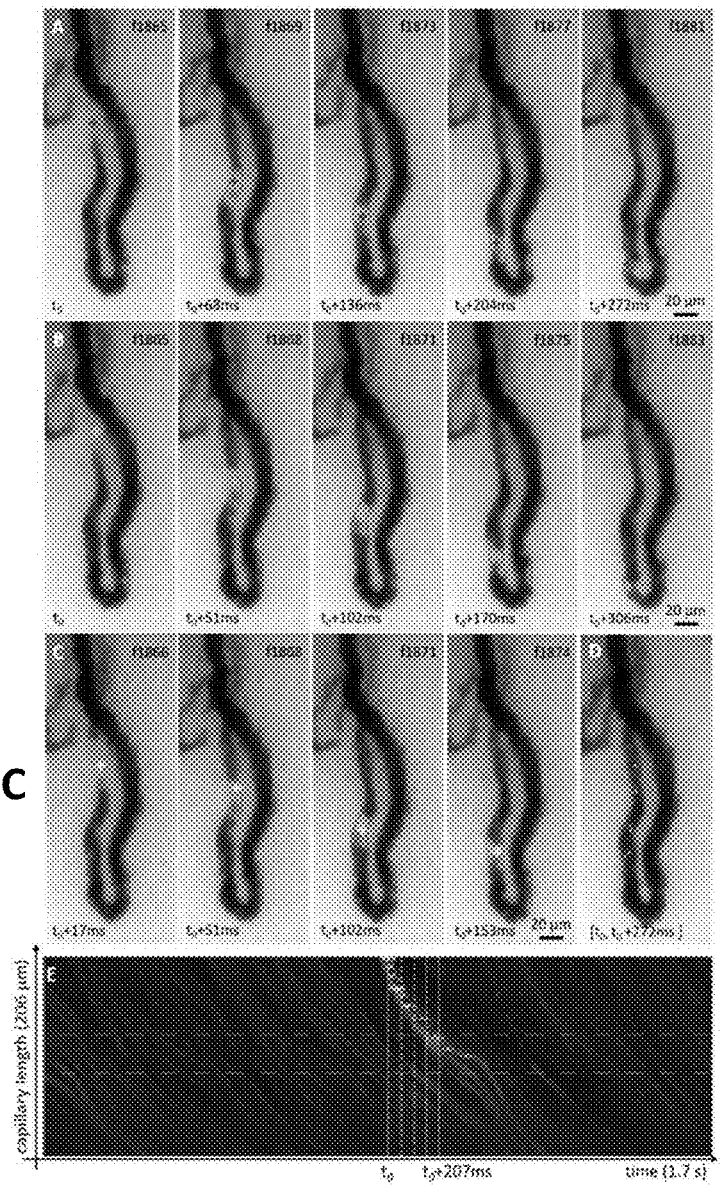
FIGS. 39A-39E show results of blind event rating using the images acquired by the apparatus shown in FIG. 35A.

FIGS. 39A-39E show results of blind event rating using the images acquired by the apparatus shown in FIG. 35A. Three human raters independently labeled one event they observed in one of the 98 capillaries employed in the study. FIGS. 39A-39C show capillary-video frames (indexed at top right) with cross-shaped event marks from rater 1 (blue), 2 (green) and 3 (yellow). FIG. 39D shows aggregated positions of all event marks from all three raters. FIG. 39E shows an ST map displaying the recorded brightness levels along the segmented capillary length (vertical axis) as a function of time (horizontal axis) for a 1.7-second interval around the event of interest. A bright trajectory created by the passage of the event can be clearly identified in the center of the ST map. Blue, green, and yellow crosses correspond to the spatio-temporal coordinates where each of the three raters labeled the event. Event trajectories visible on the ST map correspond well with events identified by the raters from the videos.

Microcirculation Events with Specific Features can be Used as Proxies of WBC

FIG. 36 illustrates two different timing points to acquire images from patients in the clinical study. The patients enrolled in the study are undergoing an ASCT, process that results in a very predictable evolution of their neutrophil counts due to the controlled administration of chemotherapy. This provides an opportunity to record capillary videos at two different time points for each patient: (1) baseline (>1,500 neutrophils/μL) and (2) severe neutropenia (<500 neutrophils/μL).

The acquired video images were analyzed at the two different time points shown in FIG. 36 in 10 ASCT patients undergoing chemotherapy: pre-chemotherapy (>1,500 neutrophils per μL; baseline) and during severe neutropenia (<500 neutrophils per 4). The same sets of capillaries were acquired at baseline and during severe neutropenia for every patient to minimize the amount of potential confounding factors as well as selection bias (see more details below). Acquiring one-minute videos can overcome the shot noise associated with the discrete nature of the events.

In these videos, the consistency with which events were identified in the capillary microcirculation by the three raters depended on whether capillary videos were acquired at baseline or during severe neutropenia. In instances where raters identified and counted events in capillary videos acquired during baseline, 67% of those events were validated (i.e., two or more raters identified the same event). In instances of capillary videos acquired during severe neutropenia, only 22% of events were validated. The visual features of rated events tended to be more consistent in baseline cases (see FIGS. 48A and 48B below)

These results suggested that events with consistently detectable visual features correlate with the presence of WBC and neutrophils. The validated-event counts were therefore treated as proxies to WBC counts. The fact that most validated events happened in capillary sections comparable to the size of a WBC (see FIG. 47) also corroborates findings from previous literature, which relate observed gaps to combinations of WBCs and plasma flowing through the capillary.

Non-invasive Detection of Severe Neutropenia

White-blood-cell (WBC) count can be used as one indicator of immunological status in the diagnosis and treatment of multiple medical conditions, including cancer, infectious diseases, sepsis, and autoimmune disorders. WBC count is also used in immunosuppressant drugs. However, current methods of WBC counting usually involves personal visits to healthcare centers for phlebotomy performed by trained clinical personnel, even with finger-prick technologies. This limitation restricts both frequency and time duration of the monitoring. In addition, traditional blood testing typically uses specific reagents and sterile conditions, which may preclude applicability in resource-limited environments. In contrast, a non-invasive approach to WBC measurement can circumvent many of these requirements, drawing parallels to existing non-invasive technologies for the monitoring of blood oxygen saturation levels.

One step towards non-invasive WBC analysis includes non-invasive screening for severe neutropenia, which can be defined as low levels of neutrophils (e.g., less than 500 per μL)—a common type of WBC. This condition is one of the main toxicities in patients receiving common chemotherapy regimens. It is responsible for a significant amount of morbidity and a significant risk of mortality because of its associated increased risk of infection. However, the monitoring of severe neutropenia is currently insufficient for the aforementioned reasons. This barrier to rapid clinical care interferes with the timely life-saving interventions of prophylactic antibiotics or growth colony stimulating factors in afebrile patients with prolonged severe neutropenia. In that regard, a non-invasive method can substantially impact the outpatient care and management of patients at high risk for severe neutropenia-related immunosuppression.

Systems, apparatus, and methods described herein can provide a screening tool for severe neutropenia based on non-invasive and portable optical visualization of capillaries. When capillary diameter approaches WBC diameter (e.g., about 10 μm to about 20 μm), the WBC can completely fill the capillary lumen. This typically causes a red-blood-cell (RBC) depletion downstream of the WBC in the microcirculation where WBCs flow with a lower velocity than the velocity of the RBCs. In this situation, proper illumination (e.g., at specific wavelengths) can render WBCs transparent and RBCs dark, and the passage of a WBC can appear as an optical absorption gap in the continuous RBC stream that moves through the capillary.

Using white-light trans-illumination microscopy, this "gap" phenomenon can be observed in a rabbit ear window model. The results explicitly showed RBCs accumulating upstream of WBCs with a RBC-depleted area downstream when the capillary and WBC were of comparable diameters. The same phenomenon was also observed in rat-cremaster and bat-wing microcirculation, using blue-light transillumination to maximize contrast between RBCs—peak absorption for oxy- and deoxyhemoglobin is blue at 420 nm—and low-absorption regions that lack RBCs. Observing the flow of RBCs over time revealed the capillary morphology, in which brighter regions associated with optical-absorption gaps inside the capillary lumen. Fluorescent labeling can also be used to confirm that gaps were associated with WBCs.

The idea that such absorption gaps relate to WBCs was investigated in humans by taking advantage of the blue entoptic phenomenon, where WBCs transmit blue light through as they flow in front of the retina, thus creating bright spots that the subject can see. For example, subjects can have their eyes illuminated with blue light and were asked how many bright spots they perceived. Group differences in amounts of perceived spots between baseline, leukopenic, and leukocytotic subjects—related to normal, abnormally low, and abnormally high ranges of WBC counts, respectively—were reported. One limitation of these methods, however, is their reliance on subject self-assessment. They are thus prone to individual biases and poor repeatability that do not make them amenable for clinical screening.

Overall, these findings suggest that flowing gaps in capillaries could provide a basis for a new method to measure WBC counts non-invasively. Systems, apparatus, and methods described herein use nailfold capillaries that are superficial (e.g., about 50 μm to about 100 μm deep), have diameters comparable to WBC size, and run substantially parallel to the skin surface, and can thus be visualized non-invasively with simple, affordable optical equipment.

Figure 40:
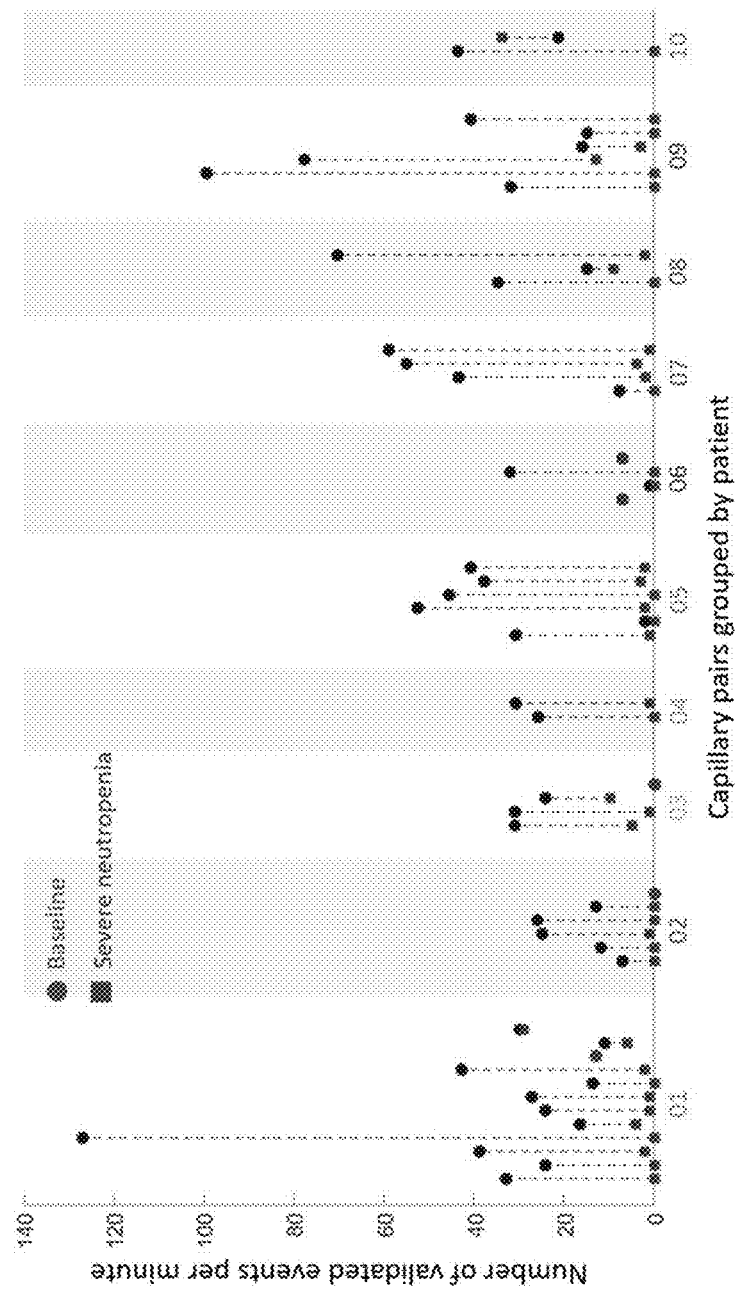
FIG. 40 shows the number of validated events per minute in all studied capillary pairs.

In this technique, optical imaging is used to screen for severe neutropenia in human subjects by counting events defined as instances of moving optical absorption gaps in the nailfold microcirculation. To do so, a portable apparatus is constructed to produce optical microscopy videos of capillaries (see, e.g., FIGS. 35A-35C). The technique can maximize RBC to non-RBC contrast over multiple capillaries within one field of view while ensuring adequate resolution, depth of focus, stability, and frame rate. Based on this apparatus, a clinical study was conducted (see, e.g., FIG. 34) involving 10 patients undergoing high-dose chemotherapy and autologous stem-cell transplantation (ASCT) given the predictability of their neutrophil nadir and recovery kinetics. For each patient, one-minute videos of the same capillary set were acquired with the apparatus at two time points: pre-chemotherapy baseline (about 1,500 neutrophils per μL) and severe neutropenia (about 500 neutrophils per μL) (see, e.g., FIGS. 29A and 29B). Based on these data, a method can be developed and validated to tag event counts (see, FIGS. 38A-39D) and to discriminate between baseline and severe neutropenia across all patients (see, e.g., FIGS. 40 and 41). The Baseline State can be Classified from the Severe-Neutropenic State Non-Invasively FIG. 40 shows the number of validated events per minute in all studied capillary pairs. Values at baseline (blue dots) showed a statistically significant difference when compared to their corresponding values at severe neutropenia (red squares). Only validated events are considered in order to maximize the objectivity of the event selection and discard noise. All capillaries were analyzed both at baseline and severe neutropenia (98 pairs in total; black dotted lines).

The number of validated-event counts in a capillary imaged during severe neutropenia was consistently less than the counts in the same capillary imaged during baseline as seen in FIG. 40. Specifically, the paired capillary counts showed a highly statistically significant difference ($P<10^{-8}$; Wilcoxon signed-rank test) between baseline and severe neutropenia. Counts from distinct capillaries tended to vary across the same patient, sometimes reaching low values even at baseline. Such variations may be associated with several factors, which motivated the aggregation of counts from several capillaries for every patient (see more details below).

Figure 41:
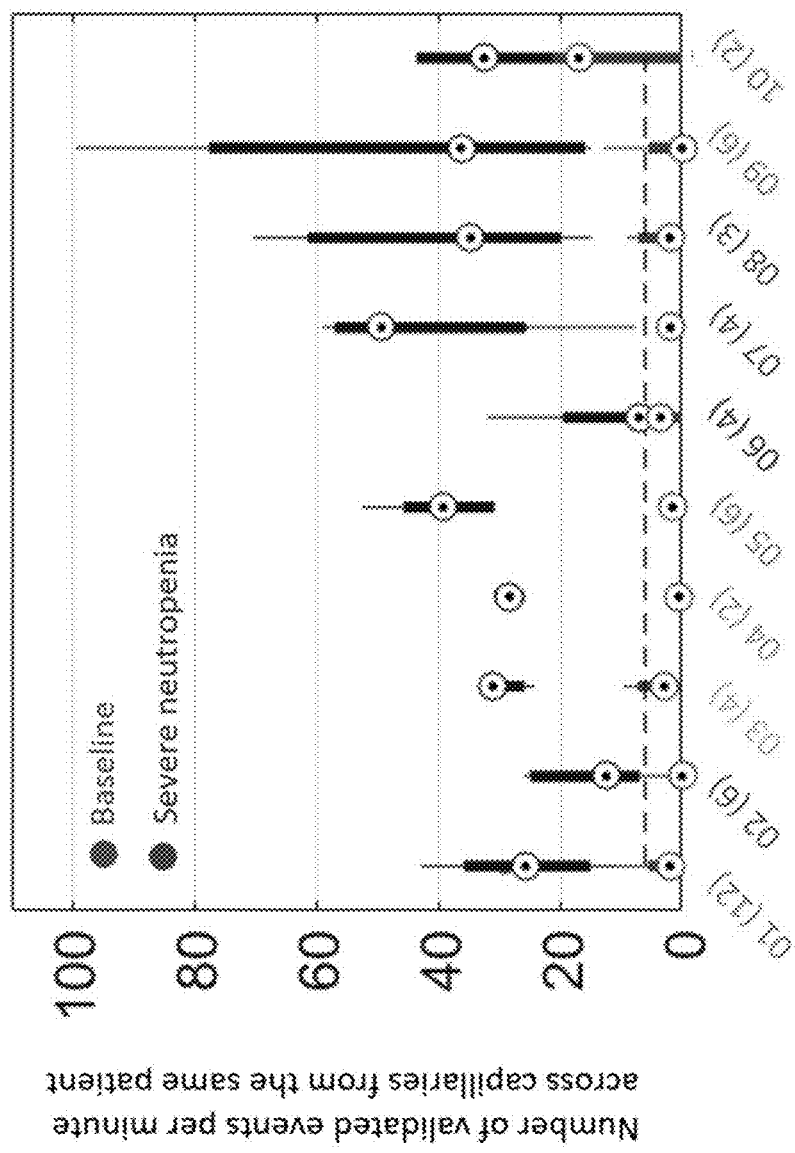
FIG. 41 shows the discrimination between baseline and severe neutropenia observed in the clinical study.

FIG. 41 shows the discrimination between baseline and severe neutropenia. The median number of validated events observed per minute, when aggregating all available capillaries per patient, allows discriminating between baseline (blue dots) and severe neutropenia (red dots) for the 20 acquired videos and 10 patients of the study. The corresponding cross-capillary variability is also shown for each patient (blue and red bars). The optimal threshold to separate baseline from severe neutropenia is seven events per capillary minute (dotted black line). The X-axis is labeled with the patient IDs together with their amount of analyzed capillaries (brackets). The median amount of capillaries used per patient was four.

The distinction between the neutropenic and baseline states is also apparent when aggregating the data across all the capillaries from a given patient at a given time (FIG. 41); the results showed a statistically significant difference ($P=0.002$; Wilcoxon signed-rank test) between baseline and severe neutropenia. Furthermore, in this capillary-aggregated case, the distribution of validated-event counts at baseline does not overlap the distribution when severely neutropenic. Indeed, at a threshold of 7 counts, the median count for capillaries in a given patient could correctly classify 9 of 10 neutropenic cases. The two or three first added capillaries accounted for most gain in classification performance (see FIGS. 44A and 44B).

The above study demonstrated that severe neutropenia can be detected non-invasively in humans based on optical imaging. It also validates the overall classification strategy as a proof of principle involving the optical apparatus, experimental protocol, and data-analysis techniques.

By design, the clinical study involved baseline absolute neutrophil counts (ANCs) (>1,500 neutrophils/μL) and severe neutropenia (<500 neutrophils/μL) in the same patients. While the classification approach was not assessed in the mild (grade II, <1,500 neutrophils/μL) and moderate (grade III, <1,000 neutrophils/μL) neutropenia cases, the current results can be extrapolated to these additional ranges assuming that average event counts vary accordingly. This may involve additional clinical studies with more representative data throughout the different grades of neutropenia. Meanwhile, the event counts obtained for each patient in the study (shown in FIG. 41) are consistent with the corresponding reference cell concentrations shown in Table 1 below.

TABLE 1

Reference values obtained from hospital clinical laboratory.

| Patient | Leukocytes (cells/ul) | | Neutrophils (cells/ul) | |
|---|---|---|---|---|
| ID | Baseline | Severe N. | Baseline | Severe N. |
| 01 | 5500 | 100 | 4060 | 10 |
| 02 | 2000 | 300 | 1280 | 10 |
| 03 | 5860 | 210 | 5660 | 0 |
| 04 | 4290 | 40 | 2830 | 20 |
| 05 | 2530 | 20 | 1950 | 10 |
| 06 | 2930 | 100 | 1840 | 30 |
| 07 | 7430 | 90 | 7100 | 0 |
| 08 | 6370 | 50 | 6040 | 0 |
| 09 | 3180 | 40 | 2770 | 10 |
| 10 | 5350 | 120 | 3700 | 0 |

Specifically, assuming an average blood-flow speed of 800 μm/s and an average capillary diameter of 15 μm, the median values of the aggregated patient counts for baseline and severe neutropenia, i.e., 31.73 and 1.96, yield WBC-concentration estimates of about 3,700 and 200 cells/μL. Both estimates fall within the ranges of the corresponding references from the gold standard laboratory assays (Table 1).

The event rating can be performed automatically on the input capillary videos. Such an algorithm can follow approaches used for detecting objects moving through capillaries or more advanced strategies, such as machine learning techniques. Several event features, such as contrast, size, or persistence, can be employed. Besides the mere counts, the algorithmic estimation of capillary blood flow may improve the precision and accuracy of the results by providing estimates that are physically consistent with WBC concentrations.

Further improvements on the apparatus can increase the amounts of capillaries per patient that satisfy the quality and consistency criteria required for further analysis. This can be useful for a future translation of this technology to clinical practice. The constraint of following the same capillaries for the same patients may be relaxed to ease the clinical applicability of the method.

One extension to this study can be to investigate whether specific WBC ranges can be identified beyond screening for severe neutropenia. This can broaden the applicability of the technique described herein not only within the context of chemotherapy, but also to new settings, such as infectious diseases, while still following a similar conceptual approach. Non-invasive differential WBC counts may also be achieved based on similar techniques/data, knowing that distinct WBC types lead to distinct optical properties and image features, e.g., non-granular and granular WBC correspond to distinct event lengths and backscattering properties in a capillary.

Overall, this study proved that chemotherapy-induced severe neutropenia can be detected non-invasively through the fingernail with an ad-hoc developed prototype. This study represents the first proof of concept for a technology that could measure an important toxicity of chemotherapy by optical means. The automatization, replication, and refinement of these results may lead to a new paradigm in the monitoring of cancer patients at risk of severe neutropenia. Furthermore, from a more general standpoint, the proposed imaging technique and conceptual approach could constitute one first step towards non-invasive, in-vivo WBC counting.

Example

A pilot diagnostic validation study was conducted to test the a-priori hypothesis that the non-invasive technique allows the classification of severe neutropenia (<500 neutrophils/μL) versus the baseline status (>1,500 neutrophils/μL) in patients. A cohort of patients who were undergoing high-dose chemotherapy followed by ASCT was enrolled. The kinetics of neutrophil counts in these patients is predictable because the intensity of the chemotherapy applied prior to transplantation ensures the passage through a severe-neutropenia stage followed by recovery. In the framework of this study, no power analysis was carried out and a convenience sample of 10 subjects (as selected from the initial patient pool) was considered sufficient to test the study hypothesis. Non-parametric tests were used as well as ROC curve analyses. All human raters who analyzed the data were blinded, as detailed below.

In total, 23 patients were recruited, with 16 and 7 patients from the Massachusetts General Hospital, Boston, Mass., USA, and Hospital Universitario La Paz, Madrid, Spain, respectively. Each recruited patient signed an informed consent. All the information obtained was anonymous and the participants were not identifiable.

The patient inclusion criteria used for recruitment were the following: (a) patients must have a scheduled ASCT of hematopoietic progenitors; (b) patients must be 18 years or older; (c) patients must have the ability to understand and the willingness to sign a written consent document; (d) at baseline, patients must have a leukocyte count equal to or greater than 3,000 cells/uL and a neutrophil count equal to or greater than 1,500 cells/uL. Patients were excluded if suffering from myelodysplasia or from a history of allergic reactions to components of chemical compositions similar to the oil used for optical coupling in the clinical device, or if their skin photoype was larger than four in the Fitzpatrick scale.

The MGH clinical study was approved by the Dana-Farber/Harvard Cancer Center (DFHCC) institutional review board, and by the MIT Committee on the Use of Humans as Experimental Subjects (COUHES) as COUHES Protocol #1610717680. This study was also registered at Clinicaltrials.gov. The La Paz clinical study was approved by the La Paz Ethics Committee in the document HULP PI-2353. The analysis of anonymized data from these pilot studies was also approved by the Ethics Committee of Universidad Politécnica de Madrid.

Optical Apparatus

One example configuration of the apparatus (shown in FIG. 35A) used for video acquisition in ASCT patients includes the following elements. This configuration is for illustrative purposes only and variations may be made by one of ordinary skill in the art.

1. Imaging objective. Edmund Optics TECHSPEC 5×. The optical features of this objective are a 5× magnification and a maximum numerical aperture of 0.15 reduced through the use of a 3D-printed iris of 2.5 mm diameter, which maximizes the depth of focus and imaging multiple capillaries simultaneously. The working distance is 16.2 mm, and the maximum field of view (FOV) 1.8×1.32 mm. Its dimensions correspond to a 50 mm fixed tube length and a 93.81 mm total length. Its height, azimuth, and focal position are manually adjustable.

2. CMOS camera. Thorlabs DCC3240N. This CMOS camera is mounted to the objective and computer-powered through a USB connection. It comprises a global/rolling shutter. Its field of view (FOV) is 1280×1024 pixels, or 1360×1088 um at 5× magnification, corresponding to a pixel size of 1.0625×1.0625 um. Its frame rate is about 60 frames per second (FPS) in full frame, thus ensuring enough temporal resolution to detect and track events given that the range of blood flow speeds in nailfold capillaries is 100-1,000 μm/s. The frame rate can reach 229 FPS if restricted a FOV of 320×240 pixels. Its bit depth is 10 bits per pixel monochrome.

3. Illuminators. Rapid prototyped LED holders, cage-mounted with heat sinks at angles of about 70 degrees from the detection axis were used. They include high-power Luxeon LEDs emitting light in deep blue, i.e., at 420 nm. This illumination wavelength allows to maximize the contrast between RBCs—which appear dark in the videos—and optical-absorption gaps. Each LED emits 161 Lumens at 700 mA, using an aspheric collection lens with F=20.1 mm, NA=0.6 and an adjustable collimation slit Thorlabs VA100C.

4. Power driver. Used to drive both LED illuminators continuously at constant DC power level.

5. Disposable hand rest. A 3D-printed and rigidly mounted platform used to hold the finger in a stable position for at least one-minute imaging. This platform comprises a one-size-fits-all finger well. Optical-coupling oil (Johnson & Johnson, refractive index=1.51) remains in the finger well.

6. Laptop and software. A laptop connected to the CMOS camera was used for power and image acquisition. Specifically tailored LabView software was used for the acquisition and storage of the videos. The output data collected for every patient and acquisition session with this software consist of a set of uncompressed videos, and for each of the videos, the time stamps providing information on the exact acquisition times associated with each frame.

As part of the clinical study, two units of this apparatus were mounted and employed at the Massachusetts General Hospital, Boston, Mass., USA, and at La Paz, Madrid, Spain, respectively. Following every use of the apparatus on a patient, disinfectant wipes were employed on the system components. The use of this device was approved for clinical research as the DF/HCC protocol #15-070.

Data Collection

In the study, videos were acquired from the same sets capillaries at baseline and during severe neutropenia for every given patient. Tracking the same capillaries at both time points allowed avoiding potential biases in the capillary selection, and minimizing confounding factors, e.g., this was expected to minimize changes in capillary geometry between the baseline and severe-neutropenic time points, thus ensuring that changes in count values within one given capillary pair reflects the underlying change in WBC concentration most accurately.

In order to obtain videos containing common capillaries in a given patient, the optical-prototype user located at least one capillary area similar to baseline during severe neutropenia. This process was performed manually during live data acquisition, which proved challenging in certain cases for logistical reasons. Meanwhile, the variety of capillary distributions and morphologies potentially allowed for the accurate identification of regions acquired previously in the baseline acquisition. In addition, the capillary-area-identification process was simplified by the fact that the nailfold capillaries of interest are selected near from the nail boundary; the capillary regions of interest were thus restricted accordingly.

Out of the 23 recruited patients, 10 were deemed compliant with the quality criteria and eligible for further processing (see capillary selection). Specifically, six whole-patient datasets were excluded due to insufficient imaging quality, and four were excluded due to lack of correspondence between the capillaries studied in baseline and severe-neutropenic time points. For each of the 10 eligible patients, at least one pair of videos was selected, corresponding to the acquisitions of the same capillary area in both clinical states. This amounts to 20 raw-video datasets, with two distinct capillary regions acquired for Patients 01 and 02. In total, 49 distinct capillaries were selected to be followed and analyzed at baseline and during severe neutropenia.

Videos were acquired within eight hours of a corresponding blood test that provides reference information. Specifically, in addition to the selected videos and capillaries, the WBC and ANC concentrations from the state-of-the-art blood-cell analytics were obtained for every patient together with their clinical state (see Table 1). The reference blood-analytics values from this table reveal the decrease in WBC and ANC concentrations between baseline and severe neutropenia.

Pre-Processing Workflow

Figure 42:
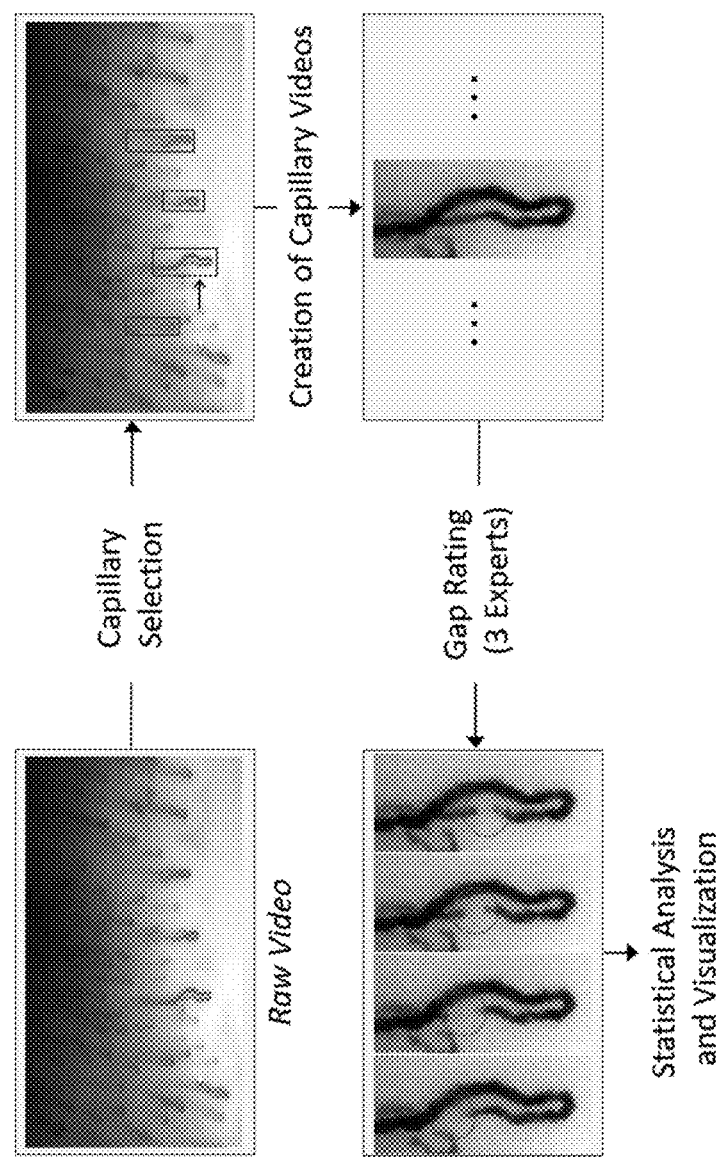
FIG. 42 illustrates a pre-processing workflow in the clinical study to process images acquired by the apparatus shown in FIG. 35A.
Figure 43:
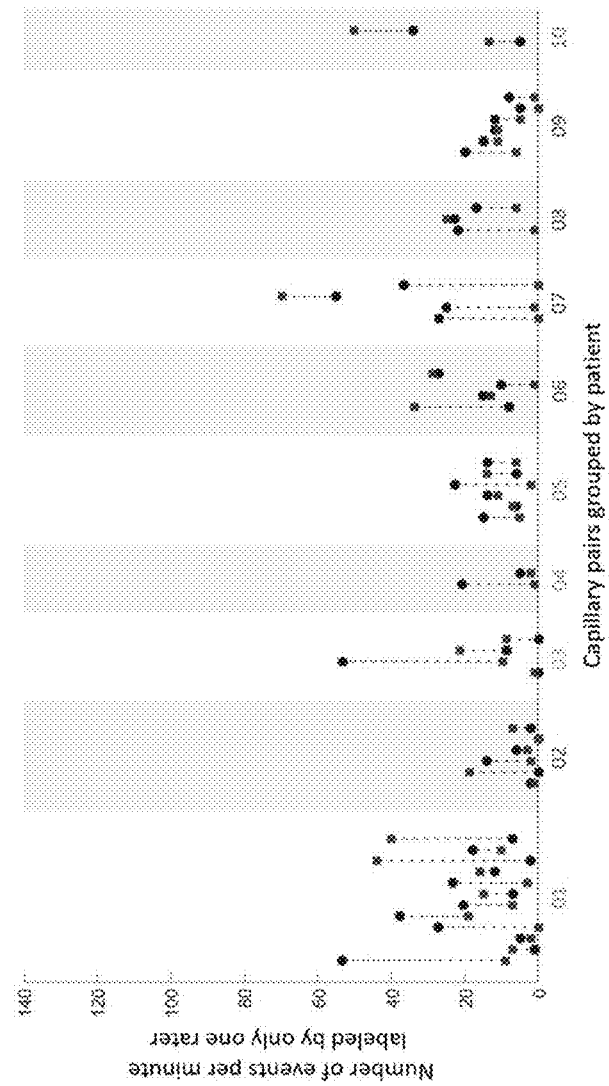
FIG. 43 shows the number of events labeled by one single rater in the clinical study.

FIG. 42 illustrates a pre-processing workflow in the clinical study. Given a raw video acquisition of a patient (top left), the set of capillaries of suitable quality is selected by two human experts (top right; green rectangles). For each selected capillary (top right; example identified by arrow), a motion-corrected video of the corresponding region of interest is then created (bottom right). The following step (bottom left) includes event labeling by three blinded human raters, which allows for subsequent analysis and event counting, aggregation, and visualization.

Each raw input video of interest was processed according to the pre-processing workflow shown in FIG. 42. Following capillary selection, each of the capillary videos included in the study was cropped to the corresponding region of interest and registered with respect to a reference frame in the sequence to correct for motion during acquisition. The motion-corrected videos were anonymized/shuffled and then used by blind experts to identify events, deriving event counts accordingly. The data with labeled events could then be visualized a posteriori. Details on these steps are provided below.

Capillary Selection

Given the raw videos acquired from one given patient, two human experts separately defined sets of suitable capillaries based on qualitative empirical a-priori criteria defined below. In order to avoid potential biases, only capillaries selected by both blinded raters were included in the study. Each expert individually selected the best capillaries in raw videos according to the following criteria:

A. Illumination. Capillaries are visible with sufficient contrast to an observer.

B. Focus. Detailed capillary structures/dynamics are visible and not blurred out.

C. Flow. Blood flow exists to allow for potential events to be identified and counted.

D. Stability. Capillaries fully remain within the field of view of the video in all frames.

E. Visibility. No object (e.g., air bubbles) can occlude capillaries.

F. Morphology. Capillaries exhibit clear arterial and venous limbs.

G. Fulfillment of conditions A-F both in baseline and severe-neutropenia acquisitions.

For every patient, each expert first followed this procedure for the baseline-state videos. The goal was to acquire paired capillary videos for every patient, the set of candidate capillaries in severe neutropenia being limited by the choices already made during baseline. Resulting capillary-video pairs—at least one per patient—are the ones complying with the above criteria in both baseline and severe neutropenia and according to both experts (see FIGS. 49-60).

Creation of Capillary Videos

Based on the raw video data and on the above capillary-selection procedure, individual capillary videos were created based on (a) the definition, on the first video frame, of rectangular regions of interest enclosing each of the capillaries of interest, followed by (b) video motion-compensation software, which locally compensates camera movements and ensures that the position of every capillary remains stable within the corresponding region of interest for the whole duration of the video. Note that all raw videos were first flattened, i.e., their local brightness was normalized through Gaussian filtering to remove potential effects of non-uniform illumination.

Step (a) was carried out based on a simple graphical user interface, and step (b) was performed based on a specifically tailored motion-compensation algorithm. Both implementations were done in MATLAB. Based on the raw video and on a given rectangular region of interest, the algorithm outputs a motion-corrected capillary video applying a rigid registration technique; specifically, it aligns all video frames with the first one assuming that potential camera movements in the region of interest are mere combinations of X and Y translations, excluding rotations.

While frame movements in the raw video can involve deformations, visual inspection of the registration results proved successful when applied to every capillary field of view separately. As a similarity metric and optimization criterion, the algorithm uses mutual information, which is a measure based on information theory that copes with slight contrast changes and guarantees accurate sub-pixel alignment. Prior to this registration process, a preliminary coarse-registration step is performed to ensure a suitable initialization. This initialization step performs frame pre-alignment based on cross-correlation analysis of pixel values and spatial gradients.

Event Rating

Based on a graphical user interface, three human raters followed specific visual criteria to identify all events in the capillary videos. Under this visual criteria, the consequence of the passage of a WBC through a capillary of approximately the same diameter includes creating a region depleted of RBCs. Specifically, moving optical-absorption gaps referred to as events having the following properties.

In one example, the events are noticeably brighter than the surrounding capillary flow. In another example, the events can be identified as clear objects moving along the capillary flow. In yet another example, the events occupy the whole capillary diameter and extend along the flow direction.

Raters were blinded with respect to the others and to the corresponding blood-analytics, physiological state, patient, and temporal information. Each rater labeled the corresponding frames and spatial locations inside the capillary where these events happened.

The indexing of the videos made available to the raters for event identification and counting was obtained by randomly shuffling the original-video names, thus rendering access to the original indexing impossible for the raters, though the corresponding content was similar. Furthermore, the amount of frames was always the same for all videos acquired from the same patient. No side information making such identification possible was included in the corresponding files. All videos—in non-shuffled and shuffled-index versions—were anonymized in the sense that no information in the video content and naming could be used to identify patients or neutropenic state. Following blind rating, all marked events could be visualized based on a specifically developed method.

Statistical Analysis

The counts obtained from all three independent raters allowed the determination of joint rating properties, i.e., whether one single expert, or whether two or more experts agreed on the same event being observed. By convention, it is assumed that at least R raters have jointly marked a given event if the average mark times from at least R raters lie within at most ten frames ($\frac{1}{6}$ seconds) from each other, which is substantially smaller than expected event rates in capillary videos (see FIG. 46 below). Exact spatial overlay of the labels is not required. A specific case of interest is majority rater agreement, for which R is equal or greater than 2 in this setting, which yields validated events. Counts were then performed accordingly, i.e., summing events from every capillary video accordingly.

Validated counts from several capillaries were combined for each patient (see FIG. 41 and FIGS. 44A and 44B below) because the precision of individual count values in single capillaries (a) is limited by shot noise, which is proportional to the square root of the amount of counts, (b) is limited by potential WBC phenomena not complying with the event criteria and occurring in some capillaries, such as margination, (c) is dependent on the particular capillary geometry and flow rate, and (d) is dependent on the particular positioning of the capillary on the underlying capillary-network dynamics. When considering count combinations of fixed amounts of capillaries per patient (FIGS. 44A and 44B), the corresponding sets of capillaries were picked randomly and results were computed based on 10,000 trials. This is akin to Monte-Carlo integration, and allowed to effectively handle the exponentially increasing amounts of cross-patient combinations that are otherwise intractable.

When comparing the counts between capillaries or combined sets thereof, the analysis tools that was used was the Wilcoxon signed-rank test on the paired data, which avoids the statistical assumption that counts are normally distributed while testing/refuting the hypothesis Ho that there is no difference between counts obtained in baseline and severe neutropenia for the same capillaries. In addition, the study generated receiver operating characteristic (ROC) curves and corresponding area-under-curve (AUC) values, which tests the performance of binary-class classification between baseline and severe neutropenia as a function of a varying threshold count.

Visualization of Marked Events

In order to visualize marked events in capillaries, a method was developed to simultaneously visualize the frames of the capillary video of interest and the corresponding ST intensity profile of the capillary, both for the whole video duration and around a given frame. This allowed events to be visualized both explicitly as a moving object through the corresponding video frames and as a fixed profile in their ST map representation. In the context of the clinical study, this visualization technique allowed retrospective analysis of the distribution of labeled events in the videos as well as the relevance of majority rater agreement.

The concept of a ST map for capillary-flow visualization was described above. It is motivated by the fact that events can be conveniently observed in that representation: events associated with WBCs are expected to appear as thick, high-contrast, sparse, and unidirectional trajectories. These properties also relate to the visual criteria that were defined for the raters, e.g., event brightness. ST maps make the rater-marked events appear as well-defined salient trajectories surrounded by a darker background (see FIG. 39E above).

To create the ST maps, the method extracts capillary brightness—as averaged over the cross-section as a function of time and as a function of the cumulative capillary length, based on segmented capillary boundaries. In order to improve the visualization of event trajectories, the map values were normalized by subtracting their local temporal averages as obtained between 50 frames before and after every time point. The initial capillary-segmentation procedure was performed based on an image extracted from the corresponding registered video.

Since the capillary profile may be incomplete in a single video frame due to the presence of absorption gaps in the flow, a temporally integrated image was extracted for nailfold capillaries, where temporally variable features associated with the capillary flow are also enhanced to maximize contrast between the capillary and its surroundings. This approach also relates to the concept of motion-contrast enhancement. Specifically, the image that were used for segmentation was obtained through the integration of temporal-frequency components whose periods were empirically chosen to lie in the [0.25, 1.5]-second interval.

Capillary boundaries were first segmented manually in a first step, and then refined with the help of an active-contour technique. The segmentation of both capillary boundaries was then automatically resampled so as to include 1,000 points each, and such that the center of every point pair at the same index of both boundaries lies on the medial axis of the capillary, where the medial axis is the loci of all circles inscribed in the capillary. Finally, based on this segmentation, separations between the arterial limb, venous limb, and loop of the capillary were defined on a case-to-case basis for visualization (see FIGS. 45A-45C).

Acquisition Time Under Shot Noise

The video-acquisition time t was set to one minute because it remains suitable for clinical settings while being long enough to allow sampling significantly higher amounts of events N in baseline cases compared to severe-neutropenia cases. Even under the shot noise that originates from the quantized nature of events, the count distributions associated with both cases are expected to be disjoint within at least one standard deviation of their means $N_b$ and $N_n$, respectively, as expected from the calculations detailed below.

To determine this result, a worst-case scenario was considered using a lower-limit case for baseline ($C_b$=1,500 neutrophils/μL) and a higher-limit case for severe neutropenia ($C_n$=500 neutrophils/μL), which is most difficult to discriminate since the difference between cell concentrations C from both categories is minimized. Typical values from the literature were then assumed for capillary diameter (D=15 μm) and flow speed (v=800 μm/s), which allowed estimating expected amounts of events from concentrations. Specifically, $N=\pi \cdot (D/2)^2 \cdot C \cdot v \cdot t$, which yields $N_b$=4.24 and $N_n$=12.72. Finally, the shot-noise statistics imply that counts vary around these means with standard deviations $N_b^{1/2}$=2.06 and $N_n^{1/2}$=3.57, respectively. Potentially, this results in count ranges allowing for clear discrimination (see FIG. 46).

FIG. 35 shows the number of events labeled by one single rater. Baseline counts not reaching agreement between two or more experts (blue dots), as obtained in the 98 capillaries of the study, do not display any statistically significant difference (P=0.12; Wilcoxon signed rank) with respect to the corresponding counts in severe neutropenia (red squares). This result indicates that events labeled by single raters are less objective and contain less information than those with multiple-rater agreement. Capillary pairs are grouped by patient ID.

Figure 44B:
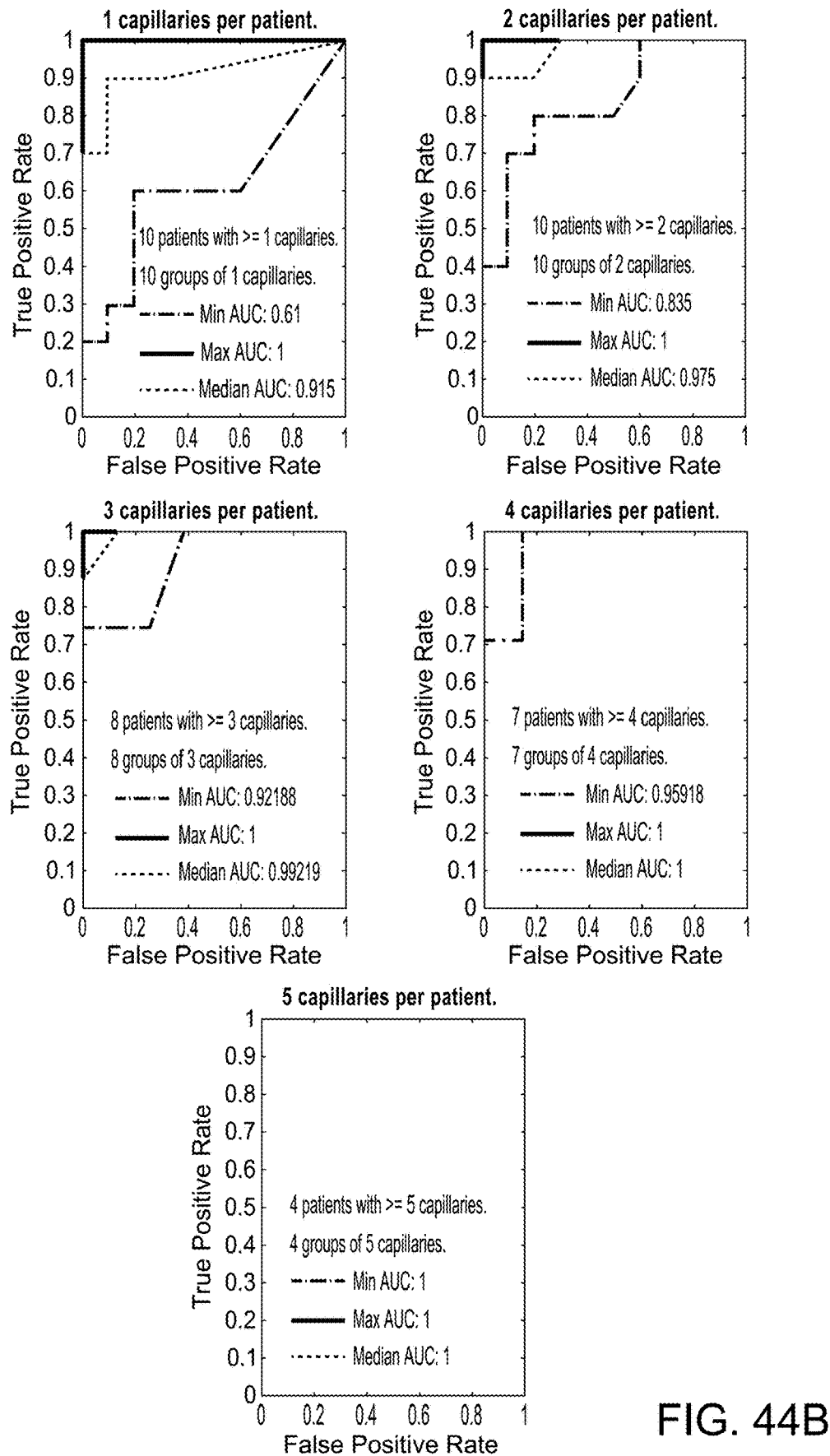

FIGS. 44A and 44B show the discrimination between baseline and severe neutropenia using capillary aggregates. FIG. 44A shows the number of event counts resulting from integrating N=1, 2, 3, 4, 5 capillaries per patient. FIG. 44B shows the ROC curves for classification of baseline vs. severe neutropenia based on integrating N=1, 2, 3, 4, 5 capillaries per patient. The patient-level distributions of the resulting count values show that their discriminatory power increases with the amount of combined capillaries per patient. Specifically, the minimum area under curve (AUC) consistently increases with the amount of combined capillaries from 0.61 to 0.84, 0.92, 0.96 and 1.00 when including 1, 2, 3, 4 and 5 capillaries, respectively.

Figures 45A, 45B, 45C:
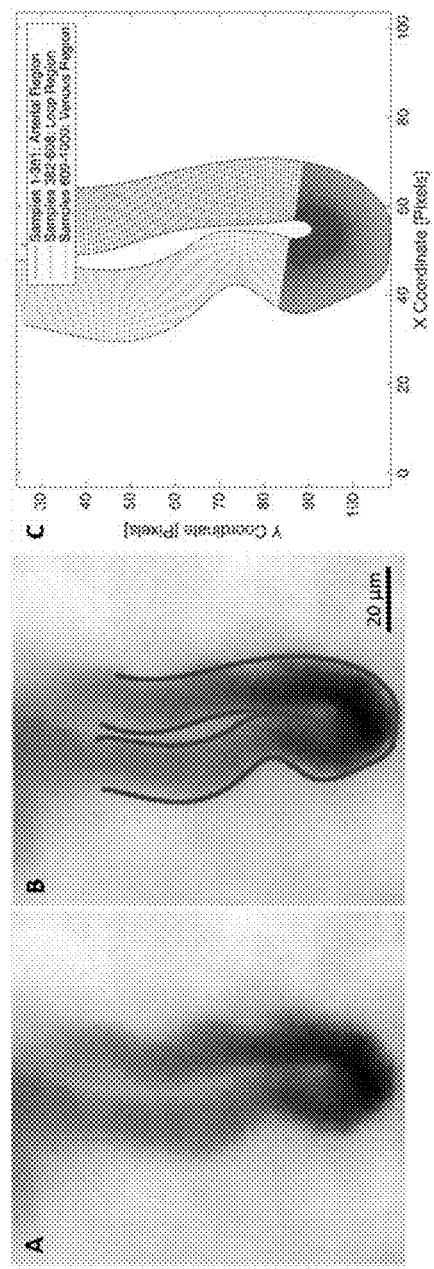
FIGS. 45A-45C show examples of a capillary segmentation.

FIGS. 45A-45C show example of a capillary segmentation. FIG. 45A shows capillary from patient 02. FIG. 45B shows the same capillary with supervised segmentation (red). The scale bar is 20 μm. FIG. 45C shows the separations between arterial limb (green), venous limb (blue), and loop (red) of the capillary can be defined on a case-to-case basis for visualization.

Figure 46:
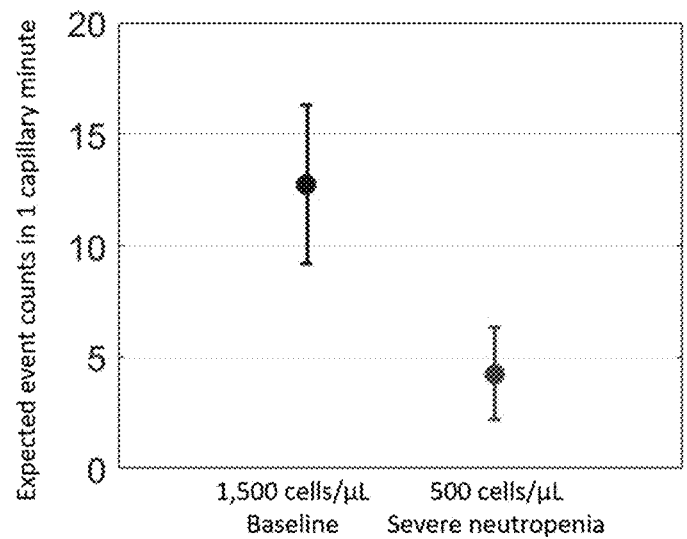
FIG. 46 shows the expected amount of events per capillary minute under shot noise.

FIG. 46 shows expected amounts of events per capillary minute under shot noise. Assuming typical capillary-diameter and speed values from the literature, amounts of expected events in baseline (blue; 1,500 neutrophils/μL) exceed the corresponding amounts in severe neutropenia (red; 500 neutrophils/μL) for a single minute of acquisition, even under shot noise. Shown are expected count averages (central dots) along with expected variations originating from shot noise up to one standard deviation (bars).

Figure 47:
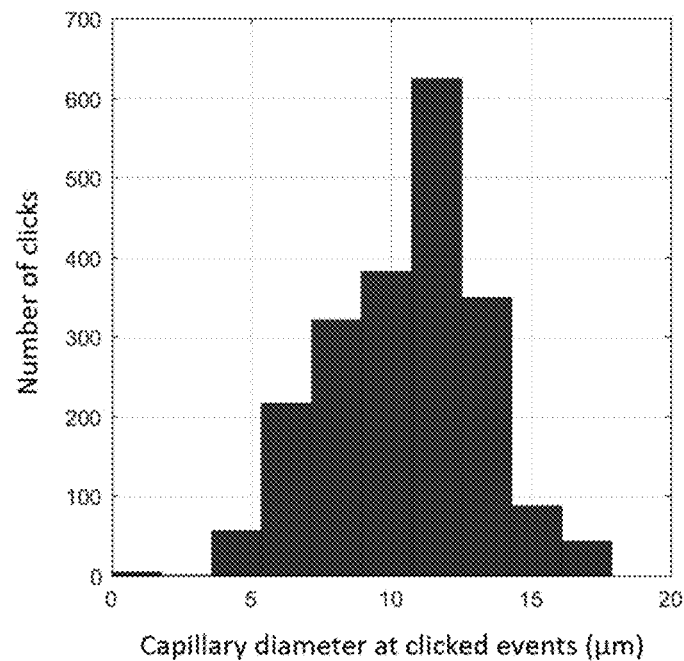
FIG. 47 shows the distribution of capillary diameters at event positions.

FIG. 47 shows the distribution of capillary diameters at events positions. The distribution of the capillary-diameter values at the positions where the three blinded raters labeled an event is shown. Detected events tend to appear in capillary segments of approximately the same size range as WBCs, i.e., [10-20] μm, thus confirming observations made in prior literature and the usability of events as proxies of WBCs.

Figures 48A, 48B:
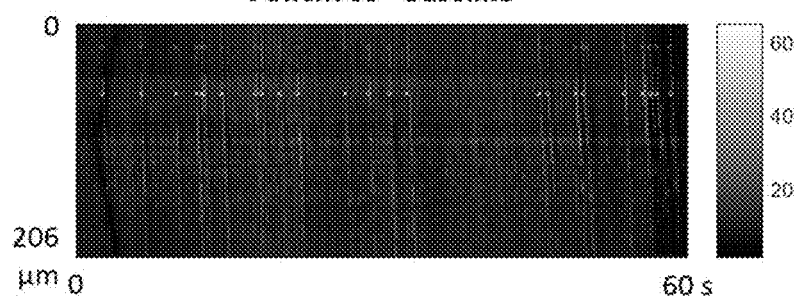
FIGS. 48A and 48B show ST maps of capillaries with high versus low ratio ratios of validated events.

FIGS. 48A and 48B show ST maps of capillaries with high versus low ratio ratios of validated events. For each event, the first click from each of the three human raters is displayed with a red, blue, and green dot, respectively. Inter-rater agreement was higher in baseline capillaries (top map) compared to the case of severe neutropenia (bottom map), indicating that events in baseline correspond to more objective physical phenomena.

Figure 49:
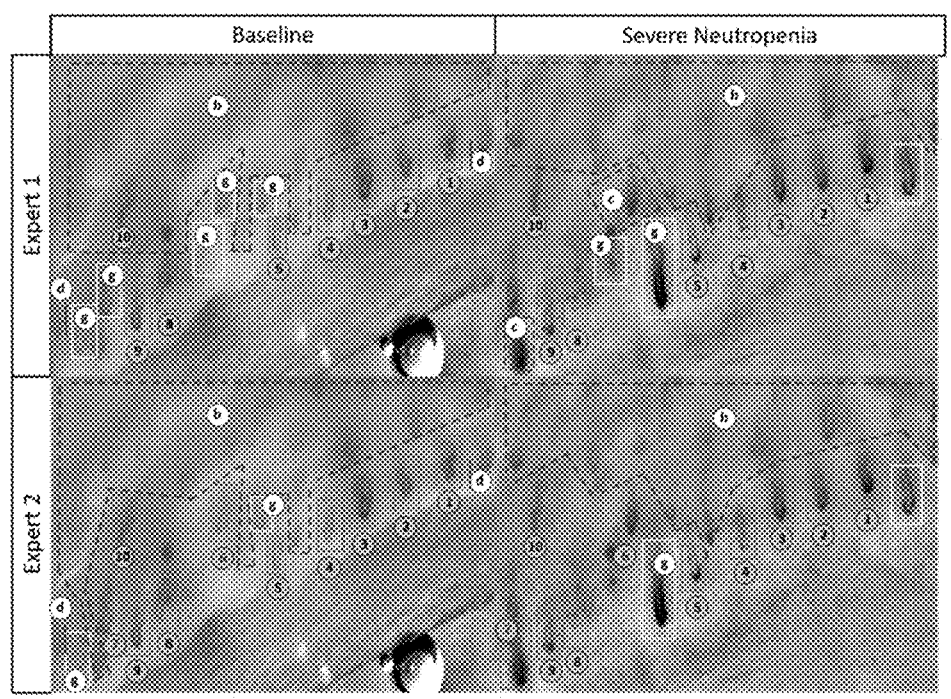
FIG. 49 shows capillary selection from both experts in raw-video pair for Patient 01, Region 1.

FIG. 49 shows capillary selection from both experts in raw-video pair from Patient 01, region 1. The videos acquired in baseline and severe-neutropenic states are displayed. The green boxes outline the selected capillary pairs which, according to each of the two experts complied with the quality criteria for both baseline and severe-neutropenia acquisitions. The red regions/capillaries are discarded due to non-compliance with the quality criteria, i.e., due in this instance to (b) lack of focus, (c) lack of blood flow, and (d) out-of-field-of-view movements. The red lines/corners in the baseline videos outline the effective field of view outside which capillaries must be discarded as they disappear during several frames due to camera movements during acquisition. The yellow boxes outline capillaries that were initially selected in baseline but were discarded later due to non-compliance in the severe-neutropenia acquisition (g). Both experts made the selection process independently and, after that, only capillaries where both experts agreed (black numbers), discarding the rest of them (red numbers).

Figure 50:
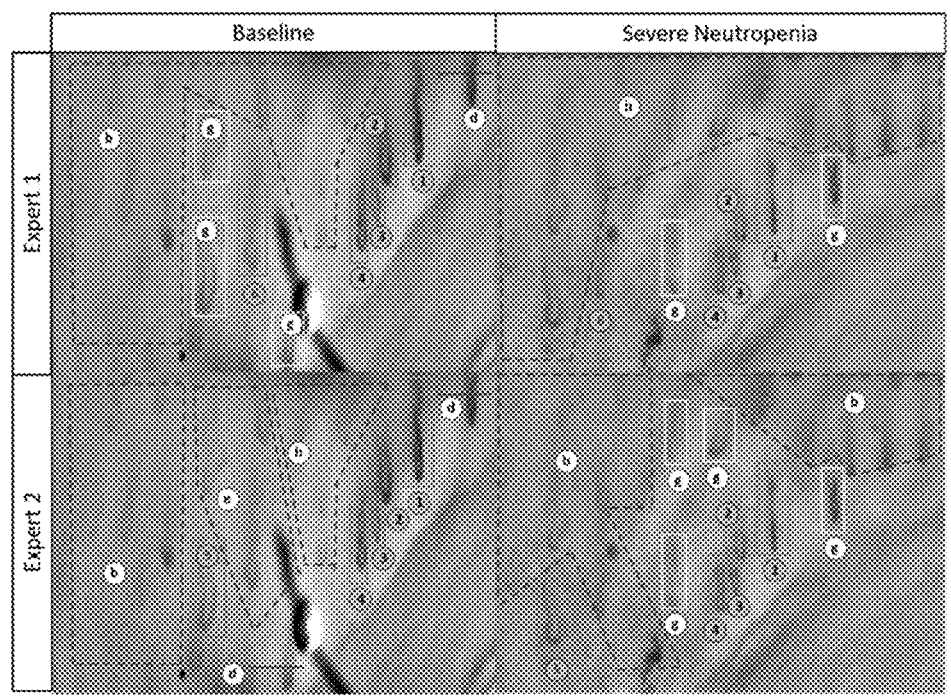
FIG. 50 shows capillary selection from both experts in raw-video pair for Patient 01, Region 2.
Figure 51:
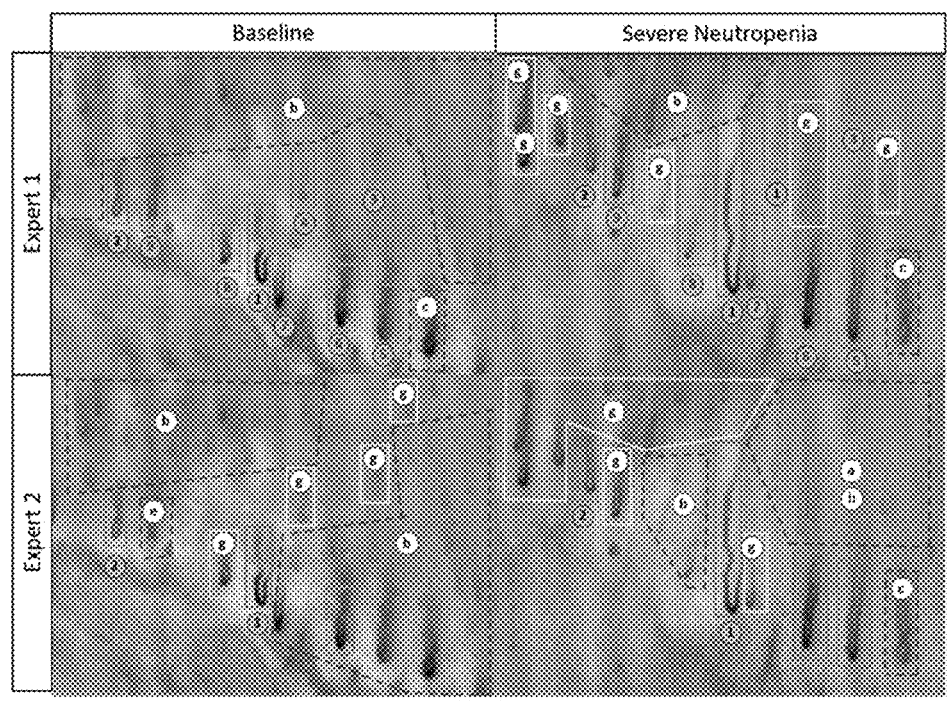
FIG. 51 shows capillary selection from both experts in raw-video pair for Patient 02, Region 1.

FIG. 50 shows capillary selection from both experts in raw-video pair from Patient 01, region 2. The videos acquired in baseline and severe-neutropenic states are displayed. The green boxes outline the selected capillary pairs which, according to each of the two experts complied with the quality criteria for both baseline and severe-neutropenia acquisitions. The red regions/capillaries are discarded due to non-compliance with the quality criteria, i.e., due in this instance to (b) lack of focus, (d) out-of-field-of-view movements, and (e) occlusions. The red lines/corners in the baseline videos outline the effective field of view outside which capillaries must be discarded as they disappear during several frames due to camera movements during acquisition. The yellow boxes outline capillaries that were initially selected in baseline but were discarded later due to non-compliance in the severe-neutropenia acquisition (g). Both experts made the selection process independently and, after that, only capillaries where both experts agreed (black numbers), discarding the rest of them (red numbers).

Figure 52:
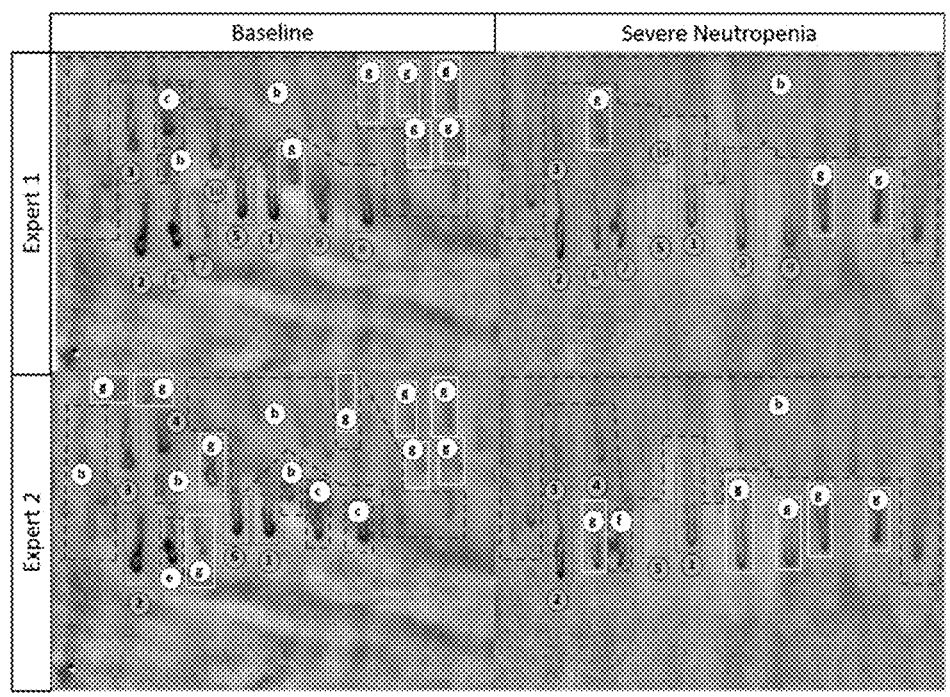
FIG. 52 shows capillary selection from both experts in raw-video pair for Patient 02, Region 2.

FIG. 52 shows capillary selection from both experts in raw-video pair from Patient 02, region 1. The videos acquired in baseline and severe-neutropenic states are displayed. The green boxes outline the selected capillary pairs which, according to each of the two experts complied with the quality criteria for both baseline and severe-neutropenia acquisitions. The red regions/capillaries are discarded due to non-compliance with the quality criteria, i.e., due in this instance to (a) poor illumination, (b) lack of focus, (c) lack of blood flow, and (e) occlusions. The red lines/corners in the baseline videos outline the effective field of view outside which capillaries must be discarded as they disappear during several frames due to camera movements during acquisition. The yellow boxes outline capillaries that were initially selected in baseline but were discarded later due to non-compliance in the severe-neutropenia acquisition (g). Both experts made the selection process independently and, after that, only capillaries where both experts agreed (black numbers), discarding the rest of them (red numbers)

FIG. 52 shows capillary selection from both experts in raw-video pair from Patient 02, region 2. The videos acquired in baseline and severe-neutropenic states are displayed. The green boxes outline the selected capillary pairs which, according to each of the two experts complied with the quality criteria for both baseline and severe-neutropenia acquisitions. The red regions/capillaries are discarded due to non-compliance with the quality criteria, i.e., due in this instance to (b) lack of focus, (c) lack of blood flow, (e) occlusions, and (f) lack of clear morphology. The red lines/corners in the baseline videos outline the effective field of view outside which capillaries must be discarded as they disappear during several frames due to camera movements during acquisition. The yellow boxes outline capillaries that were initially selected in baseline but were discarded later due to non-compliance in the severe-neutropenia acquisition (g). Both experts made the selection process independently and, after that, only capillaries where both experts agreed (black numbers), discarding the rest of them (red numbers).

Figure 53:
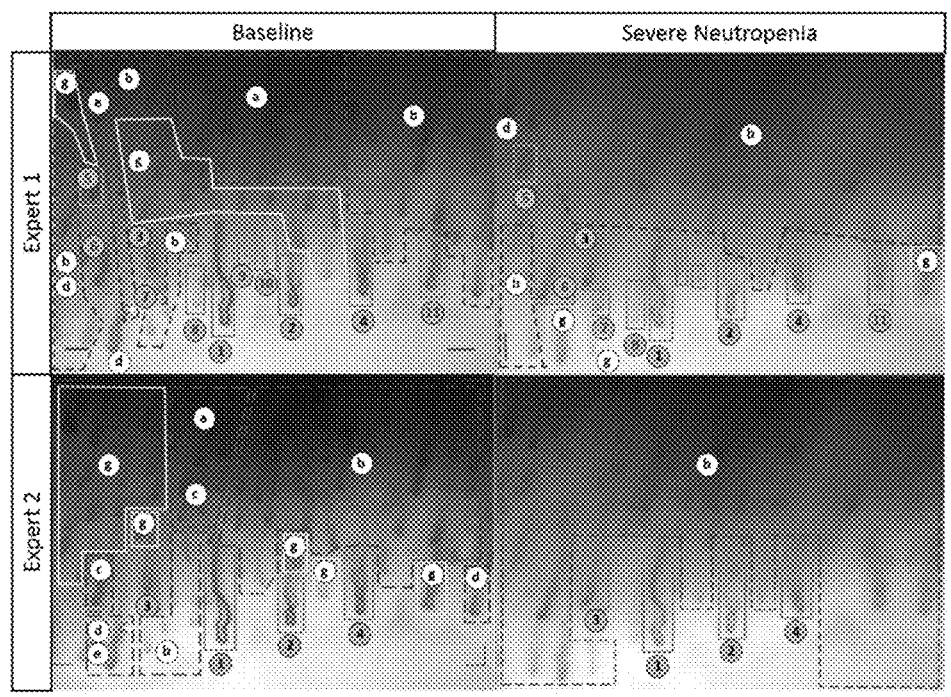
FIG. 53 shows capillary selection from both experts in raw-video pair for Patient 03.

FIG. 53 shows capillary selection from both experts in raw-video pair from Patient 03. The videos acquired in baseline and severe-neutropenic states are displayed. The green boxes outline the selected capillary pairs which, according to each of the two experts complied with the quality criteria for both baseline and severe-neutropenia acquisitions. The red regions/capillaries are discarded due to non-compliance with the quality criteria, i.e., due in this instance to (a) poor illumination, (b) lack of focus, (c) lack of blood flow, (d) out-of-field-of-view movements, and (e) occlusions. The red lines/corners in the baseline videos outline the effective field of view outside which capillaries must be discarded as they disappear during several frames due to camera movements during acquisition. The yellow boxes outline capillaries that were initially selected in baseline but were discarded later due to non-compliance in the severe-neutropenia acquisition (g). Both experts made the selection process independently and, after that, only capillaries where both experts agreed (black numbers), discarding the rest of them (red numbers).

Figure 54:
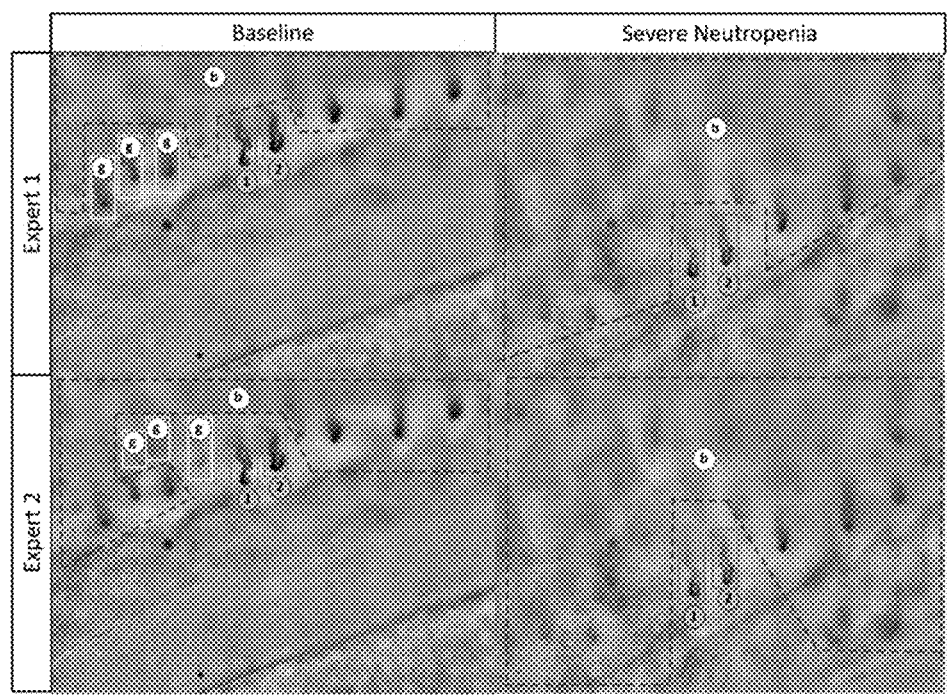
FIG. 54 shows capillary selection from both experts in raw-video pair for Patient 04.

FIG. 54 shows capillary selection from both experts in raw-video pair from Patient 04. The videos acquired in baseline and severe-neutropenic states are displayed. The green boxes outline the selected capillary pairs which, according to each of the two experts complied with the quality criteria for both baseline and severe-neutropenia acquisitions. The red regions/capillaries are discarded due to non-compliance with the quality criteria, i.e., due in this instance to (b) lack of focus. The red lines/corners in the baseline videos outline the effective field of view outside which capillaries must be discarded as they disappear during several frames due to camera movements during acquisition. The yellow boxes outline capillaries that were initially selected in baseline but were discarded later due to non-compliance in the severe-neutropenia acquisition (g). Both experts made the selection process independently and, after that, only capillaries where both experts agreed (black numbers), discarding the rest of them (red numbers).

Figure 55:
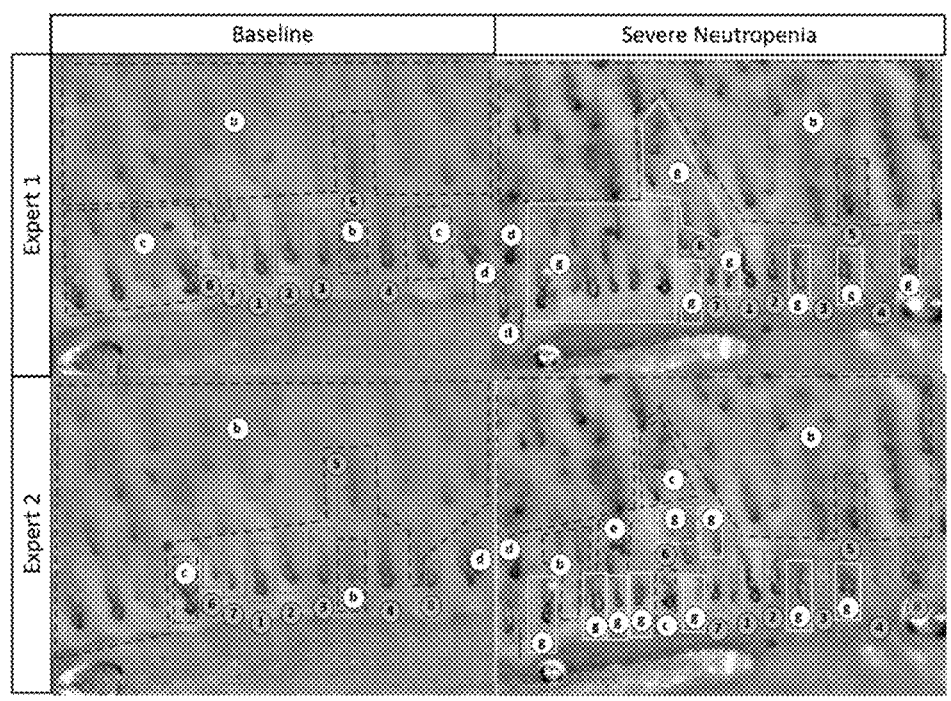
FIG. 55 shows capillary selection from both experts in raw-video pair for Patient 05.

FIG. 55 shows capillary selection from both experts in raw-video pair from Patient 05. The videos acquired in baseline and severe-neutropenic states are displayed. The green boxes outline the selected capillary pairs which, according to each of the two experts complied with the quality criteria for both baseline and severe-neutropenia acquisitions. The red regions/capillaries are discarded due to non-compliance with the quality criteria, i.e., due in this instance to (b) lack of focus, (c) lack of blood flow, (d) out-of-field-of-view movements, and (e) occlusions. The red lines/corners in the baseline videos outline the effective field of view outside which capillaries must be discarded as they disappear during several frames due to camera movements during acquisition. The yellow boxes outline capillaries that were initially selected in baseline but were discarded later due to non-compliance in the severe-neutropenia acquisition (g). Both experts made the selection process independently and, after that, only capillaries where both experts agreed (black numbers), discarding the rest of them (red numbers).

Figure 56:
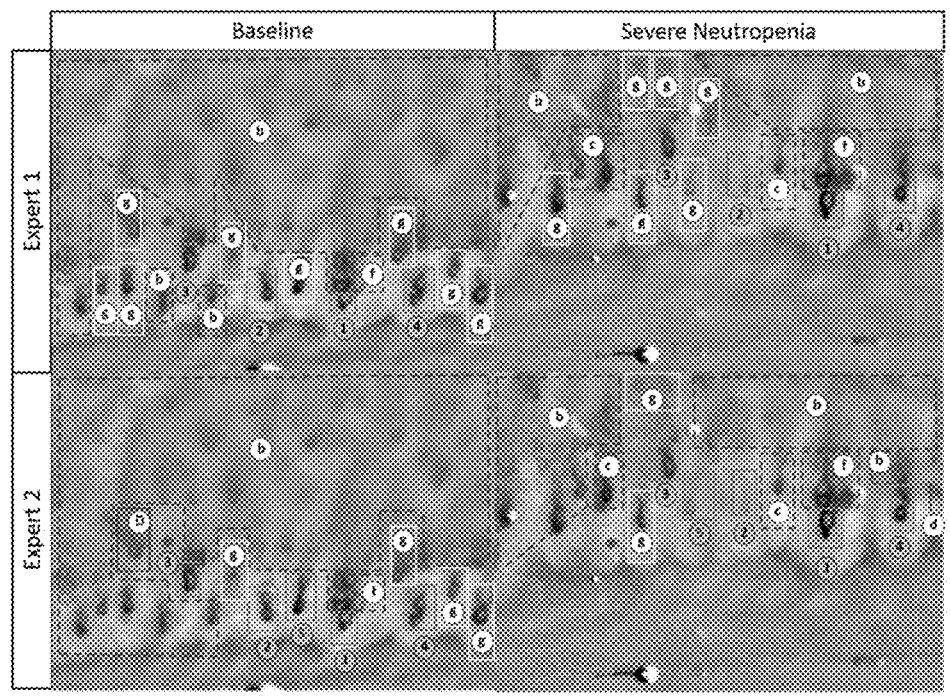
FIG. 56 shows capillary selection from both experts in raw-video pair for Patient 06.

FIG. 56 shows capillary selection from both experts in raw-video pair from Patient 06. The videos acquired in baseline and severe-neutropenic states are displayed. The green boxes outline the selected capillary pairs which, according to each of the two experts complied with the quality criteria for both baseline and severe-neutropenia acquisitions. The red regions/capillaries are discarded due to non-compliance with the quality criteria, i.e., due in this instance to (b) lack of focus, (c) lack of blood flow, (d) out-of-field-of-view movements, and (f) lack of clear morphology. The red lines/corners in the baseline videos outline the effective field of view outside which capillaries must be discarded as they disappear during several frames due to camera movements during acquisition. The yellow boxes outline capillaries that were initially selected in baseline but were discarded later due to non-compliance in the severe-neutropenia acquisition (g). Both experts made the selection process independently and, after that, only capillaries where both experts agreed (black numbers), discarding the rest of them (red numbers).

Figure 57:
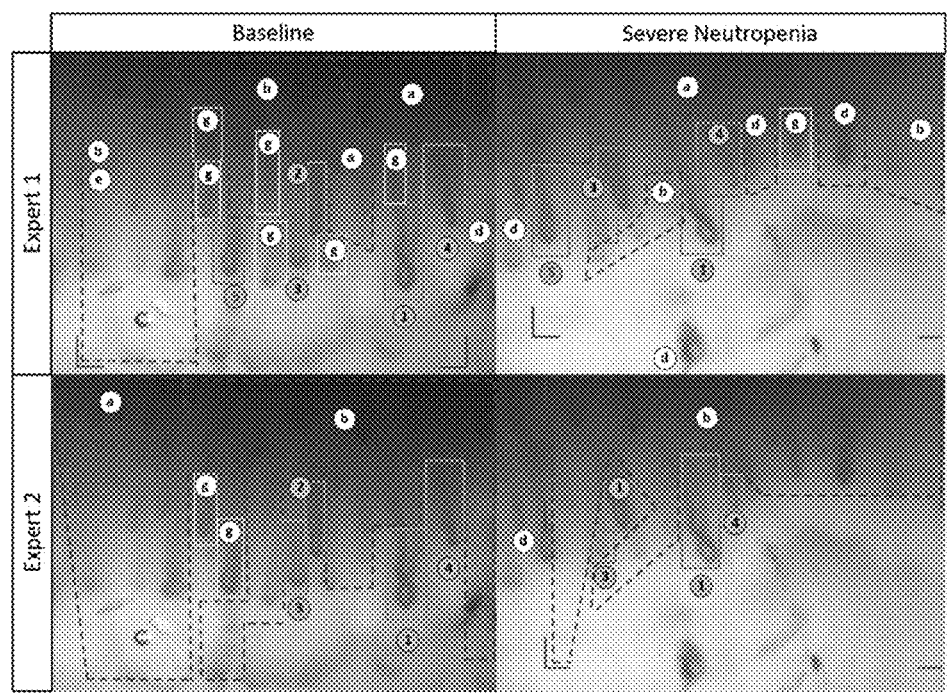
FIG. 57 shows capillary-selection from both experts in raw-video pair for Patient 07.

FIG. 57 shows capillary selection from both experts in raw-video pair from Patient 07. The videos acquired in baseline and severe-neutropenic states are displayed. The green boxes outline the selected capillary pairs which, according to each of the two experts complied with the quality criteria for both baseline and severe-neutropenia acquisitions. The red regions/capillaries are discarded due to non-compliance with the quality criteria, i.e., due in this instance to (a) poor illumination, (b) lack of focus, (d) out-of-field-of-view movements, and (e) occlusions. The red lines/corners in the baseline videos outline the effective field of view outside which capillaries must be discarded as they disappear during several frames due to camera movements during acquisition. The yellow boxes outline capillaries that were initially selected in baseline but were discarded later due to non-compliance in the severe-neutropenia acquisition (g). Both experts made the selection process independently and, after that, only capillaries where both experts agreed (black numbers), discarding the rest of them (red numbers).

Figure 58:
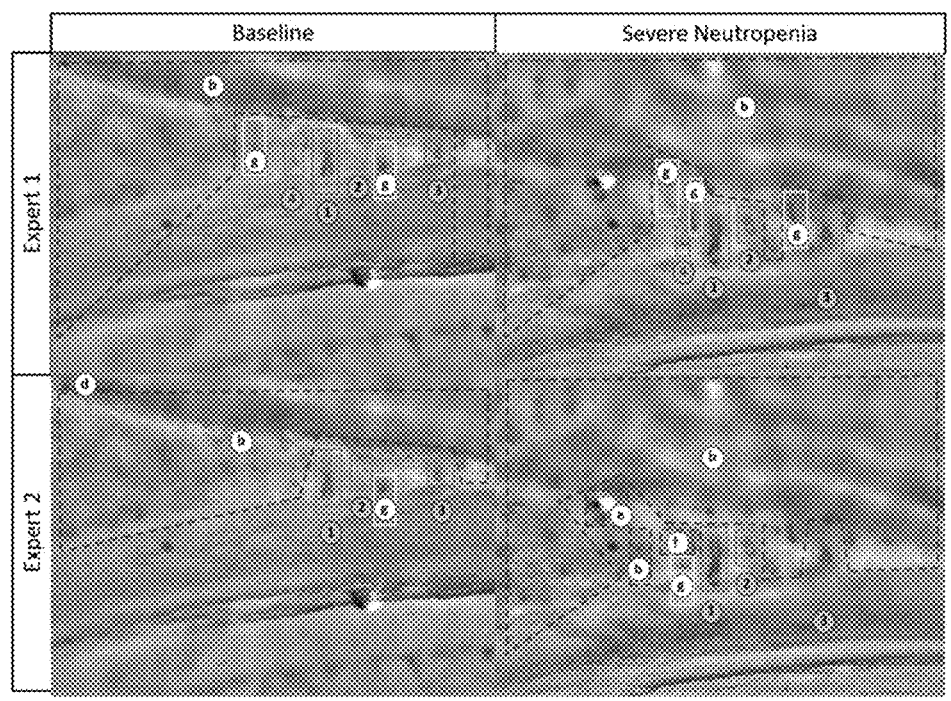
FIG. 58 shows capillary-selection from both experts in raw-video pair for Patient 08.

FIG. 58 shows capillary selection from both experts in raw-video pair from Patient 08. The videos acquired in baseline and severe-neutropenic states are displayed. The green boxes outline the selected capillary pairs which, according to each of the two experts complied with the quality criteria for both baseline and severe-neutropenia acquisitions. The red regions/capillaries are discarded due to non-compliance with the quality criteria, i.e., due in this instance to (b) lack of focus, (d) out-of-field-of-view movements, (e) occlusions, and (f) lack of clear morphology. The red lines/corners in the baseline videos outline the effective field of view outside which capillaries must be discarded as they disappear during several frames due to camera movements during acquisition. The yellow boxes outline capillaries that were initially selected in baseline but were discarded later due to non-compliance in the severe-neutropenia acquisition (g). Both experts made the selection process independently and, after that, only capillaries where both experts agreed (black numbers), discarding the rest of them (red numbers).

Figure 59:
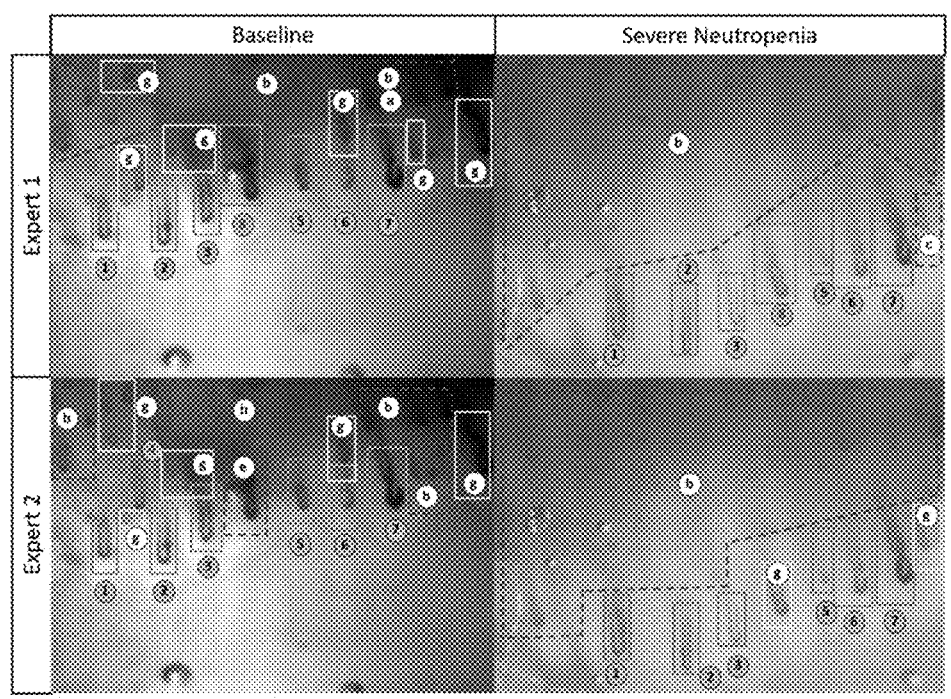
FIG. 59 shows capillary-selection from both experts in raw-video pair for Patient 09.

FIG. 59 shows capillary selection from both experts in raw-video pair from Patient 09. The videos acquired in baseline and severe-neutropenic states are displayed. The green boxes outline the selected capillary pairs which, according to each of the two experts complied with the quality criteria for both baseline and severe-neutropenia acquisitions. The red regions/capillaries are discarded due to non-compliance with the quality criteria, i.e., due in this instance to (a) poor illumination, (b) lack of focus, (c) lack of blood flow, and (e) occlusions. The red lines/corners in the baseline videos outline the effective field of view outside which capillaries must be discarded as they disappear during several frames due to camera movements during acquisition. The yellow boxes outline capillaries that were initially selected in baseline but were discarded later due to non-compliance in the severe-neutropenia acquisition (g). Both experts made the selection process independently and, after that, only capillaries where both experts agreed (black numbers), discarding the rest of them (red numbers).

Figure 60:
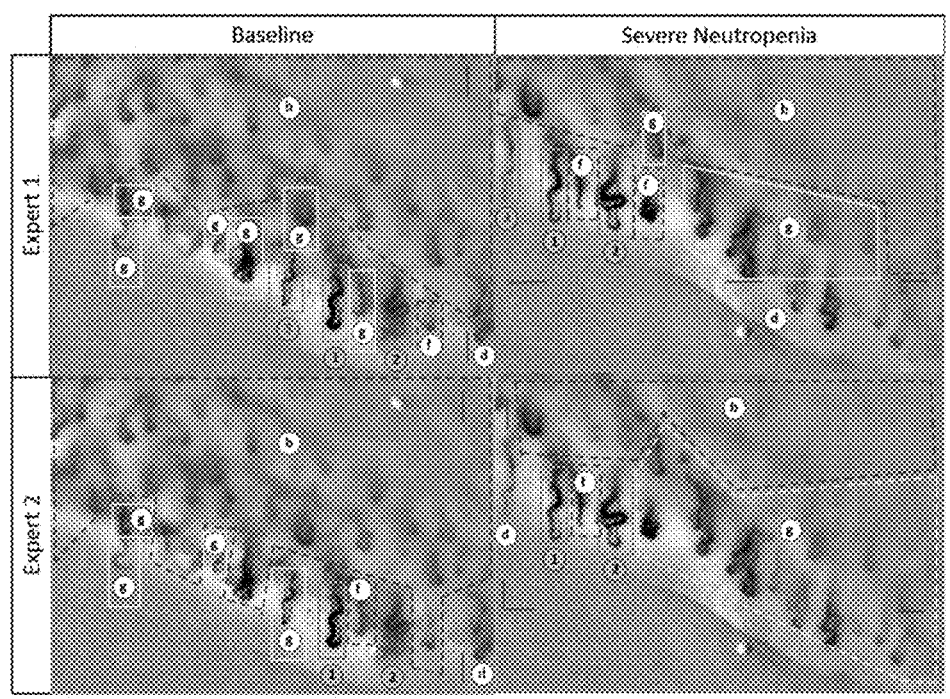
FIG. 60 shows capillary-selection from both experts in raw-video pair for Patient 10.

FIG. 60 shows capillary selection from both experts in raw-video pair from Patient 10. The videos acquired in baseline and severe-neutropenic states are displayed. The green boxes outline the selected capillary pairs which, according to each of the two experts complied with the quality criteria for both baseline and severe-neutropenia acquisitions. The red regions/capillaries are discarded due to non-compliance with the quality criteria, i.e., due in this instance to (b) lack of focus, (d) out-of-field-of-view movements, and (f) lack of clear morphology. The red lines/corners in the baseline videos outline the effective field of view outside which capillaries must be discarded as they disappear during several frames due to camera movements during acquisition. The yellow boxes outline capillaries that were initially selected in baseline but were discarded later due to non-compliance in the severe-neutropenia acquisition (g). Both experts made the selection process independently and, after that, only capillaries where both experts agreed (black numbers), discarding the rest of them (red numbers).

Each of the following references is incorporated herein by reference in their entirety.

Tsukada, Kosuke, et al. "Image correlation method for measuring blood flow velocity in microcirculation: correlation window' simulation and in vivo image analysis." Physiological measurement 21.4 (2000): 459.

Langeder, Florian, and Bernhard G. Zagar. "Image processing strategies to accurately measure red blood cell motion in superficial capillaries." Systems, Signals and Devices, 2009. SSD '09. 6th International Multi-Conference on. IEEE, 2009.

Wu, Chih-Chieh, et al. "Red blood cell velocity measurements of complete capillary in finger nail-fold using optical flow estimation." Microvascular research 78.3 (2009): 319-324.

Huang, Tzung-Chi, et al. "Experimental estimation of blood flow velocity through simulation of intravital microscopic imaging in micro-vessels by different image processing methods." Microvascular research 80.3 (2010): 477-483.

Wu, Chih-Chieh, et al. "Accuracy evaluation of RBC velocity measurement in nail-fold capillaries." Microvascular research 81.3 (2011): 252-260.

Lo, Lun-Chien, et al. "Pseudo three-dimensional vision-based nail-fold morphological and hemodynamic analysis." Computers in biology and medicine 42.9 (2012): 873-884.

Wang, Mingyi, et al. "Full-field velocity imaging of red blood cells in capillaries with spatiotemporal demodulation autocorrelation." Journal of biomedical optics 21.3 (2016): 036007-036007.

J. Crawford, D. C. Dale, and G. H. Lyman (2004). Chemotherapy-induced neutropenia: risks, consequences, and new directions for its management. *Cancer,* 100(2), 228-237.

M. E. van Wolfswinkel, K. Vliegenthart-Jongbloed, M. de Mendonça Melo, P. C. Wever, M. B. McCall, R. Koelewijn, J. J. van Hellemond, and P. J. van Genderen (2013). Predictive value of lymphocytopenia and the neutrophil-lymphocyte count ratio for severe imported malaria. *Malar. J.,* 12(1), 101.

T. Honda, T. Uehara, G. Matsumoto, S. Arai, and M. Sugano (2016). Neutrophil left shift and white blood cell count as markers of bacterial infection. *Clin. Chim. Acta,* 457, 46-53.

T. B. Newman, D. Draper, K. M. Puopolo, S. Wi, and G. J. Escobar (2014). Combining immature and total neutrophil counts to predict early onset sepsis in term and late preterm newborns: use of the I/T2. *Pediat. Infect. Dis.* 1, 33(8), 798.

A. Velo-Garcia, S. G. Castro, and D. A. Isenberg (2016). The diagnosis and management of the haematologic manifestations of lupus. *J. Autoimmun.*, 74, 139-160.

D. C. Dale (2014). Understanding neutropenia. *Curr. Opin. Hematol.*, 21(1), 1-2.

V. S. Hollis, J. A. Holloway, S. Harris, D. Spencer, C. van Berkel, and H. Morgan (2012). Comparison of venous and capillary differential leukocyte counts using a standard hematology analyzer and a novel microfluidic impedance cytometer. *PloS one*, 7(9), e43702.

C. L. Ghai (2012). *A textbook of practical physiology*. JP Medical Ltd.

S. Sharma, J. Zapatero-Rodriguez, P. Estrela, and R. O'Kennedy (2015). Point-of-care diagnostics in low resource settings: present status and future role of microfluidics. *Biosensors*, 5(3), 577-601.

Y. Mendelson (1992). Pulse oximetry: theory and applications for noninvasive monitoring. *Clin. Chem.*, 38(9), 1601-1607.

A. Trotti, A. D. Colevas, A. Setser, V. Rusch, D. Jaques, V. Budach, C. Langer, B. Murphy, R. Cumberlin, C. N. Coleman, and P. Rubin (2003, July). CTCAE v3.0: development of a comprehensive grading system for the adverse effects of cancer treatment. In *Semin. Radiat. Oncol.* (Vol. 13, No. 3, pp. 176-181). WB Saunders.

G. H. Lyman, M. S. Poniewierski, J. Crawford, D. C. Dale, and E. Culakova (2015). Cost of Hospitalization in Patients with Cancer and Febrile Neutropenia and Impact of Comorbid Conditions. *Blood*, 126(23), 2089-2089.

G. H. Lyman, C. H. Lyman, O. Agboola, and Anc Study Group. (2005). Risk models for predicting chemotherapy-induced neutropenia. *Oncologist*, 10(6), 427-437.

J. De Naurois, I. Novitzky-Basso, M. J. Gill, F. M. Marti, M. H. Cullen, F. Roila, and ESMO Guidelines Working Group. (2010). Management of febrile neutropenia: ESMO clinical practice guidelines. *Ann. Oncol.*, 21(suppl 5), v252-v256.

G. W. Schmid-Schonbein, S. Usami, R. Skalak, and S. Chien (1980). The interaction of leukocytes and erythrocytes in capillary and postcapillary vessels. *Microvasc. Res.*, 19(1), 45-70.

S. H. Sinclair, M. Azar-Cavanagh, K. A. Soper, R. F. Tuma, and H. N. Mayrovitz (1989). Investigation of the source of the blue field entoptic phenomenon. *Invest. Ophthalmol. Vis. Sci.*, 30(4), 668-673.

A. Roggan, M. Friebel, K. Dörschel, A. Hahn, and G. Muller (1999). Optical properties of circulating human blood in the wavelength range 400-2500 nm. *J. Biomed. Opt.*, 4(1), 36-46.

A. Uji, M. Hangai, S. Ooto, K. Takayama, N. Arakawa, H. Imamura, K. Nozato, and N. Yoshimura (2012). The source of moving particles in parafoveal capillaries detected by adaptive optics scanning laser ophthalmoscopy. Invest. *Ophthalmol. Vis. Sci.*, 53(1), 171-178.

U. Schmidt-Gross (1954). Entoptische Beurteilung der Leukocytenzahl. *Klin. Wochenschr.*, 32(33-34), 817-819.

T. Rimmer, E. M., Kohner, and J. M. Goldman (1988). Retinal blood velocity in patients with leukocyte disorders. *Arch. Ophthalmol.*, 106(11), 1548-1552.

G. Fuchsjäger-Mayrl, M. Malec, E. Polska, B. Jilma, M. Wolzt, and L. Schmetterer (2002). Effects of granulocyte colony stimulating factor on retinal leukocyte and erythrocyte flux in the human retina. *Invest. Ophthalmol. Vis. Sci.*, 43(5), 1520-1524.

C. E. Curtis, W. G. Iacono, and M. Beiser (1999). Relationship between nailfold plexus visibility and clinical, neuropsychological, and brain structural measures in schizophrenia. *Biol. Psychiatry*, 46(1), 102-109.

F. Lefford and J. C. Edwards (1986). Nailfold capillary microscopy in connective tissue disease: a quantitative morphological analysis. *Ann. Rheum. Dis.*, 45(9), 741-749.

Z. Nagy and L. Czirjak (2004). Nailfold digital capillaroscopy in 447 patients with connective tissue disease and Raynaud's disease. *J. Eur. Acad. Dermatol. Venereol.*, 18(1), 62-68.

L. K. Mercer, T. L. Moore, H. Chinoy, A. K. Murray, A. Vail, R. G. Cooper, and A. L. Herrick (2010). Quantitative nailfold video capillaroscopy in patients with idiopathic inflammatory myopathy. *Rheumatology*, 49(9), 1699-1705.

A. K. Murray, A. Vail, T. L. Moore, J. B. Manning, C. J. Taylor, and A. L. Herrick (2012). The influence of measurement location on reliability of quantitative nailfold videocapillaroscopy in patients with SSc. *Rheumatology*, kes007.

H. M. Hofstee, E. H. Serné, C. Roberts, R. Hesselstrand, A. Scheja, T. L. Moore, M. Wildt, J. B. Manning, A. V. Noordegraaf, A. E. Voskuyl, and A. L. Herrick (2011). A multicentre study on the reliability of qualitative and quantitative nail-fold videocapillaroscopy assessment. *Rheumatology*, ker403.

S. J. Simnett, L. A. Stewart, J. Sweetenham, G. Morgan, and P. W. Johnson (2000). Autologous stem cell transplantation for malignancy: a systematic review of the literature. *Clin. Lab. Haematol.*, 22(2), 61-72.

L. Golan, D. Yeheskely-Hayon, L. Minai, E. J. Dann, and D. Yelin (2012). Noninvasive imaging of flowing blood cells using label-free spectrally encoded flow cytometry. *Biomed. Opt. Express*, 3(6), 1455-1464.

N. Mugii, M. Hasegawa, Y. Hamaguchi, C. Tanaka, K. Kaji, K. Komura, I. Ueda-Hayakawa, S. Hone, M. Ikuta, K. Tachino, F. Ogawa, S. Sato, M. Fujimoto, and K. Takehara (2009). Reduced red blood cell velocity in nail-fold capillaries as a sensitive and specific indicator of microcirculation injury in systemic sclerosis. *Rheumatology*, 48(6), 696-703.

A. Bourquard, I. Butterworth, A. Sanchez-Ferro, L. Giancardo, L. Soenksen, C. Cerrato, R. Flores, and C. Castro-Gonzalez (2015, August). Analysis of white blood cell dynamics in nailfold capillaries. In Conf. Proc. IEEE Eng. Med. Biol. Soc., 2015 37th *Annual International Conference of the IEEE* (pp. 7470-7473).

C. Castro-Gonzalez, I. Butterworth, A. Bourquard, and A. Sanchez-Ferro (2015). Systems, apparatus, and methods for analyzing blood cell dynamics. U.S. patent application Ser. No. 14/951,260.

C. C. Wu, G. Zhang, T. C. Huang, and K. P. Lin (2009). Red blood cell velocity measurements of complete capillary in finger nail-fold using optical flow estimation. *Microvasc. Res.*, 78(3), 319-324.

T. C. Huang, W. C. Lin, C. C. Wu, G. Zhang, and K. P. Lin (2010). Experimental estimation of blood flow velocity through simulation of intravital microscopic imaging in micro-vessels by different image processing methods. *Microvasc. Res.*, 80(3), 477-483.

C. C. Wu, W. C. Lin, G. Zhang, C. W. Chang, R. S. Liu, K. P. Lin, and T. C. Huang (2011). Accuracy evaluation of RBC velocity measurement in nail-fold capillaries. *Microvasc. Res.*, 81(3), 252-260.

C. H. Wu, T. D. Wang, C. H. Hsieh, S. H. Huang, J. W. Lin, S. C. Hsu, H. T. Wu, Y. M. Wu, and T. M. Liu (2016).

Imaging Cytometry of Human Leukocytes with Third Harmonic Generation Microscopy. *Sci. Rep.*, 6.

T. C. Shih, G. Zhang, C. C. Wu, H. D. Hsiao, T. H. Wu, K. P. Lin, and T. C. Huang (2011, January). Hemodynamic analysis of capillary in finger nail-fold using computational fluid dynamics and image estimation. *Microvasc. Res.* 81(1), 68-72.

D. Mattes, D. R. Haynor, H. Vesselle, T. K. Lewellyn, and W. Eubank (2001, July). Nonrigid multimodality image registration. In *Med. Imaging* (pp. 1609-1620). International Society for Optics and Photonics.

G. W. Schmid-Schonbein, R. Skalak, S. Usami, and S. Chien (1980). Cell distribution in capillary networks. *Microvasc. Res.*, 19(1), 18-44.

J. H. Lee, J. Jimenez, I. R. Butterworth, C. Castro-Gonzalez, S. K. Shukla, B. Marti-Fuster, L. Elvira, D. S. Boning, and B. W. Anthony (2015, October). Measurement of very low concentration of microparticles in fluid by single particle detection using acoustic radiation force induced particle motion. In 2015 *IEEE Int. Ultrason. Symp.* (pp. 1-4).

J. Tam, P. Tiruveedhula, and A. Roorda (2011). Characterization of single-file flow through human retinal parafoveal capillaries using an adaptive optics scanning laser ophthalmoscope. *Biomed. Opt. Express*, 2(4), 781-793.

P. D. Allen, C. J. Taylor, A. L. Herrick, and T. Moore (1998, September). Enhancement of Temporally Variable Features in Nailfold Capillary Patterns. In *BMVC* (pp. 1-10).

M. Kass, A. Witkin, and D. Terzopoulos (1988). Snakes: Active contour models. *Int. J. Comput. Vision*, 1(4), 321-331.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments disclosed herein may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising"

can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A system, comprising:
   a platform to receive a body portion of a user during use;
   an imaging device coupled to the platform and to acquire a set of images of at least a capillary bed of the body portion;
   a processor, communicably coupled to the imaging device, to:
   detect, by the processor, in each image of the set of images, one or more capillaries in the capillary bed of the body portion to identify a first set of capillaries across the set of images, including:
   estimating one or more attributes of each capillary of the first set of capillaries; and
   when a first attribute of the one or more attributes of each capillary of the first set of capillaries meets a predetermined criterion for the first attribute, selecting that capillary for inclusion in the first set of capillaries, the one or more attributes including one or more structural attributes, one or more flow attributes, one or more imaging attributes, or combinations thereof; and
   identify a subset of capillaries from the first set of capillaries as a second set of capillaries such that each capillary of the second set of capillaries is visible in at least a predetermined number of images of the set of images.

2. The system of claim 1, wherein the imaging device acquires the set of images as a set of frames of a video.

3. The system of claim 1, further comprising an illumination source coupled to the platform and to illuminate the body portion, wherein the imaging device acquires the set of images in response to the illumination of the body portion.

4. The system of claim 1, the one or more structural attributes selected from the group consisting of average capillary diameter, lateral capillary diameter, vertical capillary diameter capillary length, and capillary shape.

5. The system of claim 1, the one or more imaging attributes selected from the group consisting of contrast, focus, signal-to-noise ratio, and image stability.

6. The system of claim 1, wherein the first attribute is average capillary diameter, wherein each capillary of the second set of capillaries has an estimated average capillary diameter from about 10 µm to about 20 µm.

7. The system of claim 1, wherein the processor further:
   detects, for the set of images and in the second set of capillaries, a set of cellular events, each cellular event of the set of cellular events associated with passage of a white blood cell in a capillary of the second set of capillaries; and
   estimates an event count for the second set of capillaries based on the set of cellular events.

8. The system of claim 7, wherein the processor further:
   for each capillary of the second set of capillaries, estimates a quality factor;
   estimates the event count based on the set of cellular events and the quality factor associated with each capillary of the second set of capillaries.

9. The system of claim 8, wherein the processor further:
   receives a set of training images associated with capillary beds in body portions of a set of training users;
   generates, via supervised learning, an event count threshold based on the set of training images;
   classifies the user to a first user type of a set of user types based on the event count and the event count threshold, at least one user type of the set of user types associated with a diagnosis of neutropenia; and
   transmits an indication of the first user type to the user.

10. The system of claim 1, wherein the processor further generates a confidence value associated with the image of each capillary of the first set of capillaries in the set of images, the first set of capillaries including those capillaries for which the confidence value, for each image in which that capillary is detected, exceeds a confidence threshold.

11. The system of claim 1, wherein the processor detects the first set of capillaries by:
   receiving a set of training images including a specification of one or more capillaries visible within each image of the set of training images;

training a neural network on the set of training images; and applying the set of images to the neutral network to detect the first set of capillaries.

12. The system of claim 1, wherein the processor detects the first set of capillaries by applying the set of images to a neutral network, the neural network being trained on a set of training images including a specification of one or more capillaries visible within each image of the set of training images.

13. A method, comprising:

acquiring a set of images of a capillary bed of a body portion of a user;

detecting, without user input, in each image of the set of images, one or more capillaries in the body portion to identify a first set of capillaries across the set of images, including:

estimating one or more attributes of each capillary of the first set of capillaries; and when a first attribute of the one or more attributes of each capillary of the first set of capillaries meets a predetermined criterion for the first attribute, selecting that capillary selected for inclusion in the first set of capillaries, the one or more attributes including one or more structural attributes, one or more flow attributes, one or more imaging attributes, or combinations thereof; and identifying a subset of capillaries from the first set of capillaries as a second set from the first set of capillaries such that each capillary of the second set of capillaries is visible in at least a predetermined number of images of the set of images.

14. The method of claim 13, the acquiring including acquiring the set of images as a set of frames of a video.

15. The method of claim 13, further comprising illuminating the body portion, the acquiring the set of images being in response to the illumination of the body portion.

16. The method of claim 13, the one or more structural attributes selected from the group consisting of average capillary diameter, lateral capillary diameter, vertical capillary diameter capillary length, and capillary shape.

17. The method of claim 13, the one or more imaging attributes selected from the group consisting of contrast, focus, signal-to-noise ratio, and image stability.

18. The method of claim 13, wherein the first attribute is average capillary diameter, wherein each capillary of the second set of capillaries has an estimated average capillary diameter from about 10 µm to about 20 µm.

19. The method of claim 13, further comprising:

detecting, for the set of images and in the second set of capillaries, a set of cellular events, each cellular event of the set of cellular events associated with passage of a white blood cell in a capillary of the second set of capillaries; and estimating an event count for the second set of capillaries based on the set of cellular events.

20. The method of claim 19, further comprising:

for each capillary of the second set of capillaries, estimating a quality factor;

estimating the event count based on the set of cellular events and the quality factor associated with each capillary of the second set of capillaries.

21. The method of claim 20, further comprising:

receiving a set of training images associated with capillary beds in body portions of a set of training users;

generating, via supervised learning, an event count threshold based on the set of training images; and classifying the user to a first user type of a set of user types based on the event count and the event count threshold, at least one user type of the set of user types associated with a diagnosis of neutropenia; and transmitting an indication of the first user type to the user.

22. The method of claim 13, further comprising generating a confidence value associated with the image of each capillary of the first set of capillaries in the set of images, the first set of capillaries including those capillaries for which the confidence value, for each image in which that capillary is detected, exceeds a confidence threshold.

23. The method of claim 13, the detecting the first set of capillaries further including:

receiving a set of training images including a specification of one or more capillaries visible within each image of the set of training images;

training a neural network on the set of training images; and applying the set of images to the neutral network to detect the first set of capillaries.

24. The method of claim 13, the detecting the first set of capillaries further including applying the set of images to a neutral network, the neural network being trained on a set of training images including a specification of one or more capillaries visible within each image of the set of training images.

25. The method of claim 13, wherein the body portion is a nailfold portion of a finger of the user.

26. A device comprising a processor to:

receive a set of images of a capillary bed in a body portion of a user;

detect, by the processor, in each image of the set of images, one or more capillaries in the body portion to identify a first set of capillaries across the set of images, including:

estimating one or more attributes of each capillary of the first set of capillaries: and when a first attribute of the one or more attributes of each capillary of the first set of capillaries meets a predetermined criterion for the first attribute, selecting that capillary for inclusion in the first set of capillaries, the one or more attributes including one or more structural attributes, one or more flow attributes, one or more imaging attributes, or combinations thereof, such that a first attribute of the one or more attributes of each capillary of the first set of capillaries meets a predetermined criterion for the first attribute;

identify a subset of capillaries from the first set of capillaries as a second set of capillaries such that each capillary of the second set of capillaries is visible in at least a predetermined number of images of the set of images;

detect, for the set of images and in the second set of capillaries, a set of cellular events, each cellular event of the set of cellular events associated with passage of a white blood cell in a capillary of the second set of capillaries; and estimate an event count for the second set of capillaries based on the set of cellular events.

27. The device of claim 26, wherein the processor further:

for each capillary of the second set of capillaries, estimates a quality factor;

estimates the event count based on the set of cellular events and the quality factor associated with each capillary of the second set of capillaries.

28. The device of claim 27, wherein the processor further:
receives a set of training images associated with capillary beds in body portions of a set of training users;
generates, via supervised learning, an event count threshold based on the set of training images; and
classifies the user to a first user type of a set of user types based on the event count and the event count threshold, at least one user type of the set of user types associated with a diagnosis of neutropenia; and
transmits an indication of the first user type to the user.

29. The device of claim 26, wherein the processor further generates a confidence value associated with the image of each capillary of the first set of capillaries in the set of images, the first set of capillaries including those capillaries for which the confidence value, for each image in which that capillary is detected, exceeds a confidence threshold.

30. The device of claim 26, wherein the processor detects the first set of capillaries by:
receiving a set of training images including a specification of one or more capillaries visible within each image of the set of training images;
training a neural network on the set of training images; and
applying the set of images to the neutral network to detect the first set of capillaries.

31. The device of claim 26, wherein the processor detects the first set of capillaries by applying the set of images to a neutral network, the neural network being trained on a set of training images including a specification of one or more capillaries visible within each image of the set of training images.

* * * * *